US009360486B2

(12) United States Patent
Ferreira et al.

(10) Patent No.: US 9,360,486 B2
(45) Date of Patent: Jun. 7, 2016

(54) ALLERGEN FRAGMENTS

(75) Inventors: Fatima Ferreira, Salzburg (AT); Barbara Bohle, Vienna (AT); Beatrice Jahn-Schmid, Vienna (AT); Nicole Wopfner, Salzburg (AT); Georg Schmidt, Salzburg (AT); Christof Ebner, Brunn am Gebirge (AT)

(73) Assignee: Biomay AG, Vienna (AT)

( * ) Notice: Subject to any disclaimer, the term of this patent is extended or adjusted under 35 U.S.C. 154(b) by 644 days.

(21) Appl. No.: 12/526,143

(22) PCT Filed: Feb. 13, 2008

(86) PCT No.: PCT/EP2008/001092
§ 371 (c)(1),
(2), (4) Date: Aug. 6, 2009

(87) PCT Pub. No.: WO2008/098749
PCT Pub. Date: Aug. 21, 2008

(65) Prior Publication Data
US 2010/0104606 A1    Apr. 29, 2010

(30) Foreign Application Priority Data
Feb. 13, 2007   (EP) .................... 07102260

(51) Int. Cl.
| A61K 38/00 | (2006.01) |
| A61K 38/04 | (2006.01) |
| A61K 39/00 | (2006.01) |
| A61K 39/35 | (2006.01) |
| A61K 39/36 | (2006.01) |
| A61K 39/38 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| G01N 33/68 | (2006.01) |
| C07K 14/415 | (2006.01) |

(52) U.S. Cl.
CPC .......... *G01N 33/6893* (2013.01); *C07K 14/415* (2013.01); *G01N 2800/24* (2013.01)

(58) Field of Classification Search
None
See application file for complete search history.

(56) References Cited

U.S. PATENT DOCUMENTS 6,335,019 B1   1/2002   Rogers et al.

FOREIGN PATENT DOCUMENTS

| WO | 9011293 A1 | 10/1990 |
| WO | WO 93/21321 | * 10/1993 | ............. C12N 15/29 |
| WO | 9613589 A1 | 5/1996 |
| WO | 9934826 A1 | 7/1999 |

OTHER PUBLICATIONS

Smith et al. 'Monoclonal antibodies to denatured ragweed pollen allergen Amb a I: characterization, specificity for the denatured allergen, and utilization for the isolation of immunogenic peptides of Amb a I.' Mol. Immunol. 25:355-365, 1988.*
Colman et al. 'Effects of amino acid sequence changes on antibody-antigen interactions.' Research in Immunology 145(1):33-36, 1994.*
Abaza et al. Effects of amino acid substitutions outside an antigenic site on protein binding to monoclonal antibodies of predetermined specificity obtained by peptide immunization: demonstration with region 94-100 (antigenic site 3) of myoglobin.° J. Prot. Chem. 11(5):433-444, 1992.*
Lederrnan et al. 'A single amino acid substitution in a common African allele of the CD4 molecule ablates binding of the monoclonal antibody, OKT4.' Molec. Immunolo 28:1171-1181, 1991.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Kinnunen et al. 'Potential of an altered peptide ligand of lipocalin allergen Bos d 2 for peptide immunotherapy.' J. Allergy Clin Immunol. 119(4):965-972, 2007.*
Kuby et al. 'Immunology.' Fourth Edition, Chapter 18: 449-465, Jan. 15, 2000.*
Chang et al. 'Peptide length-based prediction of peptide-MHC class II binding.' Bioinformatics. 22(22):2761-2767, 2006.*
Lerner et al. 'Tapping the immunological repertoire to produce antibodies of predetermined specificity.' 299:592-596, 1982.*
Cardinale, et al., "Matrix-Assisted Lase Desorption/Ionization Time-of-flight(MALDI-TOF) Mass Spectrometry in the Analysis of Allergen Vaccines", Journal of Allergy and Clinical Immunology, (2001), S19, 107(2).
Griffith, et al., "Sequence Polymorphism of Amb a I and Amb a II, The Major Allergens in Ambrosia Artemisiifolia (Short Ragweed)", International Archives of Allergy and Applied Immunology, (1991), 296-304, 96.
King, et al., "Chemical Modifications of the Major Allergen of Ragweed Pollen, Antigen E", Immunochemistry, (1974), 83-92, 11(2).
Michael, et al., "Modulation of the immune response to ragweed allergens by peptic fragments", Clinical and Experimental Allergy: Journal of the British Society for Allergy and Clinical Immunology, (1990), 669-674, 20(6).

(Continued)

*Primary Examiner* — Nora Rooney
(74) *Attorney, Agent, or Firm* — Oblon, McClelland, Maier & Neustadt, L.L.P.

(57) ABSTRACT

The present invention relates to a peptide derived from the ragweed pollen allergen Amb a (1) and comprising (6 to 50) amino acid residues and pharmaceutical preparations comprising said peptide and uses thereof.

13 Claims, 15 Drawing Sheets

(56) References Cited

OTHER PUBLICATIONS

Rafnar, et al., "Cloning of Amb a I (Antigen E), the Major Allergen Family of Short Ragweed Pollen", Journal of Biological Chemistry, American Society for Biochemisrty and Molecular Biology, Inc., (1991), 1229-1236, 266(2).

Sone, et al., "Identification of human T cell epitopes in Japanese cypress pollen allergen, Cha o 1, elucidates the intrinsic mechanism of cross-allergenicity between Cha o 1 and Cry j 1, the major allergen of Japanese cedar pollen, at the T cell level", Clinical and Experimental Allergy, (2005), 664-671, 35(5).

* cited by examiner

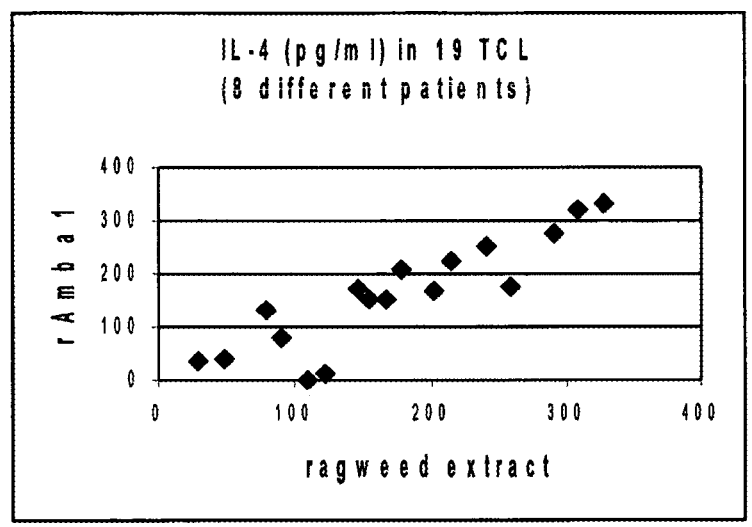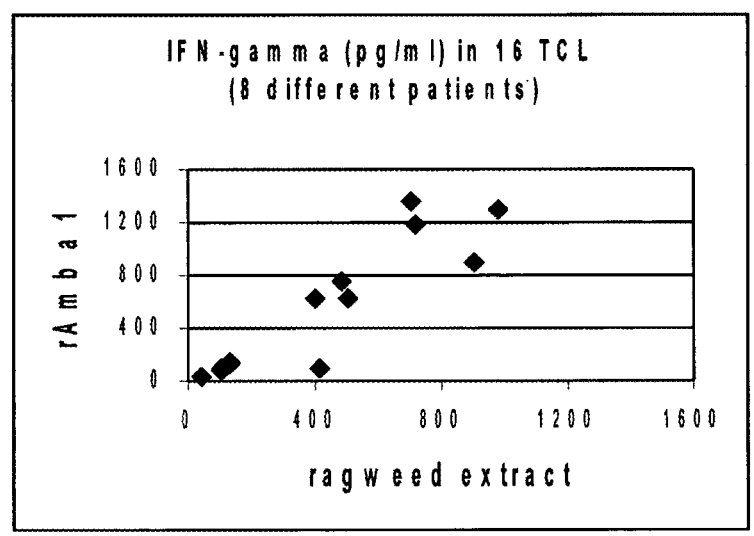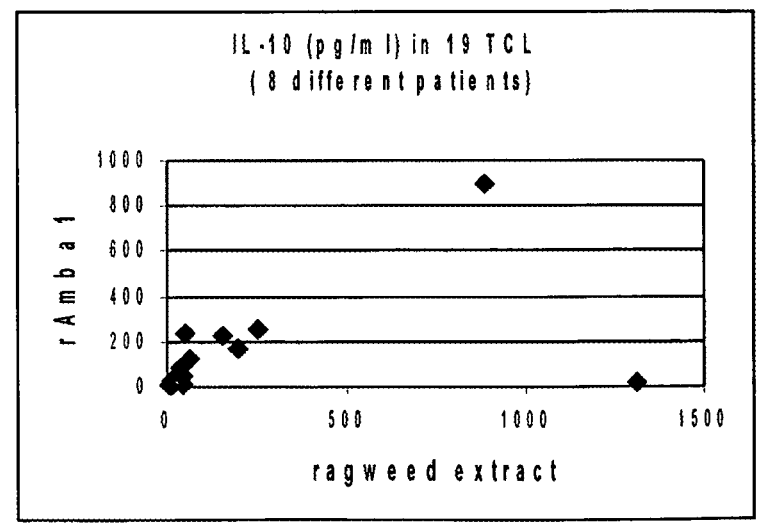
Fig. 5

Similar T cell epitopes are recognized by TCL induced with either natural or rAmb a 1.3

Bold: TCL induced with rAmb a 1.3
U: TCL induced with ragweed extract

┌╴╴╴╴┐ T cell epitopes >45% prevalence
└────┘ T cell epitopes >30% -45% prevalence MGIKQCCYILYFTLALVALLQPVRSAEGVGEILPSVNETRSLQACEAYNIID
KCWRGKADWENNRQALADCAQGFAKGTYGGKWGDVYTVTSNLDDDV
ANPKEGTLRFAAAQNRPLWIIFKNDMVINLNQELVVNSDKTIDGRGVKVE
INGGLTLMNVKNIIIHNINIHDVKVLPGSMIKSNDGPPILRQASDGDTINVA
GSSQIWIDHCSLSKSFDGLVDVTLGSTHVTISNCKFTQQSKAILLGADDT
HVQDKGMLATVAFNMFTDNVDQRMPRCRFGFFQVVNNNYDRWGTYAI
GGSSAPTILCQGNRFLAPDDQIKKNVLARTGTGAAESMAWNWRSDKDL
LENGAIFVTISGSDPVLTPVQSAGMIPAEPGEAAIKLTSSAGVLSCRPGAPC

Fig. 7

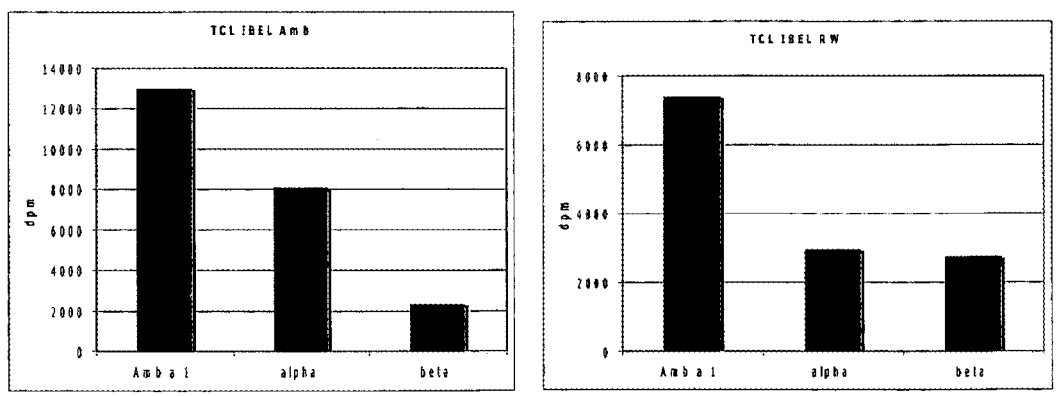

Fig. 21

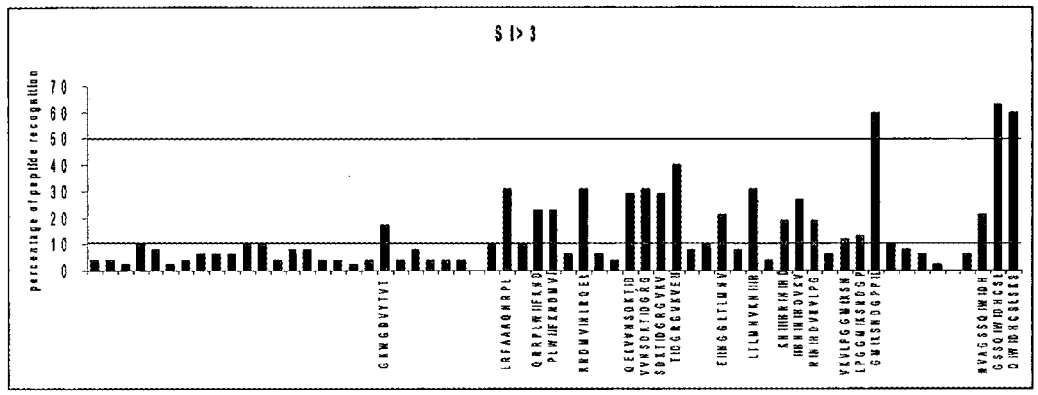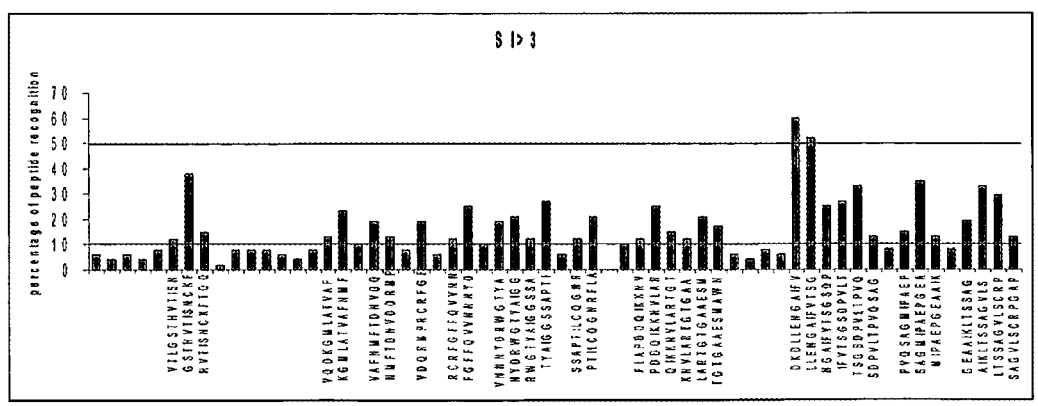
Fig. 8

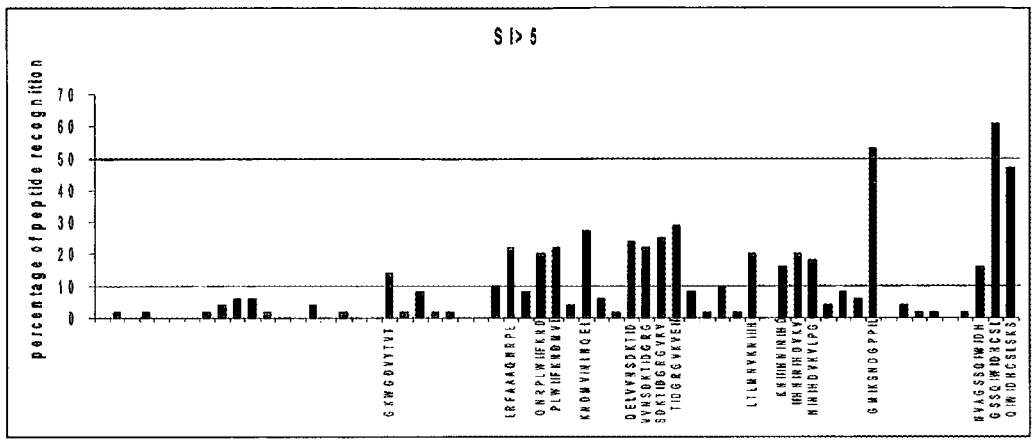
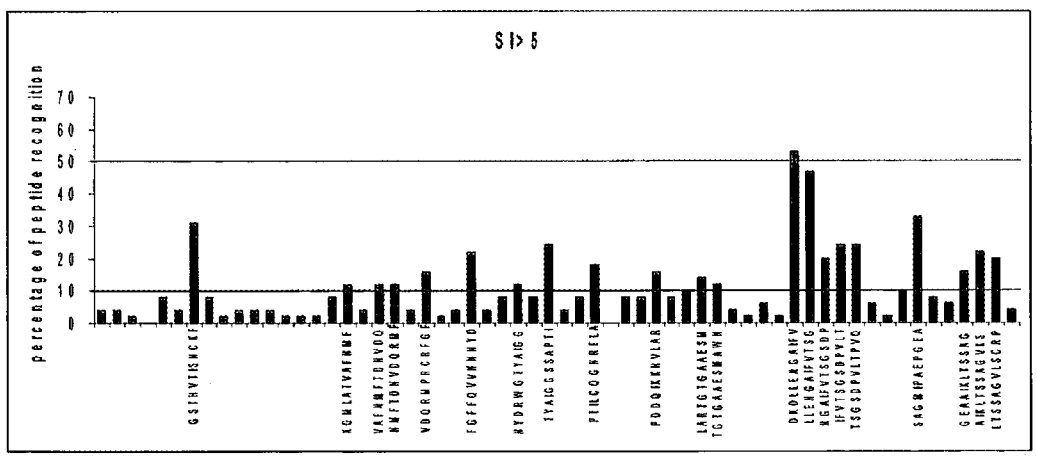
Fig. 8 cont.

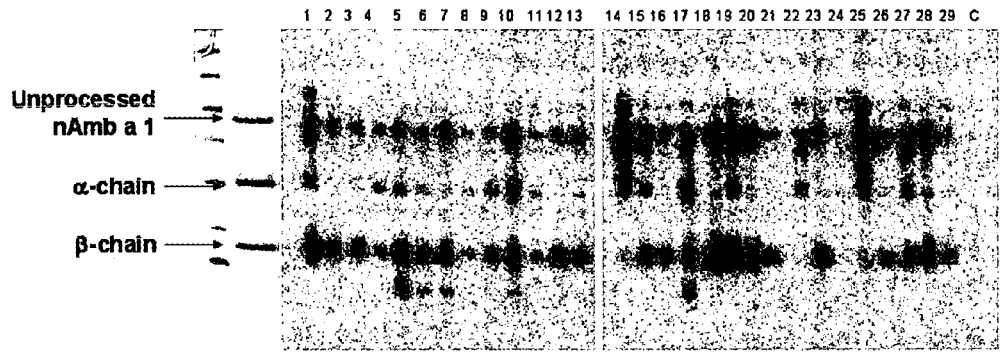

Fig. 9

```
nAmb a 1                       TSGAYNIIDGxxRxKA...
Amb  a 1.1      AEDLQEILP-VNETRR-LTTSGAYNIIDGCWRGKA...
Amb  a 1.2      AEDVEEFLPSANETRRSLKACEAHNIIDKCWRCKA...
Amb  a 1.3      AEGVGEILPSVNETR-SLQACEAYNIIDKCWRGKA...
Amb  a 1.4      AEDLQQILPSANETR-SLTTCGTYNIIDGCWRGKA...
Amb  a 2    GRLGEEVDILPSPNDTRRSL-GCEAHNIIDKCWRCKP...
```

Fig. 11

```
nAmb a 1        APRDGDDISIIGSSQ...
nAmb a 1        APSAGSAIDAIGSSQ...
Amb  a 1.1      AGSDGDAISISGSSQ...
Amb  a 1.2      QQSDGDAINVAGSSQ...
Amb  a 1.3      QASDGDTINVAGSSQ...
Amb  a 1.4      KGSDGDAIGISGGSQ...
Amb  a 2        HQSDGDAIHVTGSSD...
```

Fig. 12

```
nAmb a 1                       TSGAYNIIDGCxRGKAD...
Amb  a 1.1      AEDLQEILP-VNETRR-LTTSGAYNIIDGCWRGKAD...
Amb  a 1.2      AEDVEEFLPSANETRRSLKACEAHNIIDKCWRCKAD...
Amb  a 1.3      AEGVGEILPSVNETR-SLQACEAYNIIDKCWRGKAD...
Amb  a 1.4      AEDLQQILPSANETR-SLTTCGTYNIIDGCWRGKAD...
Amb  a 2    GRLGEEVDILPSPNDTRRSL-GCEAHNIIDKCWRCKPD...
```

Fig. 13

Amb a 1.1 isoform (GenBank Acession M80558/M63116)

MGIKHCCYILYFTLALVTLLQPVRSAEDLQEILPVNETRRLT TSGAYNIIDGCWRGKADWAENRKALADCAQGFG
KGTVGGKDGDIYTVTSELDDDVANPKEGTLRFGAAQNRPLWIIFERDMVIRLDKEMVVNSDKTIDGRGAKVEIIN
AGFTLNGVKNVIIHNINMHDVKVNPGGLIKSNDGPAAPR AGSDGDAISISGSSQIWIDHCSLSKSVDGLVDAKLG
TTRLTVSNSLFTQHQFVLLFGAGDENIEDRGMLATVAFNTFTDNVDQRMPRCRHGPFQVVNNNYDKWGSYAIGGS
ASPTILSQGNRFCAPDERSKKNVLGRHGEAAAESMKWNWRTNKDVLENGAIFVASGVDPVLTPEQSAGMIPAEPG
ESALSLTSSAGVLSCQPGAPC

Amb a 1.2 isoform (GenBank Acession M80559/M62981)

MGIKHCCYILYFTLALVTLLQPVRSAEDVEEFLPSANETRRSLK ACEAHNIIDKCWRCKADWANNRQALADCAQG
FAKGTYGGKHGDVYTVTSDKDDDVANPKEGTLRFAAAQNRPLWIIFKRNMVIHLNQELVVNSDKTIDGRGVKVNI
VNAGLTLMNVKNIIIHNINIHDIKVCPGGMIKSNDGPPILR QQSDGDAINVAGSSQIWIDHCSLSKASDGLLDIT
LGSSHVTVSNCKFTQHQFVLLLGADDTHYQDKGMLATVAFNMFTDHVDQRMPRCRFGFFQVVNNNYDRWGTYAIG
GSSAPTILSQGNRFPAPDDIIKKNVLARTGTGNAESMSWNWRTDRDLLENGAIFLPSGSDPVLTPEQKAGMIPAE
PGEAVLRLTSSAGVLSCHQGAPC

Amb a 1.3 isoform (GenBank Acession C53240)

MGIKQCCYILYFTLALVALLQPVRSAEGVGEILPSVNETRSLQ ACEAYNIIDKCWRGKADWENNRQALADCAQGF
AKGTYGGKWGDVYTVTSNLDDDVANPKEGTLRFAAAQNRPLWIIFKNDMVINLNQELVVNSDKTIDGRGVKVEII
NGGLTLMNVKNIIIHNINIHDVKVLPGGMIKSNDGPPILR QASDGDTINVAGSSQIWIDHCSLSKSFDGLVDVTL
GSTHVTISNCKFTQQSKAILLGADDTHVQDKGMLATVAFNMFTDNVDQRMPRCRFGFFQVVNNNYDRWGTYAIGG
SSAPTILCQGNRFLAPDDQIKKNVLARTGTGAAESMAWNWRSDKDLLENGAIFVTSGSDPVLTPVQSAGMIPAEP
GEAAIKLTSSAGVLSCRPGAPC

Amb a 1.4 isoform (GenBank Acession M80562)

MGIKHCCYILYFTLALVTLLQPVRSAEDLQQILPSANETRSLT TCGTYNIIDGCWRGKADWAENRKALADCAQGF
AKGTIGGKDGDIYTVTSELDDDVANPKEGTLRFGAAQNRPLWIIFARDMVIRLDRELAINNDKTIDGRGAKVEII
NAGFAIYNVKNIIIHNIIMHDIVVNPGGLIKSHDGPPVPR KGSDGDAIGISGGSQIWIDHCSLSKAVDGLIDAKH
GSTHFTVSNCLFTQHQYLLLFWDFDERGMLCTVAFNKFTDNVDQRMPNLRHGFVQVVNNNYERWGSYALGGSAGP
TILSQGNRFLASDIKKEVVGRYGESAMSESINWNWRSYMDVFENGAIFVPSGVDPVLTPEQNAGMIPAEPGEAVL
RLTSSAGVLSCQPGAPC

Amb a 2 isoform (GenBank Acession M80561)

MGIKHCCYILYFTLALVTLVQAGRLGEEVDILPSPNDTRRSLQGCEAHNIIDKCWRCKPDWAENRQALGNCAQGF
GKATHGGKWGDIYMVTSDQDDDVVNPKEGTLRFGATQDRPLWIIFQRDMIIYLQQEMVVTSDKTIDGRGAKVELV
YGGITLMNVKNVIIHNIDIHDVRVLPGGRIKSNGGPAIPR HQSDGDAIHVTGSSDIWIDHCTLSKSFDGLVDVNW
GSTGVTISNCKFTHHEKAVLLGASDTHPQDLKMHVTLAYNIFTNTVHERMPRCRFGFFQIVNNFYDRWDKYAIGG
SSNPTILSQGNKFVAPDFIYKKNVCLRTGAQEPEWMTWNWRTQNDVLENGAIFVASGSDPVLTAEQNAGMMQAEP
GDMVPQLTMNAGVLTCSPGAPC

Fig. 14

```
              10        20        30        40        50        60        70
               |         |         |         |         |         |         |
Amba1.1   MGIKHCCYILVFTLALVTLLQPVRSAEDLQEILP-VNETR-RLTTSGAVNIIDGCWRGKADWAENAKALA
Amba1.4   ........................Q...SA.....S...C.T..........................
Amba1.2   ......................VE.F..SA....RS.KACE.H....K...C.....N..Q...
Amba1.3   .....Q.............A.........GVG....S......S.QACE......K.........EN..Q...
Amba2     ...................V.AG.-LGEEVD...SP.D..RS.QGCE.H....K...C.P.....Q..G 80        90       100       110       120       130       140
               |         |         |         |         |         |         |
Amba1.1   DCAQGFGKGTVGGKDGDIYTVTSELDDDVANPKEGTLRFGAAQNRPLWIIFERDMVIRLDKEMVVNSDKT
Amba1.4   ......A...I...................................A.........A.LAI.N...
Amba1.2   ......A...Y..H..V.....DK.....................A..........K.N...H.NQ.L...
Amba1.3   ......A...Y..W..V.....N......................A..........KN....N.NQ.L.......
Amba2     N.......A.H...W....M...DQ....V.............T.D.......Q...I.Y.QQ....T....

150       160       170       180       190       200       210
               |         |         |         |         |         |         |
Amba1.1   IDGRGAKVEIINAGFTLNGVKNVIHNINMHDVKVNPGGLIKSNDGPRAPRAGSDGDAISISGSSQIWID
Amba1.4   ................AIYN...I......I....IV......H...PV..K.......G...G......
Amba1.2   .....V..N.V...L..MN...I......I..I..C...M.......PIL.QQ.....NVA........
Amba1.3   .....V......G.L..MN...I......I......L...M.......PIL.QA....T.NVA........
Amba2     ........LVYG.I..MN........DI...R.L...R....G...I..HQ......HVT...D....

220       230       240       250       260       270       280
               |         |         |         |         |         |         |
Amba1.1   HCSLSKSVDGLVDAKLGTTRLTVSNSLFTQHQFVLLFGAGDENIEDRGMLATVAFNTFTDNVDQRMPACR
Amba1.4   ......A....I...H.S.HF....C......YL...WDF.-----....C.....K........NL.
Amba1.2   ......AS...L.IT..SSHV....CK.......L..D.THYQ.K.........M...H.........
Amba1.3   ......F.....VT..S.HV.I..CK...QSKAI.L..D.THVQ.K.........M...........
Amba2     ..T....F.....VNW.S.GV.I..CK..H.EKAV.L...S.THFQ.LK.HV.L.Y.I...NT.HE......

290       300       310       320       330       340       350
               |         |         |         |         |         |         |
Amba1.1   HGFFQVVNNNYDKWGSYAIGGSASPTILSQGNRFCAPDERSKKNVLGRHGEARA-ESMKWNWRTNKDVLE
Amba1.4   ...V.......ER.....L....G............L.S.--I..E.V..Y..S.MS..IN....SYM..F.
Amba1.2   F...........R..T......SA..........F...DII.....A.T.TGN.....S....DR.L..
Amba1.3   F...........R..T......SA....C.....L...DQI.....A.T.TG.....A....SD..L..
Amba2     F....I...F..R.DK......SN........K.V...FIY....CL.T.AQEP..W.T.....QN....

360       370       380       390
               |         |         |         |
Amba1.1   NGAIFVASGVDPVLTPEQSAGMIPREPGESALSLTSSAGVLSCQPGAPC
Amba1.4   ......P..........N.........AV.R.................
Amba1.2   .....LP..S........K.........AV.R.........HQ....
Amba1.3   ......T..S......V...........A.IK.........R.....
Amba2     ..........S......A..N...MQ....DMVPQ..MN....T.S.....
```

Fig. 15 a) Putative naturally processed alpha and beta chain of Amb a 1.3

MGIKQCCYILYFTLALVALLQPVR SAEGVGEILPSVNETRSLQ ACEAYNIIDKCWRGKADWENNRQALADCAQGF AKGTYGGKWGDVYTVTSNLDDDVANPKEGTLRFAAAQNR PLWIIFKNDMVINLNQELVVNSDKTIDGRGVKVEII NGGLTLMNVKNIIIHNINIHDVKVLPGGMIKSNDGPPILR QASDGDTINVAGSSQIWIDHCSLSKSFDGLVDVTL GSTHVTISNCKFTQQSKAILLGADDTHVQDKGMLATVAFNMFTDNVDQRMPRCRFGFFQVVNNNYDRWGTYAIGG SSAPTILCQGNRFLAPDDQIKKNVLARTGTGAAESMAWNWRSDKDLLENGAIFVTSGSDPVLTPVQSAGMIPAEP GEAAIKLTSSAGVLSCRPGAPC b) Designed alpha and beta chain according to naturally processed MGIKQCCYILYFTLALVALLQPVR SAEGVGEILPSVNETRSLQACEAYNIIDKCWRGKADWENNRQALADCAQGF AKGTYGGKWGDVYTVTSNLDDDVANPKEGTLRFAAAQNR PLWIIFKNDMVINLNQELVVNSDKTIDGRGVKVEII NGGLTLMNVKNIIIHNINIHDVKVLPC GMIKSNDGPPII RQASDGDTINVAGSSQIWIDHCSLSKSFDGLVDVTL GSTHVTISNCKFTQQSKAILLGADDTHVQDKGMLATVAFNMFTDNVDQRMPRCRFGFFQVVNNNYDRWGTYAIGG SSAPTILCQGNRFLAPDDQIKKNVLARTGTGAAESMAWNWRSDKDLLENGAIFVTSGSDPVLTPVQSAGMIPAEP GEAAIKLTSSAGVLSCRPGAPC c) Modified alpha and beta chains (version 1)

MGIKQCCYILYFTLALVALLQPVR SAEGVGEILPSVNETRSLQACEA YNIIDKCWRGKADWENNRQALADCAQGF AKGTYGGKWGDVYTVTSNLDDDVANPKEGTLRFAAAQNR PLWIIFKNDMVINLNQELVVNSDKTIDGRGVKVEII NGGLTLMNVKNIIIHNINIHDVKVLPC GMIKSNDGPPII RQASDGDTINVAGSSQIWIDHCSLSKSFDGLVDVTL GSTHVTISNCKFTQQSKAILLGADDTHVQDKGMLATVAFNMFTDNVDQRMPRCRFGFFQVVNNNYDRWGTYAIGG SSAPTILCQGNRFLAPDDQIKKNVLARTGTGAAESMAWNWRSDKDLLENGAIFVTSGSDPVLTPVQSAGMIPAEP GEAAIKLTSSAGVLSCRPGAPC d) Modified alpha and beta chains (version 2)

MGIKQCCYILYFTLALVALLQPVR SAEGVGEILPSVNETRSLQAC EAYNIIDKCWRGKADWENNRQALADCAQGF AKGTYGGKWGDVYTVTSNLDDDVANPKEGTLRFAAAQNR PLWIIFKNDMVINLNQELVVNSDKTIDGRGVKVEII NGGLTLMNVKNIIIHNINIHDVKVLPC GMIKSNDGPPII RQASDGDTINVAGSSQIWIDHCSLSKSFDGLVDVTL GSTHVTISNCKFTQQSKAILLGADDTHVQDKGMLATVAFNMFTDNVDQRMPRCRFGFFQVVNNNYDRWGTYAIGG SSAPTILCQGNRFLAPDDQIKKNVLARTGTGAAESMAWNWRSDKDLLENGAIFVTSGSDPVLTPVQSAGMIPAEP GEAAIKLTSSAGVLSCRPGAPC

Fig. 16

```
mgikqccyilyftlalvallqpvrsAEGVGEILPSVNETRSLQACEAYN
IIDKCWRGKADWENNRQALADCAQGFAKGTYGGKWGDVYTVTSNLDDDV
ANPKEGTLRFAAAQNRPLWIIFKNDMVINLNQELVVNSDKTIDGRGVKV
EIINGGLTLMNVKNIIIHNINIHDVKVLPGGMIKSNDGPPILRQASDGD
TINVAGSSQIWIDHCSLSKSFDGLVDVTLGSTHVTISNCKFTQQSKAIL
LGADDTHVQDKGMLATVAFNMFTDNVDQRMPRCRFGFFQVVNNNYDRWG
TYAIGGSSAPTILCQGNRFLAPDDQIKKNVLARTGTGAAESMAWNWRSD
KDLLENGAIFVTSGSDPVLTPVQSAGMIPAEPGEAAIKLTSSAGVLSCR
PGAPC
``` mgi... vrs  —  Signal peptide
AEG...DVK  —  Beta chain
VLP...APC  —  Alpha chain

```
MGIKQCCYILYFTLALVALLQPVRSAEGVGEILPSVNETRSLQACEAYN
IIDKCWRGKADWENNRQALADCAQGFAKGTYGGKWGDVYTVTSNLDDDV
ANPKEGTLRFAAAQNRPLWIIFKNDMVINLNQELVVNSdktidgrgvkv
eiinggltlmnvKNIIIHNINIHDVKVLPGGMIKSNDGPPILRQASDGD
TINVAGSSQIWIDHCSLSKSFDGLVDVTLGSTHVTISNCKFQQSKAIL
LGADDTHVQDkgmlatvafnmfTDNvdqrmprcrfgfFQVVNNNYDRWG
TYAIGGSSAPTILCQGNRFLAPDDQIKknvlartgtgaaESMAWNWRSD
KDLLENGAIFVTSGSDPVLTPVQSAGMIPAEPGEAAIKLTSSAGVLSCR
PGAPC
```

- - - or small letters peptides positive in 10-20% of patients
☐ or italic peptides positive in 21-30% of patients
⋯⋯ peptides positive in 31-40% of patients
bold peptides positive in >50% of patients

Fig. 22

ALLERGEN FRAGMENTS

The present invention relates to Amb a 1 derived peptides.

Ragweed (*Ambrosia artemisiifolia*) and mugwort (*Artemisia vulgaris*) are important allergenic weeds belonging to the Asteraceae or Compositae plant family. Pollen of mugwort is one of the main causes of allergic reactions in late summer and autumn in Europe and affects about 10-14% of the patients suffering from pollinosis. Ragweed pollen represents the major source of allergenic protein in the United States, with a prevalence of about 50% in atopic27.10 individuals. In Europe, ragweed allergy is now rapidly increasing particularly in certain areas in France, Italy, Austria, Hungary, Croatia, and Bulgaria. Amb a 1, the major allergen of ragweed and Art v 1, the major allergen from mugwort, respectively, are unrelated proteins. Amb a 1 is an acidic 38 kDa non-glycosylated protein. Natural Amb a 1 undergoes proteolysis during purification and it is cleaved into two chains designated alpha and beta chain. The 26-kDa alpha-chain was reported to associate non-covalently with the 12-kDa beta chain (King et al. Immunochem 11:83-92, 1974). The Amb a 1 two-chain form seems to be immunologically indistinguishable from the full-length molecule (King et al. Arch Biochem Biophys 212:127-135, 1981).

Natural Amb a 1 (nAmb a 1) from ragweed was the first described and isolated allergen (King et al. Biochem 3:458-468, 1964). The cDNA coding for Amb a 1 was isolated from ragweed pollen in 1991 by Rafnar et al. (J. Biol. Chem. 266:1229-1236). But so far, a method to express and purify large amounts of active and correctly folded recombinant Amb a 1 (rAmb a 1) has not been reported.

WO 96/13589 relates to isolated peptides which are derived from Amb a 1 and comprise at least one T-cell epitope.

In the WO 90/11293 the amino acid sequence of Amb a 1 is described. Therein, also peptides of Amb a 1 have been identified which comprise T-cell-epitopes and which are capable of triggering an *Ambrosia*-specific immune response.

WO 99/34826 relates to methods and means for desensitizing patients by administering a peptide derived from an allergen, which peptide is capable of triggering a T-cell response in an individual.

In Michael J. G. et al. (J. Br. Soc. Aller. Clin. Immunol. 20 (6) (1990):669-674) the T-cell response of peptides which are obtained by a protease digestion of Amb a 1 has been examined.

Cardinale E. J. et al. (J. Aller. Clin. Immunol. 107 (2001):p 19) relates to the use of MALDI-TOF mass spectrometry for identifying and characterizing allergens.

U.S. Pat. No. 6,335,019 relates i.a., to Amb a 1 peptides capable of provoking a T-cell response against Amb a 1 in an individual.

Griffith et al. (Int. Arch. Aller. Appl. Immunol. 96 (1991): 296-304) relates to the sequence polymorphins of Amb a 1 and Amb a 2 family members.

It is an object of the present invention to provide peptides and molecules derived from ragweed pollen allergen Amb a 1 which can be employed in the treatment, prevention or diagnosis of allergies, in particular allergies caused by ragweed pollen allergens.

Therefore, the present invention relates to peptides derived from the ragweed pollen allergen Amb a 1, in particular from Amb a 1.3, consisting of an amino acid sequence selected from the group consisting of SEQ ID No. 12, SEQ ID No. 20, SEQ ID No. 27, SEQ ID No. 28, SEQ ID No. 30, SEQ ID No. 31, SEQ ID No. 33, SEQ ID No. 36, SEQ ID No. 37, SEQ ID No. 38, SEQ ID No. 39, SEQ ID No. 41, SEQ ID No. 42, SEQ ID No. 44, SEQ ID No. 46, SEQ ID No. 47, SEQ ID No. 48, SEQ ID No. 50, SEQ ID No. 51, SEQ ID No. 52, SEQ ID No. 53, SEQ ID No. 59, SEQ ID No. 60, SEQ ID No. 61, SEQ ID No. 67, SEQ ID No. 68, SEQ ID No. 69, SEQ ID No. 77, SEQ ID No. 78, SEQ ID No. 79, SEQ ID No. 80, SEQ ID No. 81, SEQ ID No. 83, SEQ ID No. 86, SEQ ID No. 87, SEQ ID No. 88, SEQ ID No. 89, SEQ ID No. 90, SEQ ID No. 91, SEQ ID No. 93, SEQ ID No. 94, SEQ ID No. 96, SEQ ID No. 97, SEQ ID No. 98, SEQ ID No. 99, SEQ ID No. 100, SEQ ID No. 101, SEQ ID No. 102, SEQ ID No. 107, SEQ ID No. 108, SEQ ID No. 109, SEQ ID No. 110, SEQ ID No. 111, SEQ ID No. 112, SEQ ID No. 114, SEQ ID No. 115, SEQ ID No. 118, SEQ ID No. 119, SEQ ID No. 120, SEQ ID No. 121, SEQ ID No. 122, SEQ ID No. 123, SEQ ID No. 124, SEQ ID No. 125, SEQ ID No. 126, SEQ ID No. 127, SEQ ID No. 128, SEQ ID No. 129, SEQ ID No. 130, SEQ ID No. 131, SEQ ID No. 132, SEQ ID No. 133, SEQ ID No. 134, SEQ ID No. 135, SEQ ID No. 136, SEQ ID No. 137, SEQ ID No. 138, SEQ ID No. 139 and functional equivalents thereof.

It turned out that the peptides of the present invention having an amino acid sequence selected from the group consisting of SEQ ID No. 12, SEQ ID No. 20, SEQ ID No. 27, SEQ ID No. 28, SEQ ID No. 30, SEQ ID No. 31, SEQ ID No. 33, SEQ ID No. 36, SEQ ID No. 37, SEQ ID No. 38, SEQ ID No. 39, SEQ ID No. 41, SEQ ID No. 42, SEQ ID No. 44, SEQ ID No. 46, SEQ ID No. 47, SEQ ID No. 48, SEQ ID No. 50, SEQ ID No. 51, SEQ ID No. 52, SEQ ID No. 53, SEQ ID No. 59, SEQ ID No. 60, SEQ ID No. 61, SEQ ID No. 67, SEQ ID No. 68, SEQ ID No. 69, SEQ ID No. 77, SEQ ID No. 78, SEQ ID No. 79, SEQ ID No. 80, SEQ ID No. 81, SEQ ID No. 83, SEQ ID No. 86, SEQ ID No. 87, SEQ ID No. 88, SEQ ID No. 89, SEQ ID No. 90, SEQ ID No. 91, SEQ ID No. 93, SEQ ID No. 94, SEQ ID No. 96, SEQ ID No. 97, SEQ ID No. 98, SEQ ID No. 99, SEQ ID No. 100, SEQ ID No. 101, SEQ ID No. 102, SEQ ID No. 107, SEQ ID No. 108, SEQ ID No. 109, SEQ ID No. 110, SEQ ID No. 111, SEQ ID No. 112, SEQ ID No. 114, SEQ ID No. 115, SEQ ID No. 118, SEQ ID No. 119, SEQ ID No. 120, SEQ ID No. 121, SEQ ID No. 122, SEQ ID No. 123, SEQ ID No. 124, SEQ ID No. 125, SEQ ID No. 126, SEQ ID No. 127, SEQ ID No. 128, SEQ ID No. 129, SEQ ID No. 130, SEQ ID No. 131, SEQ ID No. 132, SEQ ID No. 133, SEQ ID No. 134, SEQ ID No. 135, SEQ ID No. 136, SEQ ID No. 137, SEQ ID No. 138 and SEQ ID No. 139, show reactivity with T cells isolated from allergic individuals and, consequently, may be employed in the production of vaccines, especially vaccines for allergies caused by ragweed pollen allergens and allergies cross-reacting to ragweed pollen allergens. In particular the peptides having SEQ ID No. 52, SEQ ID No. 68, SEQ ID No. 86, SEQ ID No. 91 and SEQ ID No. 126 to SEQ ID No. 139 show high T cell reactivity with samples obtained from individuals suffering from ragweed pollen allergy.

A further advantage of the peptides of the present invention is that all of them lack IgE binding activity. Therefore, molecules comprising these peptides do not provoke allergic reactions (e.g. increased release of histamine) when administered to an individual.

For therapeutic purposes peptides derived from allergens do not bind IgE specific for Amb a 1 or bind such IgE to a substantially lesser extent (e.g. at least 100 fold less and more preferably, at least 1000 fold less binding) than the corresponding purified native Amb a 1 or the recombinantly produced beta chain of Amb a 1. If a peptide of the invention is to be used as a diagnostic reagent, it is not necessary that the peptide or protein has reduced IgE binding activity compared to the native Amb a 1 allergen. IgE binding activity of peptides can be determined by, for example, an enzyme linked immunosorbent assay (ELISA) using, for example, sera obtained from an individual (i.e. an allergic individual) that has been previously exposed to the native Amb a 1. Briefly, a peptide to be tested is coated onto wells of a microtiter plate. After washing and blocking the wells, antibody solution consisting of the serum or plasma of an allergic individual who has been exposed to the peptide being tested or the protein from which it was derived is incubated in the wells. The plasma is generally depleted of IgG before incubation. However, the depletion is not necessary if highly specific anti IgE-antibodies are used. Furthermore, allergic individuals who have not undergone specific immunotherapy have in some cases almost no detectable IgG antibodies specific for the allergen in question. A labelled secondary antibody is added to the wells and incubated. The amount of IgE binding is then quantified and compared to the amount of IgE bound by a purified native Amb a 1 protein. Alternatively, the binding activity of a peptide can be determined by Western blot analysis. For example, a peptide to be tested is run on a polyacrylamide gel using SDS-PAGE. The peptide is then transferred to nitrocellulose and subsequently incubated with sera from an allergic subject. After incubation with the labelled secondary antibody, the amount of IgE bound is then determined and quantified.

Another assay which can be used to determine IgE binding activity of a peptide is a competition ELISA assay. Briefly, an IgE antibody pool is generated by combining plasma or serum from ragweed pollen allergic individuals that have been shown by direct ELISA to have IgE reactive with native Amb a 1. This pool is used in ELISA competition assays to compare IgE binding to native Amb a 1 to the peptide tested. IgE binding for the native Amb a 1 protein and the peptide being tested is determined and quantified.

Furthermore, the peptides of the present invention do preferably not result in the release of mediators (e.g. histamines) from mast cells or basophils. To determine whether a peptide which binds IgE results in the release of mediators, a histamine release assay can be performed using standard reagents and protocols. Briefly, a buffered solution of a peptide to be tested is combined with an equal volume of whole heparinized blood from an allergic subject. After mixing and incubation, the cells are pelleted and the supernatants are processed and analyzed using, e.g., a radioimmunoassay to determine the amount of histamine released.

The molecule of the present invention may comprise in any combination more than one peptides of the present invention. These peptides may be conjugated chemically or fused by recombinant technology to each other. Such a molecule may comprise at least two, three, four, five, seven, ten, 15, 20, peptides.

The at least one peptide of the invention can be produced by recombinant DNA techniques in a host cell transformed with a nucleic acid having a sequence encoding such peptide. The isolated peptides of the invention can also be produced by chemical synthesis. Of course it is also possible to produce the peptides by chemical or enzymatic cleavage of the protein allergen.

When a peptide is produced by recombinant techniques, host cells transformed with a nucleic acid of the invention (or the functional equivalent of the nucleic acid having a sequence encoding the peptide (or functional equivalent of the peptide) are cultured in a medium suitable for the cells. Peptides can be purified from cell culture medium, host cells or both using techniques known in the art for purifying peptides and proteins including ion-exchange chromatography, gel filtration chromatography, ultrafiltration, electrophoresis or immunopurification with antibodies specific for the peptide. Isolated peptides of the invention are substantially free of cellular material or culture medium when produced by recombinant DNA techniques or substantially free of chemical precursors or other chemicals when synthesized chemically or free of other materials and reagents when produced by chemical or enzymatic cleavage.

The peptides of the present invention may also be modified by amino acid substitution, deletion or addition. Therefore, the peptides of the present invention comprise at least 7 amino acid residues of the amino acid sequences SEQ ID No. 1 to 139. Also within the present invention are peptides having more than 12 amino acid residues, whereby these additional residues may be derived from the native Amb a 1 molecule and being found adjacent to the peptide in the native Amb a 1 molecule, random amino acids or other peptides or proteins. However, these modified peptides (variants) exhibit similar or even identical properties as the unmodified peptides. In particular the immunogenic properties have to be substantially identical. This means that antibodies directed to these modified peptides are also able to bind to peptides having amino acid sequences SEQ ID No. 1 to 139.

As used herein, a "peptide" refers to an amino acid sequence having fewer amino acid residues than the entire amino acid sequence of the protein from which the peptide was derived. The term "peptide" also refers to any functional equivalents or variants of a peptide or to any fragments or portions of a peptide. "Functional equivalents" of a peptide include peptides having the same or enhanced ability to bind MHC, peptides capable of stimulating the same T cell subpopulations, peptides having the same or increased ability to induce T cell responses such as stimulation (proliferation or cytokine secretion), peptides having at least the same level of reduced IgE binding, and peptides which elicit at least the same minimal level of IgE synthesis stimulating activity as the peptides directly derived from Amb a 1. Minimal IgE stimulating activity refers to IgE synthesis stimulating activity that is less than the amount of IgE production elicited by a purified native ragweed pollen allergen. The peptides and functional equivalents thereof of the present invention consist preferably of 6 to 50, preferably 7 to 45, more preferably 8 to 40, even more preferably 9 to 35, in particular 10 to 30, amino acid residues. "Functional equivalents" of the peptides of the invention may further comprise at the C- and/or N-terminus of said peptides at least one further amino acid residue, which may serve as a linking group (e.g. cysteine) or which may can be found adjacent to the peptide in wild-type Amb a 1.

The term "variant" as used herein refers to an amino acid sequence that differs by one or more amino acid residues from another, usually related polypeptide. The variant may have "conservative" changes, wherein a substituted amino acid has similar structural or chemical properties. One type of conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (for example, replacement of a glycine with a tryptophan).

Similar minor variations may also include amino acid deletions or insertions, or both. Preferred variants of the peptides and molecules of the present invention have less than 10%, and preferably less than 5%, and still more preferably less than 2% changes (whether substitutions, deletions, and insertions).

Another aspect of the present invention relates to a peptide derived from the ragweed pollen allergen Amb a 1 and consisting of an amino acid sequence selected from the group consisting of SEQ ID No. 12, SEQ ID No. 20, SEQ ID No. 27, SEQ ID No. 28, SEQ ID No. 30, SEQ ID No. 31, SEQ ID No. 33, SEQ ID No. 36, SEQ ID No. 37, SEQ ID No. 38, SEQ ID No. 39, SEQ ID No. 41, SEQ ID No. 42, SEQ ID No. 44, SEQ ID No. 46, SEQ ID No. 47, SEQ ID No. 48, SEQ ID No. 50, SEQ ID No. 51, SEQ ID No. 52, SEQ ID No. 53, SEQ ID No. 59, SEQ ID No. 60, SEQ ID No. 61, SEQ ID No. 67, SEQ ID No. 68, SEQ ID No. 69, SEQ ID No. 77, SEQ ID No. 78, SEQ ID No. 79, SEQ ID No. 80, SEQ ID No. 81, SEQ ID No. 83, SEQ ID No. 86, SEQ ID No. 87, SEQ ID No. 88, SEQ ID No. 89, SEQ ID No. 90, SEQ ID No. 91, SEQ ID No. 93, SEQ ID No. 94, SEQ ID No. 96, SEQ ID No. 97, SEQ ID No. 98, SEQ ID No. 99, SEQ ID No. 100, SEQ ID No. 101, SEQ ID No. 102, SEQ ID No. 107, SEQ ID No. 108, SEQ ID No. 109, SEQ ID No. 110, SEQ ID No. 111, SEQ ID No. 112, SEQ ID No. 114, SEQ ID No. 115, SEQ ID No. 118, SEQ ID No. 119, SEQ ID No. 120, SEQ ID No. 121, SEQ ID No. 122, SEQ ID No. 123, SEQ ID No. 124, SEQ ID No. 125, SEQ ID No. 126, SEQ ID No. 127, SEQ ID No. 128, SEQ ID No. 129, SEQ ID No. 130, SEQ ID No. 131, SEQ ID No. 132, SEQ ID No. 133, SEQ ID No. 134, SEQ ID No. 135, SEQ ID No. 136, SEQ ID No. 137, SEQ ID No. 138 and SEQ ID No. 139.

Another aspect of the present invention relates to a molecule comprising at least one peptide of the present invention and at least one second peptide derived from an immunogen other than Amb a 1.

The molecule of the present invention may be conjugated, bound chemically or fused to one or more other peptides which are not derived from Amb a 1. Such a molecule may be employed, for instance, as a vaccine inducing an immune response against a ragweed pollen allergen peptide of the present invention and said second immunogen (e.g. of bacterial or viral origin).

In order to elicit antibodies against small molecules (hapten) like the peptides of the present invention these small molecules may be linked (e.g. conjugated) to a carrier. This linkage makes the hapten immunogenic, this means antibodies are generated after injection into an individual. The binding of the hapten to a carrier protein is often covalent, but it can be ionic or be effected through a chemical component bridging the hapten and the carrier. The carrier is typically a protein, but it can also contain sugar and fat in mono- or polymer form.

The immunogen according to the present invention is preferably an allergen, preferably selected from the group consisting of Amb a 2, Amb a 3, Amb a 5, Amb a 6, Amb a 7, Amb a 8, Amb a 9, Amb a 10, Amb t 5, Art v 1, Art v 2, Art v 3, Art v 4, Art v 5, Art v 6, Hel a 1, Hel a 2, Hel a 3, Mer a 1, Che a 1, Che a 2, Che a 3, Sal k 1, Cat r 1, Pla l 1, Hum j 1, Par j 1, Par j 2, Par j 3, Par o 1, Cyn d 1, Cyn d 7, Cyn d 12, Cyn d 15, Cyn d 22w, Cyn d 23, Cyn d 24, Dac g 1, Dac g 2, Dac g 3, Dac g 5, Fes p 4w, Hol l 1, Lol p 1, Lol p 2, Lol p 3, Lol p 5, Lol p 11, Pha a 1, Phl p 1, Phl p 2, Phl p 4, Phl p 5, Phl p 6, Phl p 11, Phl p 12, Phl p 13, Poa p 1, Poa p 5, Sor h 1, Pho d 2, Aln g 1, Bet v 1, Bet v 2, Bet v 3, Bet v 4, Bet v 6, Bet v 7, Car b 1, Cas s 1, Cas s 5, Cas s 8, Cor a 1, Cor a 2, Cor a 8, Cor a 9, Cor a 10, Cor a 11, Que a 1, Fra e 1, Lig v 1, Ole e 1, Ole e 2, Ole e 3, Ole e 4, Ole e 5, Ole e 6, Ole e 7, Ole e 8, Ole e 9, Ole e 10, Syr v 1, Cry j 1, Cry j 2, Cup a 1, Cup s 1, Cup s 3w, Jun a 1, Jun a 2, Jun a 3, Jun o 4, Jun s 1, Jun v 1, Pla a 1, Pla a 2, Pla a 3, Aca s 13, Blo t 1, Blo t 3, Blo t 4, Blo t 5, Blo t 6, Blo t 10, Blo t 11, Blo t 12, Blo t 13, Blo t 19, Der f 1, Der f 2, Der f 3, Der f 7, Der f 10, Der f 11, Der f 14, Der f 15, Der f 16, Der f 17, Der f 18w, Der m 1, Der p 1, Der p 2, Der p 3, Der p 4, Der p 5, Der p 6, Der p 7, Der p 8, Der p 9, Der p 10, Der p 11, Der p 14, Der p 20, Der p 21, Eur m 2, Eur m 14, Gly d 2, Lep d 1, Lep d 2, Lep d 5, Lep d 7, Lep d 10, Lep d 13, Tyr p 2, Tyr p 13, Bos d 2, Bos d 3, Bos d 4, Bos d 5, Bos d 6, Bos d 7, Bos d 8, Can f 1, Can f 2, Can f 3, Can f 4, Equ c 1, Equ c 2, Equ c 3, Equ c 4, Equ c 5, Fel d 1, Fel d 2, Fel d 3, Fel d 4, Fel d 5w, Fel d 6w, Fel d 7w, Cav p 1, Cav p 2, Mus m 1, Rat n 1, Alt a 1, Alt a 3, Alt a 4, Alt a 5, Alt a 6, Alt a 7, Alt a 8, Alt a 10, Alt a 12, Alt a 13, Cla h 2, Cla h 5, Cla h 6, Cla h 7, Cla h 8, Cla h 9, Cla h 10, Cla h 12, Asp fl 13, Asp f 1, Asp f 2, Asp f 3, Asp f 4, Asp f 5, Asp f 6, Asp f 7, Asp f 8, Asp f 9, Asp f 10, Asp f 11, Asp f 12, Asp f 13, Asp f 15, Asp f 16, Asp f 17, Asp f 18, Asp f 22w, Asp f 23, Asp f 27, Asp f 28, Asp f 29, Asp n 14, Asp n 18, Asp n 25, Asp o 13, Asp o 21, Pen b 13, Pen b 26, Pen ch 13, Pen ch 18, Pen ch 20, Pen c 3, Pen c 13, Pen c 19, Pen c 22w, Pen c 24, Pen o 18, Fus c 1, Fus c 2, Tri r 2, Tri r 4, Tri t 1, Tri t 4, Cand a 1, Cand a 3, Cand b 2, Psi c 1, Psi c 2, Cop c 1, Cop c 2, Cop c 3, Cop c 5, Cop c 7, Rho m 1, Rho m 2, Mala f 2, Mala f 3, Mala f 4, Mala s 1, Mala s 5, Mala s 6, Mala s 7, Mala s 8, Mala s 9, Mala s 10, Mala s 11, Mala s 12, Mala s 13, Epi p 1, Aed a 1, Aed a 2, Api m 1, Api m 2, Api m 4, Api m 6, Api m 7, Bom p 1, Bom p 4, Bla g 1, Bla g 2, Bla g 4, Bla g 5, Bla g 6, Bla g 7, Bla g 8, Per a 1, Per a 3, Per a 6, Per a 7, Chi k 10, Chi t 1-9, Chi t 1.01, Chi t 1.02, Chi t 2.0101, Chi t 2.0102, Chi t 3, Chi t 4, Chi t 5, Chi t 6.01, Chi t 6.02, Chi t 7, Chi t 8, Chi t 9, Cte f 1, Cte f 2, Cte f 3, Tha p 1, Lep s 1, Dol m 1, Dol m 2, Dol m 5, Dol a 5, Pol a 1, Pol a 2, Pol a 5, Pol d 1, Pol d 4, Pol d 5, Pol e 1, Pol e 5, Pol f 5, Pol g 5, Pol m 5, Vesp c 1, Vesp c 5, Vesp m 1, Vesp m 5, Ves f 5, Ves g 5, Ves m 1, Ves m 2, Ves m 5, Ves p 5, Ves s 5, Ves vi 5, Ves v 1, Ves v 2, Ves v 5, Myr p 1, Myr p 2, Sol g 2, Sol g 4, Sol i 2, Sol i 3, Sol i 4, Sol s 2, Tria p 1, Gad c 1, Sal s 1, Bos d 4, Bos d 5, Bos d 6, Bos d 7, Bos d 8, Gal d 1, Gal d 2, Gal d 3, Gal d 4, Gal d 5, Met e 1, Pen a 1, Pen i 1, Pen m 1, Pen m 2, Tod p 1, Hel as 1, Hal m 1, Ran e 1, Ran e 2, Bra j 1, Bra n 1, Bra o 3, Bra r 1, Bra r 2, Hor v 15, Hor v 16, Hor v 17, Hor v 21, Sec c 20, Tri a 18, Tri a 19, Tri a 25, Tri a 26, Zea m 14, Zea m 25, Ory s 1, Api g 1, Api g 4, Api g 5, Dau c 1, Dau c 4, Cor a 1.04, Cor a 2, Cor a 8, Fra a 3, Fra a 4, Mal d 1, Mal d 2, Mal d 3, Mal d 4, Pyr c 1, Pyr c 4, Pyr c 5, Pers a 1, Pru ar 1, Pru ar 3, Pru av 1, Pru av 2, Pru av 3, Pru av 4, Pru d 3, Pru du 4, Pru p 3, Pru p 4, Aspa o 1, Cro s 1, Cro s 2, Lac s 1, Vit v 1, Mus xp 1, Ana c 1, Ana c 2, Cit l 3, Cit s 1, Cit s 2, Cit s 3, Lit c 1, Sin a 1, Gly m 1, Gly m 2, Gly m 3, Gly m 4, Vig r 1, Ara h 1, Ara h 2, Ara h 3, Ara h 4, Ara h 5, Ara h 6, Ara h 7, Ara h 8, Len c 1, Len c 2, Pis s 1, Pis s 2, Act c 1, Act c 2, Cap a 1w, Cap a 2, Lyc e 1, Lyc e 2, Lyc e 3, Sola t 1, Sola t 2, Sola t 3, Sola t 4, Ber e 1, Ber e 2, Jug n 1, Jug n 2, Jug r 1, Jug r 2, Jug r 3, Ana o 1, Ana o 2, Ana o 3, Ric c 1, Ses i 1, Ses i 2, Ses i 3, Ses i 4, Ses i 5, Ses i 6, Cuc m 1, Cuc m 2, Cuc m 3, Ziz m 1, Ani s 1, Ani s 2, Ani s 3, Ani s 4, Arg r, Asc s 1, Car p 1, Den n 1, Hev b 1, Hev b 2, Hev b 3, Hev b 4, Hev b 5, Hev b 6.01, Hev b 6.02, Hev b 6.03, Hev b 7.01, Hev b 7.02, Hev b 8, Hev b 9, Hev b 10, Hev b 11, Hev b 12, Hev b 13, Hom s 1, Hom s 2, Hom s 3, Hom s 4, Hom s 5 and Trip s 1.

It is particularly preferred to fuse and/or conjugate the peptides of the present invention derived from ragweed pollen allergen Amb a 1 to other allergens or peptides derived from said allergens. Such a fusion protein/polypeptide/peptide or conjugate is useful when used in a vaccine or in diagnosis.

Another aspect of the present invention relates to a nucleic acid molecule encoding a peptide or a molecule according to the present invention.

The nucleic acid molecule of the present invention may be employed, e.g., for the recombinant production of the peptides/polypeptides/proteins encoded by said nucleic acid molecule. Furthermore, they may also be used for therapeutic aspects (e.g. gene therapy, cell therapy).

Another aspect of the present invention relates to a vector comprising a nucleic acid molecule according to the present invention.

The nucleic acid molecule of the present invention may be introduced into a vector. The vector may be used for the recombinant production of the peptides and molecules of the present invention or for therapeutic aspects.

"Vector", as used herein, refers to a plasmid, cosmid and viral and phage DNA. A plasmid comprising a nucleic acid molecule according to the present invention may contain next to said molecule, e.g., an origin of replication, selection markers (e.g. antibiotic resistance markers, auxotrophic markers), a multiple cloning site, a promoter region operably linked to said molecule and/or sequence stretches for the homologue integration of the vector or parts thereof into the genome of a host.

Preferably, the vector of the present invention further comprises a promoter operably linked to said nucleic acid molecule, thus resulting in an expression cassette.

The expression cassette of the present invention comprises a promoter and a nucleic acid molecule encoding for a peptide of the present invention. The promoter is preferably positioned at the 5'-end (upstream) of the nucleic acid molecule of the present invention. The promoter to be used in the expression cassette may be any one, provided that the promoter can be controlled by the respective host.

A further aspect of the present invention relates to a vaccine formulation comprising at least one molecule and/or at least one peptide according to the present invention.

The peptide and/or molecule of the present invention comprising at least one peptide derived from the ragweed pollen allergen Amb a 1 and consisting of an amino acid sequence selected from the group consisting of SEQ ID No. 1 to 139 can be used in a vaccine formulation. Since these peptides are able to provoke a T cell response against the ragweed pollen allergen Amb a 1 the vaccine formulation may be used for the desensitization, prevention or treatment of ragweed pollen allergies and allergies cross-reacting with ragweed pollen allergens (e.g. mugwort pollen). Due to the lack of IgE binding activity the peptides are in particular advantageous when used in a vaccine, because no or substantially no allergic reaction is provoked by said vaccine. The vaccine formulation of the present invention may comprise at least one, preferably at least two, more preferably at least three, peptides of the present invention.

Administration of the therapeutic compositions of the present invention to an individual to be desensitized can be carried out using known procedures at dosages and for periods of time effective to reduce sensitivity (i.e. reduce the allergic response) of the individual to the allergen. Effective amounts of the therapeutic compositions will vary according to factors such as the degree of sensitivity of the individual to Amb a 1, the age, sex and weight of the individual and the ability of the protein or fragment thereof to elicit an antigenic response in the individual. The active compound (i.e. protein or fragment thereof) may be administered in a convenient manner such as by injection (subcutaneous, intravenous, etc.), oral administration, inhalation, transdermal application, or rectal administration. Depending on the route of administration, the active compound may be coated within a material to protect the compound from the action of enzymes, acids and other natural conditions which may inactivate the compound (see below). For example, preferably about 0.05 μg-1000 μg, more preferably from about 0.1-100 μg of active compound (i.e. protein or fragment thereof) per dosage unit may be administered by injection. Dosage regimen may be adjusted to provide the optimum therapeutic response. For example, several divided doses may be administered daily or the dose may be proportionally reduced as indicated by the exigencies of the therapeutic situation.

Of course, it is also possible and in the scope of the present invention providing an antibody bound to a peptide or molecule according to the present invention which may also be used in vaccine formulations.

Antibodies according to the present invention include, but are not limited to, polyclonal, monoclonal, multispecific, humanized or chimeric antibodies, single chain antibodies, Fab fragments, F(ab') fragments and epitope-binding fragments of any of the above. Furthermore, antibodies are considered as being immunoglobulin molecules and immunologically active portions of immunoglobulin molecules, i.e., molecules that contain an antigen binding site that immunospecifically binds an antigen. The immunoglobulin molecules of the invention are preferably of the types IgG, IgM, IgD, IgA and IgY, class (e.g., IgG1, IgG2, IgG3, IgG4, IgA1 and IgA2) or subclass of immunoglobulin molecule.

Polyclonal antibodies can be prepared by administering a polypeptide of the invention, preferably using an adjuvant, to a non-human mammal and collecting the resultant antiserum. Improved titres can be obtained by repeated injections over a period of time. There is no particular limitation to the species of mammals which may be used for eliciting antibodies; it is generally preferred to use rabbits or guinea pigs, but horses, cats, dogs, goats, pigs, rats, cows, sheep, camels etc., can also be used. In the production of antibodies, a definite amount of immunogen of the invention is e.g. diluted with physiological saline solution to a suitable concentration and the resulting diluted solution is mixed with, e.g. complete Freund's adjuvant to prepare a suspension or with mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. The suspensions and mixtures are administered to mammals, e.g. intraperitoneally, e.g. to a rabbit, using from about 50 μg to about 2500 μg polypeptide of the invention per administration. The suspension is preferably administered about every two weeks over a period of up to about 2-3 months, preferably about 1 month, to effect immunization. Antibody is recovered by collecting blood from the immunized animal after the passage of 1 to 2 weeks subsequently to the last administration, centrifuging the blood and isolating serum from the blood.

Monoclonal antibodies may e.g. be of human or murine origin. Murine monoclonal antibodies may be prepared by the method of Köhler and Milstein (Köhler, G. and Milstein, C., Nature 256 (1975) 495), e.g. by fusion of spleen cells of hyperimmunized mice with an appropriate mouse myeloma cell line.

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567 and 4,816,397.

Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modelling of the interactions of the CDR and framework residues to identify framework residues important for antigen binding and sequence comparison to identify unusual framework residues at particular positions (see, e.g., Queen et al., U.S. Pat. No. 5,585,089; Riechmann et al., Nature 332: 323 (1988)). Antibodies can be humanized using a variety of techniques known in the art including, for example, CDR-grafting (EP 239,400; WO 91/09967; U.S. Pat. Nos. 5,225, 539; 5,530,101; and 5,585,089), veneering or resurfacing (EP 592,106; EP 519,596; Padlan, Molecular Immunology 28 (4/5):489-498 (1991); Studnicka et al., Protein Engineering 7(6):805-814 (1994); Roguska. et al., PNAS 91:969-913 (1994)), and chain shuffling (U.S. Pat. No. 5,565,332).

The antibodies according to the present invention may advantageously be used for passive immunisation of an individual suffering from an allergy, in particular from house dust mite allergy. For passive immunisation the antibody is preferably an IgG or a derivative thereof (e.g. chimeric or humanized antibody). Furthermore this antibody may also be used for desensibilisation of an individual.

The vaccine formulation of the present invention further comprises at least one pharmaceutical acceptable adjuvant, excipient and/or carrier.

Pharmaceutically acceptable carriers preferably used are physiological saline, vegetable oils, mineral oil, aqueous sodium caroboxymethyl cellulose or aqueous polyvinylpyrrolidone. Suitable adjuvants include, but are not limited to: surface active substances, e.g., hexadecylamine, octadecylamine, octadecyl amino acid esters, lysolecithin, dimethyldioctadecylammonium bromide, methoxyhexadecylgylcerol, and pluronic polyols; polyamines, e.g., pyran, dextransulfate, poly IC, carbopol; peptides, e.g., muramyl dipeptide, dimethylglycine, tuftsin; oil emulsions; and mineral gels, e.g., aluminum hydroxide, aluminum phosphate, etc. and immune stimulating complexes. The adjuvant may be, for example, alum or a composition containing a vegetable oil, isomannide monooleate and aluminum mono-stearate. Other preferred adjuvants include microparticles or beads of biocompatible matrix materials. The molecules of the present invention may be incorporated into microparticles or microcapsules to prolong the exposure of the antigenic material to the individual and hence protect said individual against infection for long periods of time. The immunogen may also be incorporated into liposomes or conjugated to polysaccharides and/or other polymers for use in a vaccine formulation.

Also part of this invention is a composition that comprises the molecules, in particular the peptides, of this invention and a carrier, preferably a biologically-acceptable carrier, and more preferably a pharmaceutically-acceptable carrier. Typical carriers are aqueous carriers such as water, buffered aqueous solutions, aqueous alcoholic mixtures, and the like. Compositions comprising carriers that are for pharmaceutical use, particularly for use in humans, comprise a carrier that is pharmaceutically-acceptable. Examples of such carriers are known in the art.

Typically, such vaccines are prepared as injectables: either as liquid solutions or suspensions, solid forms suitable for solution in, or suspension in, liquid prior to injection may also be prepared. The vaccine may be administered to a target animal by any convenient route, such as subcutaneously, intraperitoneally, intramuscularly, intradermally, intravenously, orally, intranasally or intramammarilyi, in the presence of a physiologically acceptable diluent. The antigens may be administered in a single dose or in a plurality of doses. The vaccine of the present invention may be stored under refrigeration or in frozen or lyophilized form. The vaccine is administered to an individual in an amount effective to elicit a protective immune response as compared to a control. The effective amount will vary, e.g., with the age and size and may be readily determined by the practitioner skilled in the art. Suitable regimes for initial administration and booster shots will also be variable, but may be typified by an initial administration followed by subsequent inoculations or other administrations.

The vaccine formulation of the present invention contains at least one molecule comprising a peptide selected from the group consisting of SEQ ID No. 12, SEQ ID No. 20, SEQ ID No. 27, SEQ ID No. 28, SEQ ID No. 30, SEQ ID No. 31, SEQ ID No. 33, SEQ ID No. 36, SEQ ID No. 37, SEQ ID No. 38, SEQ ID No. 39, SEQ ID No. 41, SEQ ID No. 42, SEQ ID No. 44, SEQ ID No. 46, SEQ ID No. 47, SEQ ID No. 48, SEQ ID No. 50, SEQ ID No. 51, SEQ ID No. 52, SEQ ID No. 53, SEQ ID No. 59, SEQ ID No. 60, SEQ ID No. 61, SEQ ID No. 67, SEQ ID No. 68, SEQ ID No. 69, SEQ ID No. 77, SEQ ID No. 78, SEQ ID No. 79, SEQ ID No. 80, SEQ ID No. 81, SEQ ID No. 83, SEQ ID No. 86, SEQ ID No. 87, SEQ ID No. 88, SEQ ID No. 89, SEQ ID No. 90, SEQ ID No. 91, SEQ ID No. 93, SEQ ID No. 94, SEQ ID No. 96, SEQ ID No. 97, SEQ ID No. 98, SEQ ID No. 99, SEQ ID No. 100, SEQ ID No. 101, SEQ ID No. 102, SEQ ID No. 107, SEQ ID No. 108, SEQ ID No. 109, SEQ ID No. 110, SEQ ID No. 111, SEQ ID No. 112, SEQ ID No. 114, SEQ ID No. 115, SEQ ID No. 118, SEQ ID No. 119, SEQ ID No. 120, SEQ ID No. 121, SEQ ID No. 122, SEQ ID No. 123, SEQ ID No. 124, SEQ ID No. 125, SEQ ID No. 126, SEQ ID No. 127, SEQ ID No. 128, SEQ ID No. 129, SEQ ID No. 130, SEQ ID No. 131, SEQ ID No. 132, SEQ ID No. 133, SEQ ID No. 134, SEQ ID No. 135, SEQ ID No. 136, SEQ ID No. 137, SEQ ID No. 138 and SEQ ID No. 139.

In a particular preferred embodiment of the present invention the vaccine formulation comprises at least one peptide selected from the group consisting of SEQ ID No. 52, SEQ ID No. 68, SEQ ID No. 86, SEQ ID No. 91, and SEQ ID No. 126-SEQ ID No. 139, wherein a further preferred embodiment of the formulation comprises at least one peptide consisting of an amino acid sequence selected from the group consisting of SEQ ID No. 52 and SEQ ID No. 137 to 139. In particular, these molecules show a high T cell reactivity in patients suffering from ragweed allergy (the peptides are recognized by more than 90% of allergic individuals sensitized to ragweed allergies). Furthermore, these molecules/peptides may be formulated alone or in any combination in one single formulation. Thus the vaccine formulation may comprise at least two, preferably at least three, of the peptides selected from the group consisting of SEQ ID No. 52, SEQ ID No. 68, SEQ ID No. 86, SEQ ID No. 91, and SEQ ID No. 126-SEQ ID No. 139, preferably selected from the group consisting of SEQ ID No. 52 and SEQ ID No. 137 to 139. Particular preferred combinations of the peptides are: SEQ ID No. 52 and SEQ ID No. 137; SEQ ID No. 52 and SEQ ID No. 138; SEQ ID No. 52 and SEQ ID No. 139; SEQ ID No. 137 and SEQ ID No. 138; SEQ ID No. 137 and SEQ ID No. 139; SEQ ID No. 52, SEQ ID No. 137 and SEQ ID No. 138; SEQ ID No. 52, SEQ ID No. 138 and SEQ ID No. 139; SEQ ID No. 52, SEQ ID No. 137 and SEQ ID No. 139; SEQ ID No. 137, SEQ ID No. 138 and SEQ ID No. 139; SEQ ID No. 52, SEQ ID No. 137, SEQ ID No. 138 and SEQ ID No. 139.

Yet another aspect of the present invention relates to the use of a peptide and/or a molecule according to the present invention for the manufacture of a vaccine formulation as outlined above.

The vaccine formulation is used for preventing or treating a ragweed pollen allergy in an individual, in particular an allergy caused by Amb a 1, or an allergy cross-reacting with a ragweed pollen allergy.

Another aspect of the present invention relates to the use of a molecule as disclosed herein for diagnosing a ragweed allergy in an individual or the sensitivity of an individual to a ragweed pollen allergen, in particular to Amb a 1.

The molecules of the present invention, in particular the peptides of the present invention, may be used also for diagnostic purposes. Molecules and peptides of the present invention can be used for detecting and diagnosing ragweed allergy or an allergy cross-reacting with Amb a 1. For example, this could be done by combining blood or blood products obtained from an individual to be assessed for sensitivity to ragweed allergy with an isolated antigenic peptide or peptides of Amb a 1 or isolated Amb a 1 alpha or beta chain, under conditions appropriate for binding components in the blood (e.g., antibodies, T-cells, B-cells) with the peptide(s) or protein and determining the extent to which such binding occurs. Other diagnostic methods for allergic diseases which the peptides of the present invention can be used include radio-allergensorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays and IgE immunoblots.

A further aspect of the present invention relates to a method for diagnosing the sensitivity of an individual to a ragweed pollen allergen, in particular to Amb a 1, comprising the steps:
  providing a sample of an individual containing mast cells or basophils and/or antibodies, in particular antibodies of the IgE class,
  contacting said sample with a molecule/peptide according to the present invention
  determining the amount of histamine released from the mast cells or basophils upon contact with said molecule and/or determining the amount of ragweed pollen allergen specific antibodies in the sample, and
  diagnosing the sensitivity of an individual to a ragweed pollen allergen, in particular to Amb a 1, if the amount of histamine released and/or the amount of ragweed pollen allergen specific antibodies in the sample is increased compared to a sample obtained from an individual not suffering from a ragweed pollen allergy or an allergy exhibiting cross-reactivity with ragweed pollen allergy.

The sample used in the method according to the present invention is preferably a blood, tear, saliva or nasal secretion sample.

Further aspects of the present invention relate to the isolated alpha chain of Amb a 1.3 consisting of amino acid sequence SEQ ID No. 142 (PILRQASGD TINVAGSSQI WIDHCSLSKS FDGLVDVTLG STHVTISNCK FTQQS-KAILL GADDTHVQDK GMLATVAFNM FTDN-VDQRMP RCRFGFFQVV NNNYDRWGTY AIGGSSAPTI LCQGNRFLAP DDQIKKNVLA RTGT-GAAESM AWNWRSDKDL LENGAIFVTS GSDPVLT-PVQ SAGMIPAEPG EAAIKLTSSA GVLSCRPGAP C) or SEQ ID No. 143 (VLPGGMIKSN DGPPILRQAS DGDT-INVAGS SQIWIDHCSL SKSFDGLVDV TLGSTHVTIS NCKFTQQSKA ILLGADDTHV QDKGMLATVA FNM-FTDNVDQ RMPRCRFGFF QVVNNNYDRW GTYAIGGSSA PTILCQGNRF LAPDDQIKKN VLART-GTGAA ESMAWNWRSD KDLLENGAIF VTSGSDPVLT PVQSAGMIPA EPGEAAIKLT SSAGVLSCRP GAPC) and to an isolated beta chain of Amb a 1.3 consisting of amino acid sequence SEQ ID No. 144 (AEGVGEILPS VNETRSLQAC EAYNIIDKCW RGKADWENNR QALADCAQGF AKG-TYGGKWG DVYTVTSNLD DDVANPKEGT LRFAAAQNRP LWIIFKNDMV INLNQELVVN SDK-TIDGRGV KVEIINGGLT LMNVKNIIIH NINIHDVKVL PGGMIKSNDG P) or SEQ ID No. 145 (AEGVGEILPS VNETRSLQAC EAYNIIDKCW RGKADWENNR QAL-ADCAQGF AKGTYGGKWG DVYTVTSNLD DDVANP-KEGT LRFAAAQNRP LWIIFKNDMV INLNQELVVN SDKTIDGRGV KVEIINGGLT LMNVKNIIIH NINIH-DVK).

Amb a 1 can substantially be divided into two fragments, an alpha chain (SEQ ID No. 142 or SEQ ID No. 143) and a beta chain (SEQ ID No. 144). It surprisingly turned out that both chains exhibit different immunological properties. Whilst the alpha chain of Amb a 1 shows low IgE reactivity the beta chain contains most of the IgE epitopes of Amb a 1.

Yet another aspect of the present invention relates to a pharmaceutical preparation comprising an isolated alpha chain of Amb a 1.3 and/or an isolated beta chain of Amb a 1.3 according to the present invention.

Another aspect of the present invention relates to the use of an isolated alpha chain of Amb a 1.3 and/or an isolated beta chain of Amb a 1.3 according to the present invention for the manufacture of a medicament for the treatment of a ragweed pollen allergy in an individual, in particular an allergy caused by Amb a 1, or an allergy cross-reacting with a ragweed pollen allergy.

A further aspect of the present invention relates to the use of an isolated alpha chain of Amb a 1.3 and/or an isolated beta chain of Amb a 1.3 according to the present invention for diagnosing a ragweed allergy in an individual or the sensitivity of an individual to a ragweed pollen allergen, in particular to Amb a 1, or an allergy cross-reacting with a ragweed pollen allergy.

The present invention is further illustrated by the following figures and examples, however, without being restricted thereto.

FIG. 1 shows the purification of rAmb a 1.3 with Nickel Chelate Chromtography (NCC) in 8 M Urea. Samples were analyzed with SDS-PAGE/Coomassie staining. Purified fractions showed extensive aggregation.

FIG. 2 shows IgE dot-blot analysis of recombinant Amb a 1.3. *E. coli*-produced rAmb a 1.3 was purified as described above and dotted on nitrocellulose membranes. Sera from 17 ragweed pollen allergic patients (1-17) were tested and showed very weak or no IgE reactivity with rAmb a 1.3. The same patients showed strong IgE reactivity with nAmb a 1.

FIG. 3 shows TCL stimulated with purified natural Amb a 1 or rAmb a 1.3 at different concentrations. The values of the optimum concentrations are shown. N=13; Pearson correlation coefficient: 0.979  ($p<0.01$) or Spearman's rho: 0.912.

FIG. 5 shows similar cytokine production induced by ragweed extract and rAmb a 1.3 in TCL.

FIG. 7 shows TCL induced with natural or rAmb a 1.3 recognize similar T cell epitopes.

FIG. 8 shows relevant T cell activating regions of Amb a 1.3. Percentage of patients recognizing each epitope was separately analyzed for stimulation indexes higher than 3 (SI>3) and 5 (SI>5), respectively.

FIG. 9 shows an IgE immunoblot of purified nAmb a 1. nAmb a 1 was separated by SDS-PAGE, and electroblotted onto PVDF membrane. Membrane strips were incubated with sera from ragweed pollen allergic patients (lanes 1-29) or with serum from a non-allergic donor (lane C). Bound IgE was detected with $^{125}$I-labeled goat anti-human IgE. Ragweed pollen-sensitized patients were recruited in Austria (lanes 1-13) or in Italy (lanes 14-29).

Figures 2, 10:
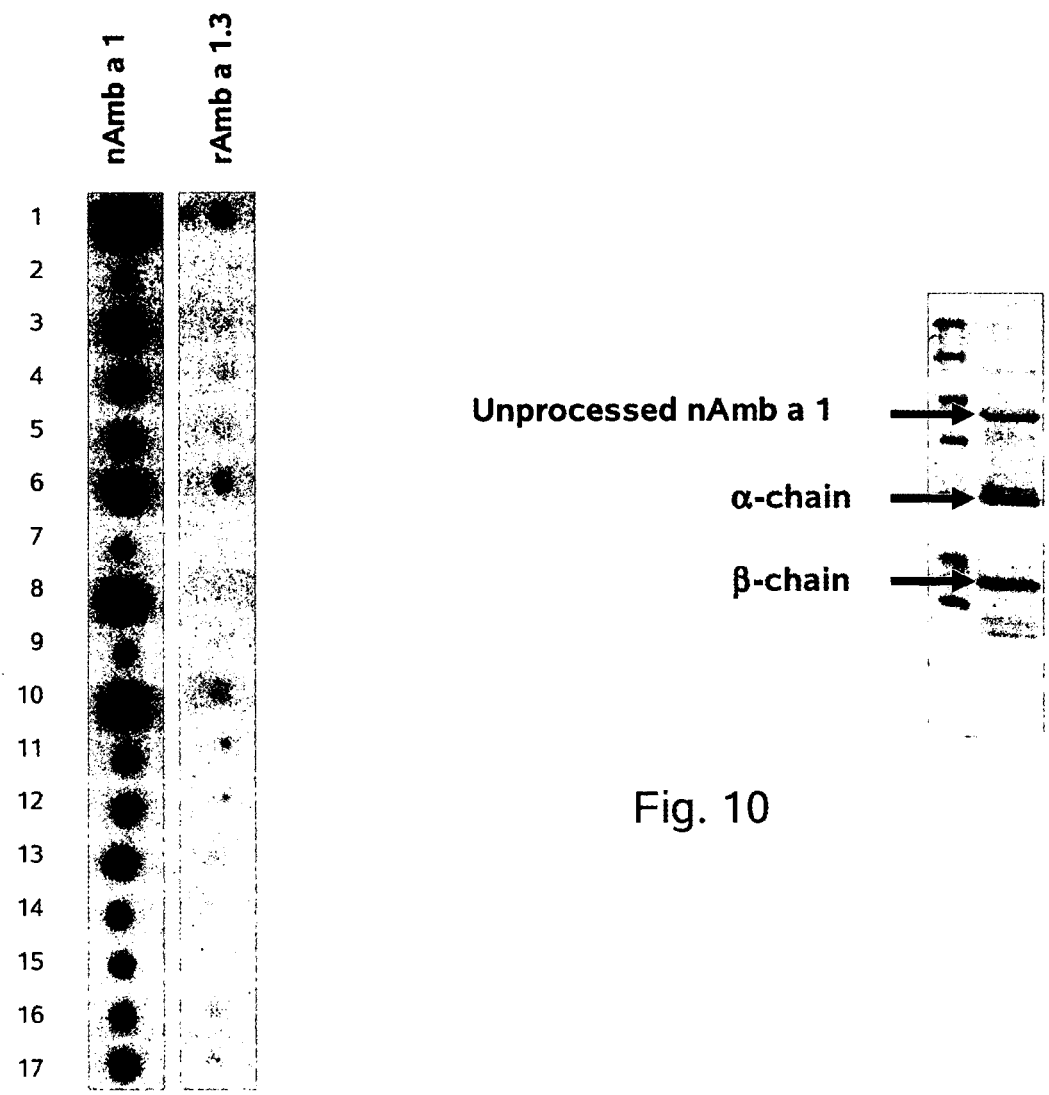

FIG. 10 shows a Coomassie staining of purified natural Amb a 1 after SDS-PAGE and electroblotting onto a PVDF membrane. The bands corresponding to unprocessed nAmb a 1, alpha and beta chains were subjected to Edman-degradation to obtain the N-terminal sequences.

FIG. 11 shows the N-terminal sequence of unprocessed natural Amb a 1 (nAmb a 1, see FIG. 10) and alignment with deduced amino acid sequences of Amb a 1 isoforms.

FIG. 12 shows the N-Terminal sequence of natural Amb a 1 (nAmb a 1, see FIG. 10) alpha chain and alignment with deduced amino acid sequences of Amb a 1 isoforms.

FIG. 13 shows the N-terminal sequence of natural Amb a 1 (nAmb a 1, see FIG. 10) beta chain and alignment with deduced amino acid sequences of Amb a 1 isoforms.

FIG. 14 shows deduced amino acid sequences of Amb a 1 isoforms and their putative alpha and beta chains. Isoforms Amb a 1.1, Amb a 1.2, Amb a 1.3, Amb a 1.4 and Amb a 2 were published (Rafnar et al., J. Biol. Chem. 266: 1229-1236, 1991) and patented (U.S. Pat. No. 5,776,761). The R2 clone was isolated in the laboratory by immunoscreening of a ragweed pollen cDNA pollen with anti-Amb a 1 affinity purified rabbit antibodies and is identical to Amb a 1.3 at the protein level. Letters underlined, predicted signal peptide using the algorithm SignalP (http://www.cbs.dtu.dk/services/SignalP/). In italicised letters, putative beta chain sequence based on N-terminal sequencing and mass measurement of natural Amb a 1. Italicised and underlined, putative alpha chain sequence based on N-terminal sequencing and mass measurement of natural Amb a 1 (FIGS. 10-13; Table 4). N-terminal sequence analysis showed that sequences in bold letters were proteolytically removed in the purified natural Amb a 1 preparation.

FIG. 15 shows a sequence alignment of Amb a 1 isoforms. Amb a 1.1, Amb a 1.2, Amb a 1.3, and Amb a 2 were previously cloned, sequenced and published (Rafnar et al., J. Biol. Chem. 266: 1229-1236, 1991). Sequence alignment was generated using the software Clustalw (http://npsa-pbil.ibcp.fr/cqi-bin/npsa_automat.pl?page=npsa_clustalw.html). The complete deduced amino acid sequences (including signal peptide) given in FIG. 14 were used for the alignment.

FIG. 16 shows deduced amino acid sequence of Amb a 1.3 (R2 clone) and chains. (a) Putative alpha and beta chains based on the information from N-terminal sequencing and mass spectrometry of purified natural Amb a 1 (see FIGS. 10-13; Table 4). (b) the first construct made in the lab to produce recombinant alpha and beta chains of Amb a 1.3. The expression of the chains was better than full-length Amb a 1.3 but low yields were obtained. In addition, the alpha chain excluded an important T cell reactive domain (boxed, aa 178-189). (c) modified (version 1) alpha and beta chains of Amb a 1.3 designed to include in the alpha chain the T cell epitope corresponding to amino acids 178-189. (d) modified (version 2) alpha and beta chains of Amb a 1.3 designed to include in the alpha chain the T cell epitope corresponding to amino acids 178-189 and to exclude in the beta chain the first 20 amino acids at the N-terminus, which were shown to be proteolytically removed in natural Amb a 1.

Figure 17:
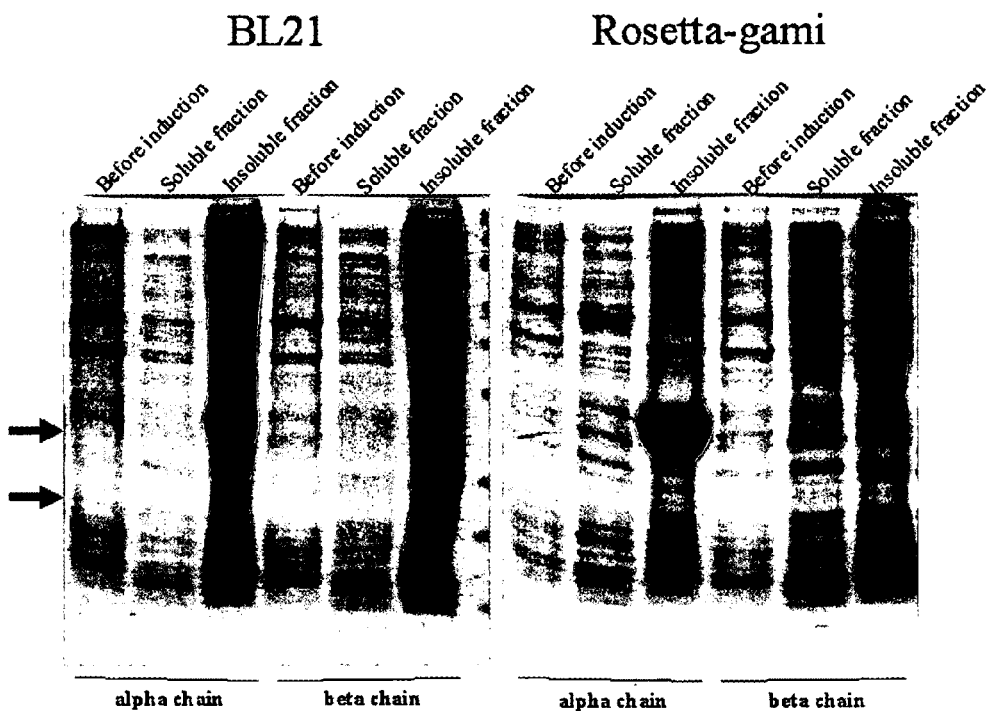

FIG. 17 shows the expression of Amb a 1.3 modified (version 1) alpha and beta chains in *E. coli* strains BL21 and Rosetta-gami B (DE3) pLysS.

Figure 18:
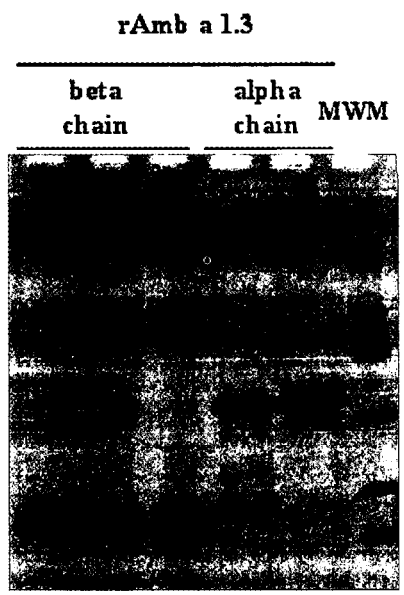

FIG. 18 shows SDS-PAGE and Coomassie staining of modified (version 1) Amb a 1.3 alpha and beta chains after affinity purification on nickel column. High yields of modified alpha and beta chains were obtained using *E. coli* strain Rosetta-gami B (DE3) pLysS (Novagen). The purified chains were soluble and did not show any tendency to aggregate, which was an acute problem with the full-length Amb a 1.3 allergen.

Figure 19:
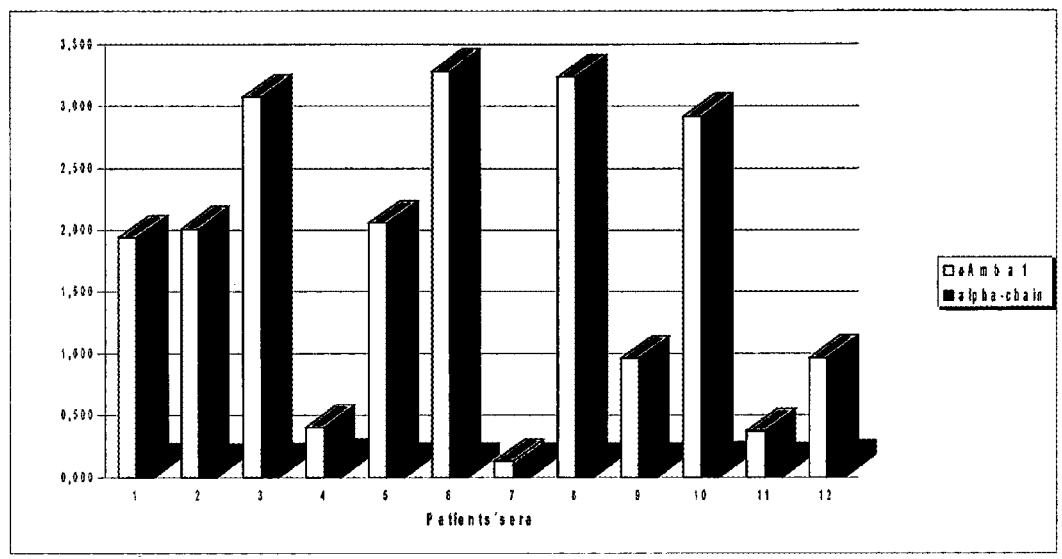

FIG. 19 shows Human IgE ELISA of purified natural Amb a 1 and modified (version 1) alpha chain of Amb a 1.3

Figure 20:
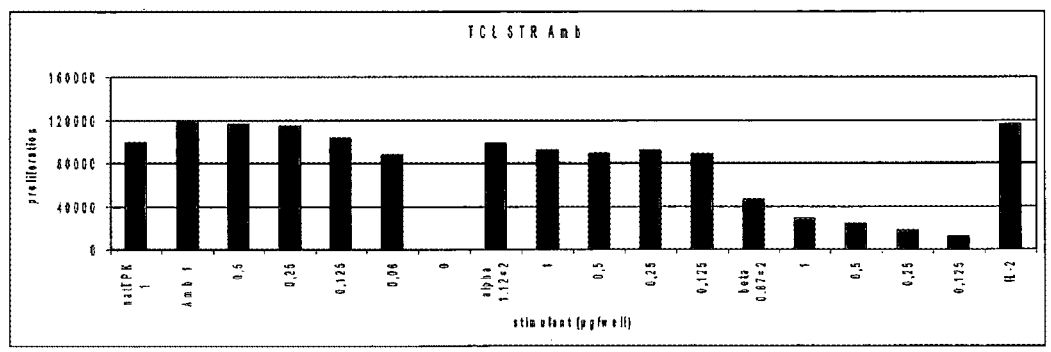

FIG. 20 shows proliferation of an Amb a 1-specific TCL with modified (version 1) alpha and beta chains of Amb a 1.3. Natural Amb a 1, different concentrations of full-length rAmb a 1.3, rAlpha and beta chains were used as stimulants. TCL was initiated with rAmb a 1.3 (Amb).

FIG. 21 shows proliferative responses of 2 Amb a 1-specific TCL using full-length rAmb a 1.3, and modified (version 1) alpha and beta chains of Amb a 1.3. TCL were initiated either with rAmb a 1.3 (Amb) or with ragweed pollen extract (RW).

FIG. 22 shows 26 identified relevant T cell activating regions in Amb a 1.3. 17/26 epitopes are located in the C-terminal region of Amb a 1. Therefore the alpha and beta chains were designed to include these relevant T cell epitopes.

EXAMPLES

Example 1

Isolation of a cDNA Coding for Amb a 1

Example 1.1

Affinity Purification of Rabbit Anti-Amb a 1 Antibodies

Sera from rabbits immunized with natural Amb a 1 can be obtained by general methods known in the art. For screening the ragweed pollen cDNA library, Amb a 1-specific antibodies were purified by affinity chromatography. 5 mg of natural Amb a 1 purified from ragweed pollen was coupled to CNBr-activated Sepharose (GE Healthcare Life Sciences). After binding of the rabbit sera, the resin was washed and highly specific Amb a 1-specific antibodies were eluted with 0.2 M glycine, pH 2.8. The antibodies were immediately neutralized and dialyzed against 1×PBS pH 7.4 (8 g NaCl, 0.2 g KCl, 1.44 g Na$_2$HPO$_4$, 0.24 g KH$_2$PO$_4$, adjust with HCl to pH 7.4). Purified antibodies were then used for immunoblotting and library screening experiments.

Example 1.2

Construction and Immunoscreening of a Ragweed Pollen cDNA Library

A ragweed pollen cDNA library was constructed in the lambda ZAP II vector (Stratagene). Purified rabbit anti-Amb a 1-antibodies were used to screen 400.000 plaques of the ragweed pollen cDNA library. Four positive Amb a 1 clones were isolated and used for in vivo excision of pBluescript phagemid from the Uni-ZAP XR vector. The clones designated R1, R2, R3 and R4 were selected for DNA sequence analysis, which was carried out by the "primer walking" technique using 4 and 5 primers including the flanking primers T7 and T3. R1 and R4 were truncated at their 3' and 5' ends, respectively, and therefore were not further used in the present experiments. Both strands of R2 and R3 were sequenced twice. The sequences were used for similarity searches in the Database.

Example 1.3

Cloning into Expression Vector pHis-Parallel-2

The R2 (Amb a 1.3) cDNA was ligated into the vector pHis-parallel-2. For the cloning procedure two flanking cloning primers were constructed. The complete cDNA sequence was truncated at the 5' end by 75 nucleotides coding for the putative signal peptide. The following primers were used: Rag-Nco-forward: 5'-GAGAGAGACCATGGC-CGAAGGGGTCGG-AGAAATCTTACCTTCAG-3' (SEQ ID No. 140) and Rag-Xho-reverse: 5'-GAGAGAGACTC-GAGTTAGCAAGGTGCTCCAGGACGGCATGAG-3' (SEQ ID No. 141). Nco I and Xho I restriction sites were introduced at the 5' and 3' ends. The polymerase chain reaction (PCR) products were digested with Nco I and Xho I restriction enzymes (New England Biolabs) and ligated to the respective sites of the vector pHis-parallel-2. The resulting pHis-parallel-2/R2 construct was sequenced according to the Dye Terminator Cycle Sequencing protocol (Applied Biosystems).

Example 1.4

Expression of Recombinant R2 (Amb a 1.3) in *Escherichia coli*

Recombinant protein expression was performed using competent *Escherichia coli* strain BL21 DE3 (Stratagene) hosting the construct pHis-Parallel-2/R2 (for Amb a 1.3). The transformants were selected on LB plates containing 100 mg/L ampicillin and single transformant colonies were picked. Several small-scale expression experiments were carried out and optimized before attempting a large-scale protein production. The culture medium (10 g/L peptone, 5 g/L yeast extract, 10 g/L glycerol, 5 g/L NaCl, 2.5 g/L $(NH_4)_2SO_4$, 0.5 g/L $MgSO_4.7H_2O$ and 1.8 g/L $Na_2HPO_4.2H_2O$, pH adjusted to 7.4) was inoculated with 3% of an overnight culture, grown in culture medium with 150 µg/mL penicillin G (Biochemie). Fermentation was carried out in a 10 L Bioflow 3000 Fermenter (New Brunswick Scientific Co.) at 37° C. with 7% oxygen saturation 200-400 rpm agitation and induction with 0.4 mM IPTG at an $OD_{600}$ of 1.0. Bacterial cells (60-80 g wet cell weight from 10 L culture) were harvested by centrifugation 3 hours post induction and resuspended in 100 mL 50 mM Tris base, 1 mM EDTA, 0.1% Triton X-100 (pH unadjusted, 5 mL/g cells). After addition of freshly dissolved lysozyme (100 µg/g cells) and incubation at room temperature for 1 hour, the cells were lysed by 3 freeze-thaw cycles. Separation of the soluble fraction was done by centrifugation and the raw inclusion bodies were washed two to three times with 1% Triton X-100, 20 mM Tris-HCl pH 8.0, 1 mM EDTA, followed by 2 washes with 50% ethanol, 20 mM Tris-HCl pH 8.0. Purified inclusion bodies were dissolved in 500 mL 8 M urea, 0.5 M NaCl, 20 mM Tris-HCl pH 8.0.

Example 1.5

Purification of Recombinant R2 (Amb a 1.3) Allergen

The solution was loaded on a 150 mL Chelating Cellufine Column (Millipore) pre-equilibrated with the buffer described in the last step, after charging it with $NiCl_2$ according to the manufacturers' instructions. All chromatography steps were carried out on a Biopilot FPLC system (GE Healthcare Life Sciences). Bound protein was eluted with a linear imidazole gradient ranging from 0-300 mM. The purity of the fractions was analyzed by conventional SDS-PAGE. Fractions containing nearly pure Amb a 1.3 were stabilized with 2 mM EDTA and prepared for the following gel filtration step by concentration to a volume of 50 mL in a Vivaflow 50 ultrafiltration cell (Vivascience). Gel filtration was performed in 8 M urea, 0.5 M NaCl, 20 mM Tris-HCl pH 8.0, 2 mM EDTA on a Sephacryl S-200 HR (GE Healthcare Life Sciences) column (dimensions 50×1000 mm). Pure Amb a 1 fractions were again concentrated to a protein concentration of approximately 3 mg/mL by ultrafiltration. Before lyophilization a refolding procedure was performed, in which disulfide bonds were reduced by addition of 10 mM mercaptoethanol and re-oxidized during subsequent dialysis against the 1,000-2,000-fold volume of 5 mM $NH_4HCO_3$ at 4° C.

Example 1.6

SDS-PAGE and Immunoblot Analysis of the Purified Recombinant Amb a 1.3

The proteins were analyzed via SDS-PAGE using 15% acrylamide gels and 0.1% Coomassie staining with a molecular weight standard RPN 756 (GE Healthcare Life Sciences). Sera from allergic patients were tested for positive IgE-reactivity. rAmb a 1 and rArt v 6 were separated on 15% (w/w) polyacrylamide gels and electroblotted onto a PVDF membrane. After blocking the non-specific protein binding sites with Blocking buffer (per L: 7.5 g $Na_2HPO_4$, 1 g $NaH_2PO_4$, 5 g BSA and 5 mL Tween 20), the membrane was incubated with patients' sera (diluted 1:10 in Blocking buffer) for more than 6 hours at room temperature. The membrane was washed for at least 30 minutes with Blocking buffer before it was incubated with radiolabeled [$^{125}$I]-anti human IgE (RAST, 5 ☐Ci, MedPro) diluted in Blocking buffer (1:40) overnight at room temperature. After a second 30-minute wash, the membrane was placed onto an imaging plate. The screen was exposed for at least 24 hours and developed using a Phospho-Imager Bas-1800 II scanner for detection and the instrument's supporting software (Fujifilm).

Example 1.7 cDNa Clones Coding for Amb a 1 Isoforms

The R2 and R3 clones isolated from the ragweed pollen library were complete and coded for Amb a 1 isoforms. The deduced amino acid sequence of R3 differed from the mature Amb a 1.1 isoform in one amino acid: glycine at position 50 of mature Amb a 1.1 is exchanged for an alanine in R3. The deduced amino acid sequence of R2 is identical to Amb a 1.3 isoform. The R2 clone was used for all experiments described here and will be referred to as Amb a 1.3.

Example 1.8

Recombinant Production and IgE Binding Activity of Amb a 1.3

Figure 1:
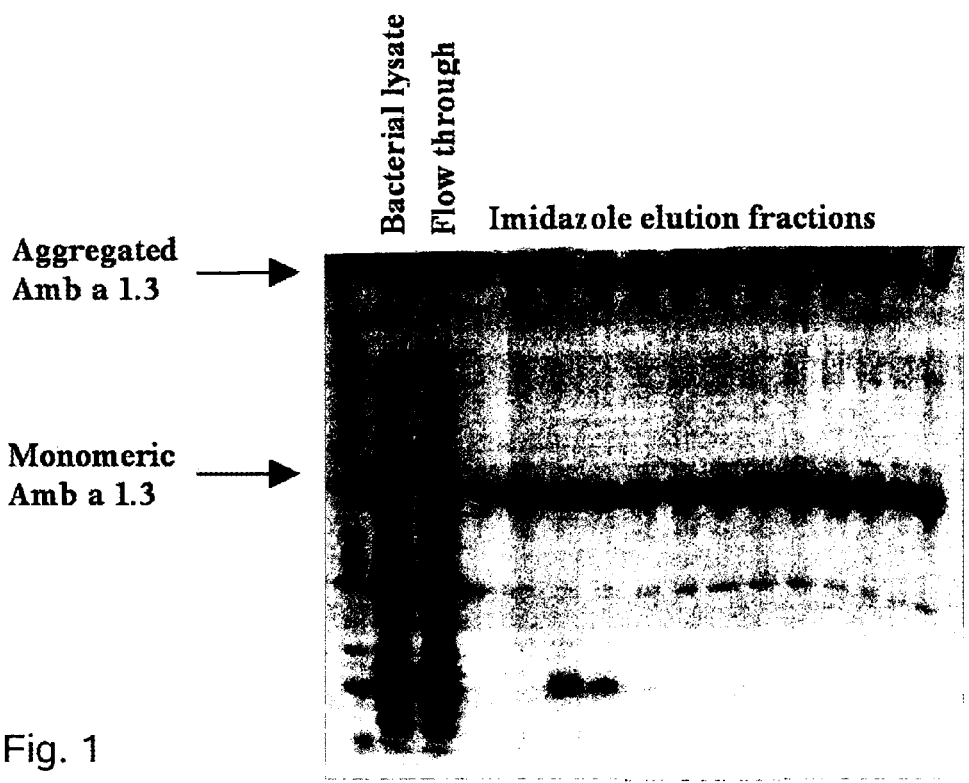

In terms of IgE-binding activity, the first attempts to produce full-length rAmb a 1.3 in *E. coli* were not encouraging. First of all, proteolytic cleavage occurred during the purification of rAmb a 1.3 produced in *E. coli*. The yield of rAmb a 1.3 was approximately 15 mg rAmb a 1.3 from 10 L fermentation culture. rAmb a 1.3 was found exclusively in inclusion bodies and therefore the use of protocols for refolding were necessary. However, the correct refolding of full-length rAmb a 1.3 turned out to be a hurdle. After using different standard procedures for refolding, the best preparations consisted mostly of insoluble aggregates (see FIG. 1).

Various changes in the purification protocol and addition of different stabilizing agents did not result in a correctly folded and soluble protein. In non-denaturing assays (e.g., dot blot, ELISA) rAmb a 1.3 was not able to bind human IgE (FIG. 2). Only after reduction and heat treatment (standard procedure for SDS-PAGE/immunoblotting) rAmb a 1.3 reacted with patients IgE. These results clearly demonstrated that rAmb a 1.3 produced as described above is not a suitable reagent for allergy diagnosis and therapy. Thus, another approach for producing recombinant reagents with full IgE-binding activity was pursued, as described in section 4. Despite its low IgE-binding activity, rAmb a 1.3 was successfully used in vitro for T cell epitope mapping and proliferation assays, as correct folding is not essential for T cell recognition (see example 2).

Example 2

T Cell Recognition of Amb a 1

Example 2.1

Patients

The T cell response to Amb a 1 was characterized in detail using the established in vitro culture system (Jahn-Schmid et al., J. Immunol. 169: 6005-11, 2002; Jahn-Schmid et al., J. Allergy Clin. Immunol., 115: 399-404, 2005). In total, 85 clinically well-defined patients (75 from Vienna/10 from Milano) with typical case history, positive skin prick test and CAP/RAST tests for ragweed extract were included.

Example 2.2

PBMC, Amb a 1-Specific T Cell Lines (TCL) and T Cell Clones (TCC)

Peripheral blood mononuclear cells (PBMC) were isolated from heparinized blood of allergic patients by Ficoll density gradient centrifugation. To generate allergen-specific T cell lines (TCL) and T cell clones (TCC), $1.5 \times 10^6$ PBMC were stimulated with optimal doses of ragweed or mugwort extract (4 µg/ml) or rAmb a 1.3 (10 µg/ml) in 24-well flat-bottomed culture plates (Costar, USA). After 5 days human rIL-2 (10 U/ml, Boehringer, Mannheim, Germany) were added and cultures were continued for additional 7 days. Then, T cell blasts were isolated by density centrifugation. The majority of T cell blasts was further expanded with IL-2 and irradiated PBMC. A small number of T cell blasts were used to establish monoclonal T cell cultures by limiting dilution: 0.3 T cells/well were seeded into 96 well round bottom plates (Nunclone) in the presence of $2 \times 10^5$ irradiated (60 Gy) PBMC, 0.25% v/v PHA (Gibco, USA) and rIL-2 (4 U/well) in the medium mentioned above. After 14-21 days, growing microcultures were expanded at weekly intervals with irradiated PBMC and rIL-2. The specificity of TCC was assessed in proliferation assays using irradiated allogeneic or HLA-matched PBMC or irradiated EBV-transformed allogeneic B-cells and 5 µg/ml Amb a 1.3. After 48 hours, cellular uptake of tritiated ($^3$H)-thymidine was performed to measure proliferation in counts per minute (cpm). When the stimulation index (SI; ratio between cpm obtained in cultures containing TCC plus autologous APC plus antigen, and cpm obtained in cultures containing TCC and APC alone) was >10, responses were considered as positive. Allergen-specific TCC were expanded by alternating turns of stimulation with autologous irradiated APC and allergen or with allogeneic feeder cells and rIL-2. For PBMC and TCL, which showed different degrees of background proliferation due to autoreactivity, an SI of >3 or respectively 10.000 dpm were considered as cut-off for antigen-specificity.

Amb a 1-specific TCL and TCC were used to identify T cell epitopes of Amb a 1.3. T cell cultures were stimulated with a panel of 121 synthetic 12-mer peptides and one 13-mer representing the C-terminal peptide of Amb a 1.3 (Pepset, Biotrend, Germany). Peptides had been synthesized according to the Amb a 1.3 amino acid sequence and overlapped for 9 amino acid residues with the neighbouring peptides (Table 1). Peptides were used at a concentration of 5 µg/ml for stimulation and proliferation of T cell cultures was determined after 48 hrs by $^3$H-thymidine-uptake. Because of the frequently observed high background caused by auto-reactivity in TCL, the mean of the cpm observed with the ten least stimulating peptides (none of the peptides was toxic) was used as negative control in calculations of SI. Throughout this manuscript, a peptide comprised one T cell epitope when the stimulation index was at least 3.0. Stronger stimulating peptides with SI≥5.0 are also indicated in Tables 2 and 3.

TABLE 1

Synthetic peptides used for T cell epitope mapping of Amb a 1.3. Deduced amino acid sequence of mature (without signal peptide) Amb a 1.3 was used as template to design 120 12-mer plus 1 13-mer peptide (corresponding to C-terminus of Amb a 1.3).

| Aa pos. | Pept # (=SEQ ID No.) | Sequence | Aa pos. | Pept # (=SEQ ID No.) | Sequence |
|---|---|---|---|---|---|
| 25-36 | 1 | SAEGVGEILPSV | 205-216 | 61 | QIWIDHCSLSKS |
| 28-39 | 2 | GVGEILPSVNET | 208-219 | 62 | IDHCSLSKSFDG |

TABLE 1-continued

Synthetic peptides used for T cell epitope mapping of Amb a 1.3.
Deduced amino acid sequence of mature (without signal peptide) Amb a
1.3 was used as template to design 120 12-mer plus 1 13-mer peptide
(corresponding to C-terminus of Amb a 1.3).

| Aa pos. | Pept # (=SEQ ID No.) | Sequence | Aa pos. | Pept # (=SEQ ID No.) | Sequence |
|---|---|---|---|---|---|
| 31-42 | 3 | EILPSVNETRSL | 211-222 | 63 | CSLSKSFDGLVD |
| 34-45 | 4 | PSVNETRSLQAC | 214-225 | 64 | SKSFDGLVDVTL |
| 37-48 | 5 | NETRSLQACEAY | 217-228 | 65 | FDGLVDVTLGST |
| 40-51 | 6 | RSLQACEAYNII | 220-231 | 66 | LVDVTLGSTHVT |
| 43-54 | 7 | QACEAYNIIDKC | 223-234 | 67 | VTLGSTHVTISN |
| 46-57 | 8 | EAYNIIDKCWRG | 226-237 | 68 | GSTHVTISNCKF |
| 49-60 | 9 | NIIDKCWRGKAD | 229-240 | 69 | HVTISNCKFTQQ |
| 52-63 | 10 | DKCWRGKADWEN | 232-243 | 70 | ISNCKFTQQSKA |
| 55-66 | 11 | WRGKADWENNRQ | 235-246 | 71 | CKFTQQSKAILL |
| 58-69 | 12 | KADWENNRQALA | 238-249 | 72 | TQQSKAILLGAD |
| 61-72 | 13 | WENNRQALADCA | 241-252 | 73 | SKAILLGADDTH |
| 64-75 | 14 | NRQALADCAQGF | 244-255 | 74 | ILLGADDTHVQD |
| 67-78 | 15 | ALADCAQGFAKG | 247-258 | 75 | GADDTHVQDKGM |
| 70-81 | 16 | DCAQGFAKGTYG | 250-261 | 76 | DTHVQDKGMLAT |
| 73-84 | 17 | QGFAKGTYGGKW | 253-264 | 77 | VQDKGMLATVAF |
| 76-87 | 18 | AKGTYGGKWGDV | 256-267 | 78 | KGMLATVAFNMF |
| 79-90 | 19 | TYGGKWGDVYTV | 259-270 | 79 | LATVAFNMFTDN |
| 82-93 | 20 | GKWGDVYTVTSN | 262-273 | 80 | VAFNMFTDNVDQ |
| 85-96 | 21 | GDVYTVTSNLDD | 265-276 | 81 | NMFTDNVDQRMP |
| 88-99 | 22 | YTVTSNLDDDVA | 268-279 | 82 | TDNVDQRMPRCR |
| 91-102 | 23 | TSNLDDDVANPK | 271-282 | 83 | VDQRMPRCRFGF |
| 94-105 | 24 | LDDDVANPKEGT | 274-285 | 84 | RMPRCRFGFFQV |
| 97-108 | 25 | DVANPKEGTLRF | 277-288 | 85 | RCRFGFFQVVNN |
| 100-111 | 26 | NPKEGTLRFAAA | 280-291 | 86 | FGFFQVVNNNYD |
| 103-114 | 27 | EGTLRFAAAQNR | 283-294 | 87 | FQVVNNNYDRWG |
| 106-117 | 28 | LRFAAAQNRPLW | 286-297 | 88 | VNNNYDRWGTYA |
| 109-120 | 29 | AAAQNRPLWIIF | 289-300 | 89 | NYDRWGTYAIGG |
| 112-123 | 30 | QNRPLWIIFKND | 292-303 | 90 | RWGTYAIGGSSA |
| 115-126 | 31 | PLWIIFKNDMVI | 295-306 | 91 | TYAIGGSSAPTI |
| 118-129 | 32 | IIFKNDMVINLN | 298-309 | 92 | IGGSSAPTILCQ |
| 121-132 | 33 | KNDMVINLNQEL | 301-312 | 93 | SSAPTILCQGNR |
| 124-135 | 34 | MVINLNQELVVN | 304-315 | 94 | PTILCQGNRFLA |
| 127-138 | 35 | NLNQELVVNSDK | 307-318 | 95 | LCQGNRFLAPDD |
| 130-141 | 36 | QELVVNSDKTID | 310-321 | 96 | GNRFLAPDDQIK |
| 133-144 | 37 | VVNSDKTIDGRG | 313-324 | 97 | FLAPDDQIKKNV |
| 136-147 | 38 | SDKTIDGRGVKV | 316-327 | 98 | PDDQIKKNVLAR |

TABLE 1-continued

Synthetic peptides used for T cell epitope mapping of Amb a 1.3. Deduced amino acid sequence of mature (without signal peptide) Amb a 1.3 was used as template to design 120 12-mer plus 1 13-mer peptide (corresponding to C-terminus of Amb a 1.3).

| Aa pos. | Pept # (=SEQ ID No.) | Sequence | Aa pos. | Pept # (=SEQ ID No.) | Sequence |
|---|---|---|---|---|---|
| 139-150 | 39 | TIDGRGVKVEII | 319-330 | 99 | QIKKNVLARTGT |
| 142-153 | 40 | GRGVKVEIINGG | 322-333 | 100 | KNVLARTGTGAA |
| 145-156 | 41 | VKVEIINGGLTL | 325-336 | 101 | LARTGTGAAESM |
| 148-159 | 42 | EIINGGLTLMNV | 328-339 | 102 | TGTGAAESMAWN |
| 151-162 | 43 | NGGLTLMNVKNI | 331-342 | 103 | GAAESMAWNWRS |
| 154-165 | 44 | LTLMNVKNIIIH | 334-345 | 104 | ESMAWNWRSDKD |
| 157-168 | 45 | MNVKNIIIHNIN | 337-348 | 105 | AWNWRSDKDLLE |
| 160-171 | 46 | KNIIIHNINIHD | 340-351 | 106 | WRSDKDLLENGA |
| 163-174 | 47 | IIHNINIHDVKV | 343-354 | 107 | DKDLLENGAIFV |
| 166-177 | 48 | NINIHDVKVLPG | 346-357 | 108 | LLENGAIFVTSG |
| 169-180 | 49 | IHDVKVLPGGMI | 349-360 | 109 | NGAIFVTSGSDP |
| 172-183 | 50 | VKVLPGGMIKSN | 352-363 | 110 | IFVTSGSDPVLT |
| 175-186 | 51 | LPGGMIKSNDGP | 355-366 | 111 | TSGSDPVLTPVQ |
| 178-189 | 52 | GMIKSNDGPPIL | 358-369 | 112 | SDPVLTPVQSAG |
| 181-192 | 53 | KSNDGPPILRQA | 361-372 | 113 | VLTPVQSAGMIP |
| 184-195 | 54 | DGPPILRQASDG | 364-375 | 114 | PVQSAGMIPAEP |
| 187-198 | 55 | PILRQASDGDTI | 367-378 | 115 | SAGMIPAEPGEA |
| 190-201 | 56 | RQASDGDTINVA | 370-381 | 116 | MIPAEPGEAAIK |
| 193-204 | 57 | SDGDTINVAGSS | 373-384 | 117 | AEPGEAAIKLTS |
| 196-207 | 58 | DTINVAGSSQIW | 376-387 | 118 | GEAAIKLTSSAG |
| 199-210 | 59 | NVAGSSQIWIDH | 379-390 | 119 | AIKLTSSAGVLS |
| 202-213 | 60 | GSSQIWIDHCSL | 382-393 | 120 | LTSSAGVLSCRP |
|  |  |  | 385-397 | 121 | SAGVLSCRPGAPC |

Example 2.3

Measurement of Cytokines

T cells were washed and incubated with irradiated autologous APC in the presence of the stimulant (5 µg/ml) for 48 hours. Cytokine levels in the resulting supernatants were measured in ELISA using matched antibody pairs (Endogen, USA) (sensitivity limits: IL-4: 9 pg/ml, IFN-γ: 9 pg/ml). Cultures containing TCC and APC alone served as negative controls. TCC with a ratio of IFN-γ/IL-4>10 were classified as Th1, 0.1-10 as Th0 and <0.1 as Th2.

Example 2.4

Flow Cytometry

The phenotype of TCC was analyzed by flow cytometry, using a FACScan and the FITC-labeled monoclonal antibodies anti-Leu4/CD3, anti-Leu 3a/CD4, anti-Leu 2a/CD8, anti-TCR αβ WT 31, anti-TCR γδ and CRTh2 plus goat-anti-rat-PE (all antibodies were obtained from BD Bioscience, USA).

Example 2.5

Comparison of rAmb a 1.3 with Natural Amb a 1

Figure 3:
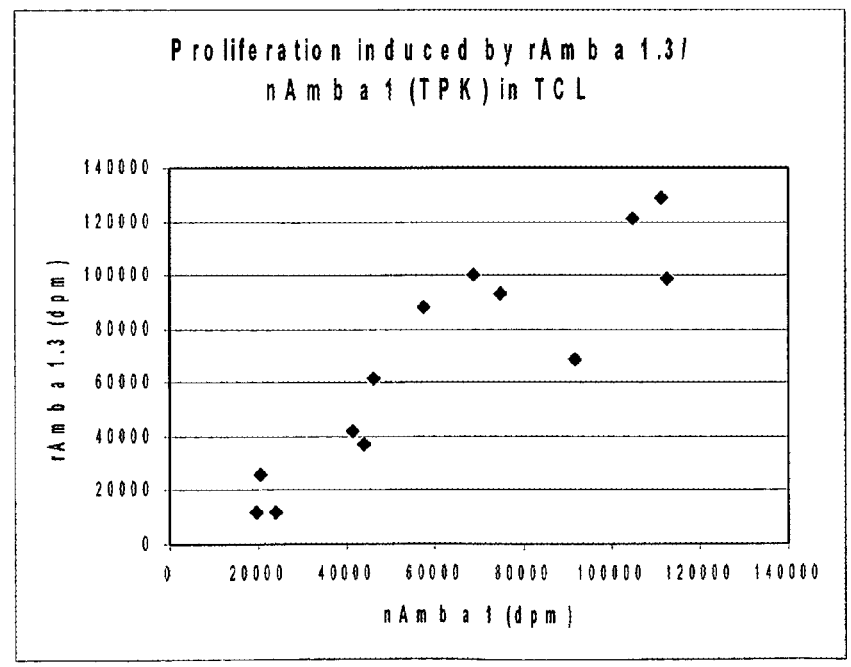
Figure 4:
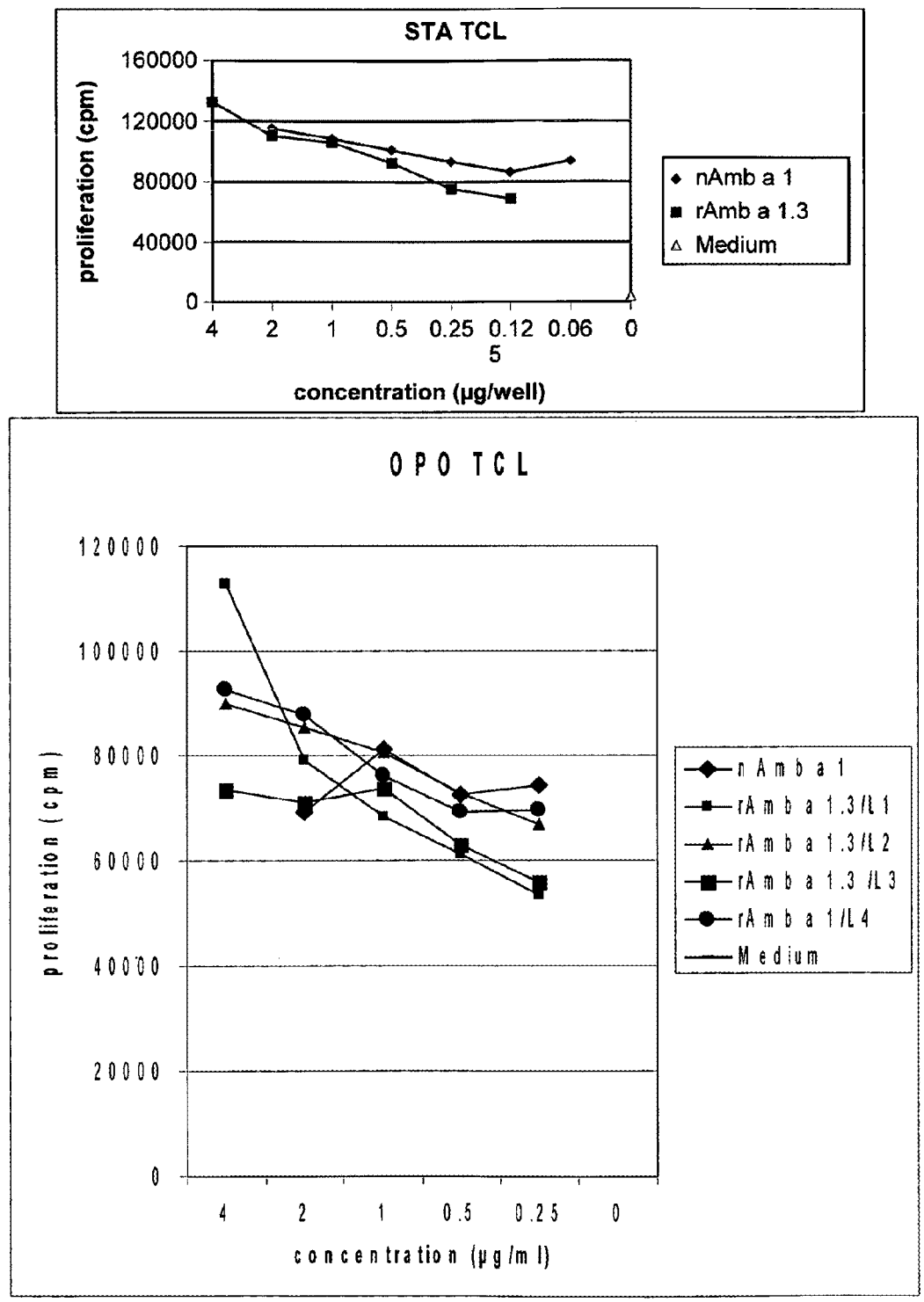
FIG. 4 shows examples of allergen titrations in TCL proliferation assays—natural versus recombinant allergens (different lots of rAmb a 1.3, lots L1-L4). STA and OPO are TCL from 2 different ragweed allergic patients, respectively.
Figure 6:
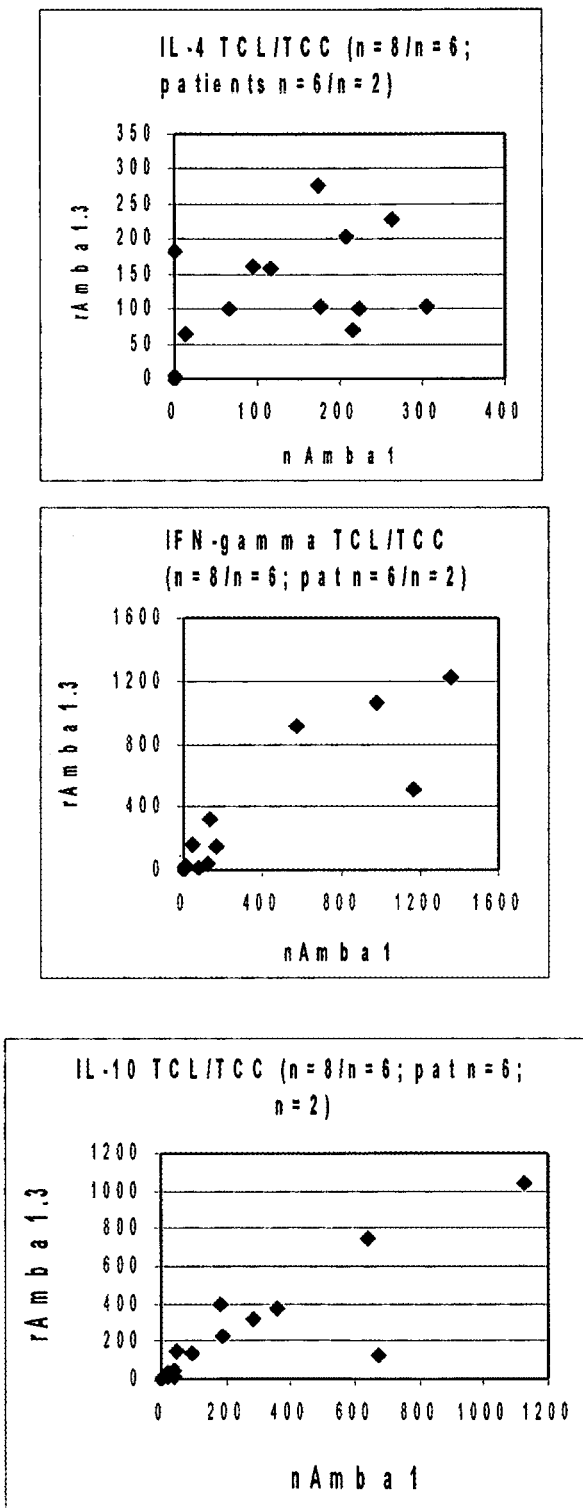
FIG. 6 shows comparable cytokine production induced by natural and rAmb a 1.3 in TCL and TCC.

To confirm that recombinant Amb a 1.3 isoform stimulated T cells comparable to natural Amb a 1 (mixture of isoforms), PBMC and Amb a 1-specific TCL and TCC were stimulated with different concentrations of natural or rAmb a 1.3. Proliferation and cytokine responses were determined. The stimulatory capacity of both allergens was relatively stable over a range of concentrations and in general natural and rAmb a 1.3 induced comparable T cell proliferations (FIGS. 3 and 4) and cytokine production (FIGS. 5 and 6). At the clonal level 1/6 tested Amb a 1-specific TCC recognizing different epitopes of rAmb a 1.3 did not respond to natural Amb a 1 (epitope: aa 265-276). TCL induced with ragweed extract or recombinant Amb a 1.3 showed similar T cell epitope patterns (FIG. 7).

Example 2.6

T Cell Epitopes of Amb a 1.3

T cell epitope mapping of Amb a 1.3 was performed evaluating 48 TCL from different patients (37 from Vienna and 9 from Italy), which had been initiated with ragweed extract (containing the natural allergen) or rAmb a 1.3 (Table 2). TCL induced with either ragweed extract or rAmb a 1.3 from the same individual recognized similar T cell epitopes (Table 2; FIG. 7). Austrian and Italian patients showed a similar epitope recognition profile. Therefore, their data were combined for further analysis (Table 3). Typical for many inhalant allergens, multiple T cell activating regions were detected in Amb a 1.3. The number of peptides recognized by T cells from a single individual ranged from 2 to maximum 60 peptides with a mean of 17.8 peptides (median=16/for SI>3; resp. 0-36/11.9/12 for SI>5) (see Table 3). In total, 26 relevant (i.e. recognized by ≥10% of patients studied) T cell activating regions comprising 12-18 aa were identified. These epitope-containing regions were divided into classes of prevalence (referring to SI>5):

11 regions were positive in 10-20% of patients:
(SEQ ID No. 20)
Peptide 20 (aa 82-93), GKWGDVYTVTSN,
recognized by 14.6%

(SEQ ID No. 42)
42; (aa 148-159), EIINGGLTLMNV,
recognized by 10.4%

(SEQ ID No. 44)
44 (aa 154-165), LTLMNVKNIIIH,
recognized by 18.8%

(SEQ ID No. 78)
78; (aa 256-267), KGMLATVAFNMF,
recognized by 12.5%

(SEQ ID No. 122)
80-81 (aa 262-276), VAFNMFTDNVDQRMP,
recognized by 12.5 %

(SEQ ID No. 83)
83; (aa 271-282), VDQRMPRCRFGF,
recognized by 16.7%

(SEQ ID No. 123)
88-89: (aa 286-300), VNNNYDRWGTYAIGG,
recognized by 12.5%

(SEQ ID No. 94)
94 (aa 304-315), PTILCQGNRFLA,
recognized by 18.8%

(SEQ ID No. 124)
98-99; (aa 316-330), PDDQIKKNVLARTGT,
recognized by 16.7%

(SEQ ID No. 100)
100; (aa 322-333). KNVLARTGTGAA,
recognized by 10.4%

(SEQ ID No. 125)
101/102 (aa 325-339), LARTGTGAAESMAWN,
recognized by 14.6%

9 regions were positive in 21-30% of patients:
(SEQ ID No. 126)
Peptide 27-28 (aa 103-117), EGTLRFAAAQNRPLW,
recognized by 22.9%

(SEQ ID No. 127)
30-31 (aa 112-26), QNRPLWIIFKNDMVI,
recognized by 20.8%

(SEQ ID No. 128)
33-34 (aa 121-135), KNDMVINLNQELVVN,
recognized by 27.1%

(SEQ ID No. 129)
36-37 (aa 130-144), QELVVNSDKTIDGRG,
recognized by 25.0%

(SEQ ID No. 130)
46-48 (aa 160-177), KNIIIHNINIHDVKVLPG,
recognized by 20.8%

(SEQ ID No. 86)
86; (aa 280-291), FGFFQVVNNNYD,
recognized by 20.6%

(SEQ ID No. 91)
91 (aa 295-306), TYAIGGSSAPTI,
recognized by 22.9%

(SEQ ID No. 131)
109-111; (aa 349-366), NGAIFVTSGSDPVLTPVQ,
recognized by 22.9%

(SEQ ID No. 132)
118-120 (aa 376-393); GEAAIKLTSSAGVLSCRP,
recognized by 20.8%

3 regions were positive in 31-49% of patients:
(SEQ ID No. 133)
Peptide 38-40 (aa 136-153), SDKTIDGRGVKVEIINGG,
recognized by 33.3%

(SEQ ID No. 68)
68 (aa 226-237), GSTHVTISNCKF,
recognized by 33.3 %

(SEQ ID No. 134)
114-115 (aa 364-378), PVQSAGMIPAEPGEA,
recognized by 35.4 %

3 regions were positive in >50% of patients:
(SEQ ID No. 52)
Peptide 52 (aa 178-189), GMIKSNDGPPIL,
recognized by 56.3%

(SEQ ID No. 135)
59-61 (aa 199-216), NVAGSSQIWIDHCSLSKS,
recognized by 58.3%

(SEQ ID No. 136)
107-108 (aa 343-357), DKDLLENGAIFVTSG,
recognized by 56.3%

The three T cell activating regions inducing proliferative responses in more than 50% of the allergic patients were defined as immunodominant epitopes (FIG. 8; Table 3).

In general, the T cell activating capacity of a certain peptide did not correlate with the frequency of recognition. Therefore, also a "positivity index" (PI; % positive patients×mean SI) was calculated to reveal other important epitopes. PI ranged from 98-2300 and identified the three immunodominant regions mentioned above and 4 additional regions as strongly immunogenic regions (PI>700; 27% highest values) in Amb a 1.3:

(SEQ ID No. 130)
46-48: aa 160-177: KNIIIHNINIHDVKVLPG (SEQ ID No. 131)
109-111: aa 349-366: NGAIFVTSGSDPVLTPVQ

-continued (SEQ ID No. 134)
114-115: aa 364-378: PVQSAGMIPAEPGEA (SEQ ID No. 132)
118-120: aa 376-393: GEAAIKLTSSAGVLSCRP In addition to TCL, more than 100 Amb a 1-specific TCC from 10 different ragweed pollen-allergic patients was established. With the exception of one CD8+ TCC, these TCC were shown to be CD4$^+$TCR $\alpha\beta^+$ T cells. Investigation of the cytokine production in 108 Amb a 1-specific TCC (n=10 patients) revealed a Th2-like cytokine profile in the majority (50%) of these TCC (Th1: 11%; Th0 39%). In addition, 74% of 68 investigated TCC (patients n=8) expressed CRTh2, a surface marker for Th2 T cells also indicating that Amb a 1-specific T cells in our culture represent relevant allergenic T cells. T cell epitope mapping of Amb a 1.3 using Amb a 1-specific TCC reflected the data obtained from TCL. Results show that the presentation of Amb a 1-peptides is diverse, involving HLA-DR, -DP or -DQ as restriction elements.

In the U.S. Pat. No. 6,335,020 (Allergenic peptides from ragweed pollen) 4 major regions of T cell reactivity have been reported: aa 57-101, 182-215, 280-322 and 342-377 (FIG. 6). This epitope distribution differs to some extent from the epitopes of the present invention, e.g. in contrast to region aa 57-101, it was found that epitopes within aa 109-180 are much more frequently recognized. T cell epitopes from related tree pollen allergens Cha o 1 (Japanese cypress), Cry j 1 (Japanese cedar) have been described by others (Sone et al., Clin Exp Allergy, 35: 664-71, 2005). The major epitopes of these allergens are located in regions that are homologous to minor T cell epitopes in Amb a 1.

TABLE 2

T cell epitopes of Amb a 1-specific TCL from 48 different ragweed pollen-allergic patients. TCL were initiated either with rAmb a 1.3 or with ragweed pollen extract. Peptides giving Stimulation indexes (SI) higher than 3 and 5 are listed for each patient.

| Patient No. | Peptide No. (SI > 3) | Peptide No. (SI > 5) |
|---|---|---|
| 1 | 112, 114 | 8, 31, 33, 36, 44, 52, 59, 60, 61, 68, 78, 102, 108, 109, 110, 111, 115, 116, 117, 118, 119, 120 |
| 2 | 29, 30, 42, 64, 67, 79, 88, 89, 93, 98, 101, 103 | 27, 28, 33, 52, 60, 61, 68, 94, 107, 108, 111, 114, 115, 116, 118, 119, 120 |
| 3 | 120 | 107 |
| 4 | 41, 42, 60, 90, 98 | 52, 83, 91, 107, 108 |
| 5 | 39, 78, 85, 99, 101, 102, 107, 108 | 28, 36, 37, 44, 52, 60, 61, 86, 100, 104, 105, 106, 109, 110, 111, 119, 120 |
| 6 | 34 | 83, 91, 107, 108, 115 |
| 7 | 11, 58, 68, 78, 82, 84, 86, 88, 89, 99, 108 | 33, 39, 47, 48, 51, 52, 59, 60, 61, 107 |
| 8 | 34, 44, 45, 72, 79, 80 | 33, 39, 40, 50, 71, 83, 107 |
| 9 | 50, 76, 83, 87, 101, 112, 113, 119, 121 | 39, 69, 91, 93, 107, 117 |
| 10 | 47, 96, 97, 110, 119 | 44, 46, 60, 61, 69, 89, 101, 107, 108, 115 |
| 11 | 110 | 33, 38, 39, 46, 52, 60, 69, 83, 90, 91, 107, 108, 115 |
| 12 | 59 | 36, 37, 52, 60, 61, 68, 86, 96, 97, 98 |

TABLE 2-continued

T cell epitopes of Amb a 1-specific TCL from 48 different ragweed pollen-allergic patients. TCL were initiated either with rAmb a 1.3 or with ragweed pollen extract. Peptides giving Stimulation indexes (SI) higher than 3 and 5 are listed for each patient.

| Patient No. | Peptide No. (SI > 3) | Peptide No. (SI > 5) |
|---|---|---|
| 13 | 14, 37, 44, 61, 71, 77, 108, 111, 121 | 20, 28, 36, 47, 101, 109, 110, 118 |
| 14 | 30, 31, 111, 120 | 119 |
| 15 | 8, 20, 46, 47, 71, 77, 107, 108 | |
| 16 | 87 | 21, 46, 47, 54, 55, 63, 86 |
| 17 | 14, 23, 29, 34, 53, 58, 69, 76, 80, 82, 85, 99, 102, 107, 115 | 20, 22, 28, 31, 33, 36, 37, 44, 52, 60, 61, 68, 77, 81, 84, 88, 98, 108, 109, 110, 111, 118, 119, 120 |
| 18 | 33, 104 | 38, 39, 52, 60, 61, 68, 81, 96, 97, 98, 107, 108, 112 |
| 19 | | 20, 28, 36, 37, 44, 47, 48, 52, 59, 60, 67, 77, 78 |
| 20 | 60, 61 | |
| 21 | 29, 34, 47, 61 | 30, 33, 38, 39, 42, 43, 46, 49, 52, 60, 91, 94, 107, 108, 114, 115 |
| 22 | 20, 39, 44, 52, 53, 64, 69, 85, 94 | 28, 37, 38, 40, 60, 61, 68, 86 |
| 23 | 23, 51, 53, 54, 55, 59, 116, 117, 120 | 9, 30, 31, 32, 33, 34, 38, 39, 46, 47, 48, 52, 60, 61, 68, 81, 88, 89, 98, 99, 107, 108, 111, 115, 118, 119 |
| 24 | 28, 114 | 11, 34, 37, 38, 52, 68, 83, 89, 91, 100, 101, 102, 107, 108, 109, 110, 115 |
| 25 | 44, 111, 119, 120 | 60, 61, 77, 92, 93, 94107, 108, 109, 110 |
| 26 | 28, 29, 30, 36, 44, 68, 83, 84, 118, 121 | 12, 15, 22, 23, 31, 33, 52, 60, 61, 73, 74, 78, 82, 86, 107, 108, 111, 113, 115, 119, 120 |
| 27 | 43, 107 | 10, 22, 28, 30, 33, 36, 37, 48, 52, 60, 61, 86, 87 |
| 28 | 33, 39, 61, 73, 93, 94, 99, 118 | 36, 52, 60, 77, 88, 102, 107, 108, 109, 110, 111, 119, 120 |
| 29 | 28, 81, 83, 86, 87, 91, 100 | 31, 39, 52, 59, 60, 61, 67, 68, 69, 80, 107, 108, 111, 115, 118, 119, 120 |
| 30 | 4, 78 | 20, 27, 28, 29, 30, 36, 37, 44, 52, 60, 61, 68, 80, 93, 94, 108, 117 |
| 31 | 11, 32, 77 | 29, 30, 38, 39, 40, 42, 46, 47, 48, 61, 79, 89, 94, 108, 115 |
| 32 | 1, 77 | 4, 20, 22, 28, 36, 37, 38, 39, 41, 42, 44, 50, 52, 60, 61, 62, 66, 68, 78, 83, 86, 90, 91, 96, 97, 98, 105, 107, 108, 115 |
| 33 | 12, 61 | 52, 60, 68, 108 |
| 34 | 28, 30, 42, 91 | 24, 27, 29, 94, 108, 114 |
| 35 | 37, 38, 69, 72 | 20, 28, 33, 36, 39, 42, 44, 48, 52, 58, 60, 61, 68, 94, 114 |
| 36 | 7, 9, 12, 15, 16, 28, 33, 37, 39, 43, 47 | 30, 52, 60, 61, 68, 96, 97, 98, 107 |
| 37 | 5, 12, 29, 55, 59 | |

TABLE 2-continued

T cell epitopes of Amb a 1-specific TCL from 48 different ragweed pollen-allergic patients. TCL were initiated either with rAmb a 1.3 or with ragweed pollen extract. Peptides giving Stimulation indexes (SI) higher than 3 and 5 are listed for each patient.

| Patient No. | Peptide No. (SI > 3) | Peptide No. (SI > 5) |
|---|---|---|
| 38 | 19, 37, 39, 41, 42, 43, 45, 46, 47, 48, 49, 51, 98, 107, 109, 113 | 20, 22, 28, 31, 36, 44, 52, 78, 82, 86, 89, 90, 101, 102, 110, 111, 118, 119, 120 |
| 39 | 4, 52 | 33, 42, 47, 48, 59, 60, 78, 98, 99, 107 |
| 40 | 24, 25, 33, 52, 73, 78, 98, 109, 111, 119 | 31, 66, 68, 71, 80, 81, 83, 102, 107, 108, 110, 112, 115, 120 |
| 41 | 2, 17, 20, 28, 30, 36, 37, 38, 44, 61, 92 | 27, 31, 39, 52, 83, 91, 94 |
| 42 | 67, 80 | 91, 93, 101 |
| 43 | 28, 62, 68, 76, 88, 89 | 38, 39, 51, 52, 59, 60, 61, 80, 81, 86, 92, 100, 101, 102, 109, 110 |
| 44 | 35, 80, 88, 90, 119 | 30, 31, 38, 39, 46, 47, 48, 51, 52, 59, 60, 94, 100, 107, 108, 111, 112, 115, 121 |
| 45 | 5, 39, 41, 42, 48, 51, 52, 53, 54, 65, 67, 68, 74, 78, 79, 84, 89, 106, 109, 112 | 47, 60, 61, 63, 64, 66, 72, 73, 75, 76, 80, 85, 86, 87, 88, 101, 107, 108, 115, 116 |
| 46 | 88 | 27, 91, 107 |
| 47 | 3, 4, 5, 6, 13, 14, 16, 23, 28, 41, 49, 61, 74, 89, 98, 102, 108, 112, 113, 114, 116, 119, 120, 121 | 2, 9, 15, 30, 50, 56, 62, 91, 99, 100, 103, 105, 107, 110, 111, 115, 117 |
| 48 | 1, 5, 8, 12, 13, 14, 15, 18, 19, 20, 21, 25, 32, 36, 42, 53, 65, 67, 69, 88, 97, 105, 106, 111 | 10, 11, 18, 30, 31, 33, 38, 39, 40, 46, 47, 48, 49, 50, 52, 54, 59, 60, 61, 66, 68, 70, 72, 79, 80, 81, 89, 98, 99, 107, 108, 109, 114, 115, 116, 118, 121 |

TABLE 3

T cell epitopes of Amb a 1-specific T cell lines (TCL) from 48 different ragweed pollen-allergic patients (see Table 2). 121 overlapping synthetic peptides (12-mer) were used for epitope mapping. The relevance of each epitope was separately evaluated for stimulation indexes higher than 3 (SI > 3) and higher than 5 (SI > 5).

| Peptide (=SEQ ID No.) | AA position | AA sequence | No. positive patients SI > 3 | % | No. positive patients SI > 5 | % |
|---|---|---|---|---|---|---|
| 1 | 25-36 | SAEGVGEILPSV | 2 | 4.2 | 0 | 0.0 |
| 2 | 28-39 | GVGEILPSVNET | 2 | 4.2 | 1 | 2.1 |
| 3 | 31-42 | EILPSVNETRSL | 1 | 2.1 | 0 | 0.0 |
| 4 | 34-45 | PSVNETRSLQAC | 4 | 8.3 | 1 | 2.1 |
| 5 | 37-48 | NETRSLQACEAY | 4 | 8.3 | 0 | 0.0 |
| 6 | 40-51 | RSLQACEAYNII | 1 | 2.1 | 0 | 0.0 |
| 7 | 43-54 | QACEAYNIIDKC | 1 | 2.1 | 0 | 0.0 |
| 8 | 46-57 | EAYNIIDKCWRG | 3 | 6.3 | 1 | 2.1 |
| 9 | 49-60 | NIIDKCWRGKAD | 3 | 6.3 | 2 | 4.2 |
| 10 | 52-63 | DKCWRGKADWEN | 2 | 4.2 | 2 | 4.2 |
| 11 | 55-66 | WRGKADWENNRQ | 4 | 8.3 | 2 | 4.2 |
| 12 | 58-69 | KADWENNRQALA | 5 | 10.4 | 1 | 2.1 |
| 13 | 61-72 | WENNRQALADCA | 2 | 4.2 | 0 | 0.0 |
| 14 | 64-75 | NRQALADCAQGF | 4 | 8.3 | 0 | 0.0 |
| 15 | 67-78 | ALADCAQGFAKG | 4 | 8.3 | 2 | 4.2 |
| 16 | 70-81 | DCAQGFAKGTYG | 2 | 4.2 | 0 | 0.0 |
| 17 | 73-84 | QGFAKGTYGGKW | 2 | 4.2 | 1 | 2.1 |

TABLE 3-continued

T cell epitopes of Amb a 1-specific T cell lines (TCL) from 48 different ragweed pollen-allergic patients (see Table 2). 121 overlapping synthetic peptides (12-mer) were used for epitope mapping. The relevance of each epitope was separately evaluated for stimulation indexes higher than 3 (SI > 3) and higher than 5 (SI > 5).

| Peptide (=SEQ ID No.) | AA position | AA sequence | No. positive patients SI > 3 | % | No. positive patients SI > 5 | % |
| --- | --- | --- | --- | --- | --- | --- |
| 18 | 76-87 | AKGTYGGKWGDV | 1 | 2.1 | 0 | 0.0 |
| 19 | 79-90 | TYGGKWGDVYTV | 2 | 4.2 | 0 | 0.0 |
| 20 | 82-93 | GKWGDVYTVTSN | 9 | 18.8 | 7 | 14.6 |
| 21 | 85-96 | GDVYTVTSNLDD | 2 | 4.2 | 1 | 2.1 |
| 22 | 88-99 | YTVTSNLDDDVA | 4 | 8.3 | 4 | 8.3 |
| 23 | 91-102 | TSNLDDDVANPK | 2 | 4.2 | 1 | 2.1 |
| 24 | 94-105 | LDDDVANPKEGT | 2 | 4.2 | 1 | 2.1 |
| 25 | 97-108 | DVANPKEGTLRF | 2 | 4.2 | 0 | 0.0 |
| 26 | 100-111 | NPKEGTLRFAAA | 0 | 0.0 | 0 | 0.0 |
| 27 | 103-114 | EGTLRFAAAQNR | 5 | 10.4 | 5 | 10.4 |
| 28 | 106-117 | LRFAAAQNRPLW | 15 | 31.3 | 11 | 22.9 |
| 29 | 109-120 | AAAQNRPLWIIF | 4 | 8.3 | 3 | 6.3 |
| 30 | 112-123 | QNRPLWIIFKND | 11 | 22.9 | 9 | 18.8 |
| 31 | 115-126 | PLWIIFKNDMVI | 11 | 22.9 | 10 | 20.8 |
| 32 | 118-129 | IIFKNDMVINLN | 2 | 4.2 | 1 | 2.1 |
| 33 | 121-132 | KNDMVINLNQEL | 15 | 31.3 | 13 | 27.1 |
| 34 | 124-135 | MVINLNQELVVN | 2 | 4.2 | 2 | 4.2 |
| 35 | 127-138 | NLNQELVVNSDK | 1 | 2.1 | 1 | 2.1 |
| 36 | 130-141 | QELVVNSDKTID | 14 | 29.2 | 12 | 25.0 |
| 37 | 133-144 | VVNSDKTIDGRG | 14 | 29.2 | 9 | 18.8 |
| 38 | 136-147 | SDKTIDGRGVKV | 13 | 27.1 | 11 | 22.9 |
| 39 | 139-150 | TIDGRGVKVEII | 19 | 39.6 | 16 | 33.3 |
| 40 | 142-153 | GRGVKVEIINGG | 3 | 6.3 | 4 | 8.3 |
| 41 | 145-156 | VKVEIINGGLTL | 5 | 10.4 | 1 | 2.1 |
| 42 | 148-159 | EIINGGLTLMNV | 11 | 22.9 | 5 | 10.4 |
| 43 | 151-162 | NGGLTLMNVKNI | 4 | 8.3 | 1 | 2.1 |
| 44 | 154-165 | LTLMNVKNIIIH | 15 | 31.3 | 9 | 18.8 |
| 45 | 157-168 | MNVKNIIIHNIN | 2 | 4.2 | 0 | 0.0 |
| 46 | 160-171 | KNIIIHNINIHD | 10 | 20.8 | 8 | 16.7 |
| 47 | 163-174 | IIHNINIHDVKV | 14 | 29.2 | 10 | 20.8 |
| 48 | 166-177 | NINIHDVKVLPG | 10 | 20.8 | 9 | 18.8 |
| 49 | 169-180 | IHDVKVLPGGMI | 3 | 6.3 | 2 | 4.2 |
| 50 | 172-183 | VKVLPGGMIKSN | 5 | 10.4 | 4 | 8.3 |
| 51 | 175-186 | LPGGMIKSNDGP | 6 | 12.5 | 3 | 6.3 |

TABLE 3-continued

T cell epitopes of Amb a 1-specific T cell lines (TCL) from 48 different ragweed pollen-allergic patients (see Table 2). 121 overlapping synthetic peptides (12-mer) were used for epitope mapping. The relevance of each epitope was separately evaluated for stimulation indexes higher than 3 (SI > 3) and higher than 5 (SI > 5).

| Peptide (=SEQ ID No.) | AA position | AA sequence | No. positive patients SI > 3 | % | No. positive patients SI > 5 | % |
|---|---|---|---|---|---|---|
| 52 | 178-189 | GMIKSNDGPPIL | 31 | 64.6 | 27 | 56.3 |
| 53 | 181-192 | KSNDGPPILRQA | 5 | 10.4 | 0 | 0.0 |
| 54 | 184-195 | DGPPILRQASDG | 4 | 8.3 | 2 | 4.2 |
| 55 | 187-198 | PILRQASDGDTI | 3 | 6.3 | 1 | 2.1 |
| 56 | 190-201 | RQASDGDTINVA | 1 | 2.1 | 1 | 2.1 |
| 57 | 193-204 | SDGDTINVAGSS | 0 | 0.0 | 0 | 0.0 |
| 58 | 196-207 | DTINVAGSSQIW | 3 | 6.3 | 1 | 2.1 |
| 59 | 199-210 | NVAGSSQIWIDH | 11 | 22.9 | 8 | 16.7 |
| 60 | 202-213 | GSSQIWIDHCSL | 30 | 62.5 | 28 | 58.3 |
| 61 | 205-216 | QIWIDHCSLSKS | 29 | 60.4 | 24 | 50.0 |
| 62 | 208-219 | IDHCSLSKSFDG | 3 | 6.3 | 2 | 4.2 |
| 63 | 211-222 | CSLSKSFDGLVD | 2 | 4.2 | 2 | 4.2 |
| 64 | 214-225 | SKSFDGLVDVTL | 3 | 6.3 | 1 | 2.1 |
| 65 | 217-228 | FDGLVDVTLGST | 2 | 4.2 | 1 | 2.1 |
| 66 | 220-231 | LVDVTLGSTHVT | 4 | 8.3 | 4 | 8.3 |
| 67 | 223-234 | VTLGSTHVTISN | 6 | 12.5 | 2 | 4.2 |
| 68 | 226-237 | GSTHVTISNCKF | 20 | 41.7 | 16 | 33.3 |
| 69 | 229-240 | HVTISNCKFTQQ | 8 | 16.7 | 4 | 8.3 |
| 70 | 232-243 | ISNCKFTQQSKA | 1 | 2.1 | 1 | 2.1 |
| 71 | 235-246 | CKFTQQSKAILL | 4 | 8.3 | 2 | 4.2 |
| 72 | 238-249 | TQQSKAILLGAD | 4 | 8.3 | 2 | 4.2 |
| 73 | 241-252 | SKAILLGADDTH | 4 | 8.3 | 2 | 4.2 |
| 74 | 244-255 | ILLGADDTHVQD | 3 | 6.3 | 1 | 2.1 |
| 75 | 247-258 | GADDTHVQDKGM | 1 | 2.1 | 1 | 2.1 |
| 76 | 250-261 | DTHVQDKGMLAT | 4 | 8.3 | 1 | 2.1 |
| 77 | 253-264 | VQDKGMLATVAF | 7 | 14.6 | 4 | 8.3 |
| 78 | 256-267 | KGMLATVAFNMF | 11 | 22.9 | 6 | 12.5 |
| 79 | 259-270 | LATVAFNMFTDN | 5 | 10.4 | 2 | 4.2 |
| 80 | 262-273 | VAFNMFTDNVDQ | 10 | 20.8 | 6 | 12.5 |
| 81 | 265-276 | NMFTDNVDQRMP | 7 | 14.6 | 6 | 12.5 |
| 82 | 268-279 | TDNVDQRMPRCR | 3 | 6.3 | 2 | 4.2 |
| 83 | 271-282 | VDQRMPRCRFGF | 10 | 20.8 | 8 | 16.7 |
| 84 | 274-285 | RMPRCRFGFFQV | 3 | 6.3 | 1 | 2.1 |
| 85 | 277-288 | RCRFGFFQVVNN | 4 | 8.3 | 1 | 2.1 |

TABLE 3-continued

T cell epitopes of Amb a 1-specific T cell lines
(TCL) from 48 different ragweed pollen-allergic
patients (see Table 2). 121 overlapping synthetic
peptides (12-mer) were used for epitope mapping.
The relevance of each epitope was separately
evaluated for stimulation indexes higher than 3
(SI > 3) and higher than 5 (SI > 5).

| Peptide (=SEQ ID No.) | AA position | AA sequence | No. positive patients SI > 3 | % | No. positive patients SI > 5 | % |
|---|---|---|---|---|---|---|
| 86 | 280-291 | FGFFQVVNNNYD | 12 | 25.0 | 10 | 20.8 |
| 87 | 283-294 | FQVVNNNYDRWG | 5 | 10.4 | 2 | 4.2 |
| 88 | 286-297 | VNNNYDRWGTYA | 10 | 20.8 | 4 | 8.3 |
| 89 | 289-300 | NYDRWGTYAIGG | 11 | 22.9 | 6 | 12.5 |
| 90 | 292-303 | RWGTYAIGGSSA | 5 | 10.4 | 3 | 6.3 |
| 91 | 295-306 | TYAIGGSSAPTI | 13 | 27.1 | 11 | 22.9 |
| 92 | 298-309 | IGGSSAPTILCQ | 3 | 6.3 | 2 | 4.2 |
| 93 | 301-312 | SSAPTILCQGNR | 6 | 12.5 | 4 | 8.3 |
| 94 | 304-315 | PTILCQGNRFLA | 11 | 22.9 | 9 | 18.8 |
| 95 | 307-318 | LCQGNRFLAPDD | 0 | 0.0 | 0 | 0.0 |
| 96 | 310-321 | GNRFLAPDDQIK | 5 | 10.4 | 4 | 8.3 |
| 97 | 313-324 | FLAPDDQIKKNV | 6 | 12.5 | 4 | 8.3 |
| 98 | 316-327 | PDDQIKKNVLAR | 13 | 27.1 | 8 | 16.7 |
| 99 | 319-330 | QIKKNVLARTGT | 8 | 16.7 | 4 | 8.3 |
| 100 | 322-333 | KNVLARTGTGAA | 6 | 12.5 | 5 | 10.4 |
| 101 | 325-336 | LARTGTGAAESM | 10 | 20.8 | 7 | 14.6 |
| 102 | 328-339 | TGTGAAESMAWN | 9 | 18.8 | 6 | 12.5 |
| 103 | 331-342 | GAAESMAWNWRS | 2 | 4.2 | 1 | 2.1 |
| 104 | 334-345 | ESMAWNWRSDKD | 2 | 4.2 | 1 | 2.1 |
| 105 | 337-348 | AWNWRSDKDLLE | 4 | 8.3 | 3 | 6.3 |
| 106 | 340-351 | WRSDKDLLENGA | 3 | 6.3 | 1 | 2.1 |
| 107 | 343-354 | DKDLLENGAIFV | 30 | 62.5 | 27 | 56.3 |
| 108 | 346-357 | LLENGAIFVTSG | 27 | 56.3 | 24 | 50.0 |
| 109 | 349-360 | NGAIFVTSGSDP | 12 | 25.0 | 9 | 18.8 |
| 110 | 352-363 | IFVTSGSDPVLT | 13 | 27.1 | 11 | 22.9 |
| 111 | 355-366 | TSGSDPVLTPVQ | 16 | 33.3 | 11 | 22.9 |
| 112 | 358-369 | SDPVLTPVQSAG | 7 | 14.6 | 3 | 6.3 |
| 113 | 361-372 | VLTPVQSAGMIP | 4 | 8.3 | 1 | 2.1 |
| 114 | 364-375 | PVQSAGMIPAEP | 8 | 16.7 | 5 | 10.4 |
| 115 | 367-378 | SAGMIPAEPGEA | 18 | 37.5 | 17 | 35.4 |
| 116 | 370-381 | MIPAEPGEAAIK | 6 | 12.5 | 4 | 8.3 |
| 117 | 373-384 | AEPGEAAIKLTS | 4 | 8.3 | 3 | 6.3 |
| 118 | 376-387 | GEAAIKLTSSAG | 10 | 20.8 | 8 | 16.7 |
| 119 | 379-390 | AIKLTSSAGVLS | 16 | 33.3 | 10 | 20.8 |

TABLE 3-continued

T cell epitopes of Amb a 1-specific T cell lines
(TCL) from 48 different ragweed pollen-allergic
patients (see Table 2). 121 overlapping synthetic
peptides (12-mer) were used for epitope mapping.
The relevance of each epitope was separately
evaluated for stimulation indexes higher than 3
(SI > 3) and higher than 5 (SI > 5).

| Peptide (=SEQ ID No.) | AA position | AA sequence | No. positive patients SI > 3 | % | No. positive patients SI > 5 | % |
|---|---|---|---|---|---|---|
| 120 | 382-393 | LTSSAGVLSCRP | 14 | 29.2 | 9 | 18.8 |
| 121 | 385-397 | SAGVLSCRPGAPC | 6 | 12.5 | 2 | 4.2 |

Example 3

Characterization of Alpha and Beta Chains of Amb a 1 nAmb a 1 undergoes spontaneously proteolysis during purification and it is cleaved into two chains, alpha and beta chain, respectively. The data using sera collected from patients in various countries (Italy, Canada and Austria) showed that most patients (90%) strongly recognized the 12-kDa beta chain. In contrast, the alpha chain weakly bound IgE antibodies of only 65% of the patients tested (FIG. 9).

In experiments aiming at the identification of T cell epitopes (described in example 2) it was found that three T cell activating regions induced proliferative responses in more than 45% of the allergic patients and were thus defined as immunodominant epitopes (Table 3, FIG. 8). Interestingly, these and other T cell activating regions are clustered in the C-terminal region of Amb a 1, which corresponds to the alpha chain. Thus, contrary to early published research (King et al. Arch. Biochem. Biophys. 212: 127-135, 1981), the present collective data show that the immunologic properties of the two Amb a 1 chains differs. These findings incited to investigate the possibility to separately produce the chains in *E. coli* and use them as candidate vaccine for allergy diagnosis and immunotherapy. The alpha chain with the lower IgE binding capacity but with high immunogenicity (T cell activation) is a perfect tool for specific immunotherapy whereas the highly IgE reactive beta chain is a candidate for ragweed pollen allergy diagnosis.

For this purpose, experiments to determine the exact cleavage site for the generation of the alpha and beta chains were performed, which was described for Amb a 1 during its extraction and purification from ragweed pollen (King et al. Immunochem. 11: 83-92, 1974). Besides the estimation of its molecular weight by SDS-PAGE, no structural data has been published concerning the Amb a 1 chains. Purified natural Amb a 1 (see King et al. Immunochem. 11: 83-92, 1974) was analyzed by Maldi-TOF mass spectrometry and the bands corresponding to intact, alpha and beta chains of Amb a 1 were subjected to Edman-degradation after SDS-PAGE/electroblotting/Coomassie staining. In this way, it was possible to determine the exact masses and N-terminal sequences of processed and unprocessed natural Amb a 1 (FIGS. 10-13; Table 4).

Example 3.1

N-terminal Sequence Analysis

Natural Amb a 1 was separated by 15% SDS-PAGE and electroblotted onto polyvinyl difluoride (PVDF) membranes (Millipore). Bands corresponding to Amb a 1 and its fragments were excised, and proteins were eluted by incubation in aqueous 40% (v/v) acetonitrile and 30% (v/v) trifluoroacetic acid for 1 hour at room temperature. Samples were vacuum dried, resuspended in water, and sequenced with the HP G1005A protein sequencing system (Agilent Technologies).

Example 3.2

Matrix-Assisted Laser Desorption/Ionization Time-of-Flight (MALDI-TOF) Mass Spectrometry The molecular peaks of sinapinic acid and bovine pancreas trypsin were used for calibration. 0.5 µl (~0.7 µg) of purified natural Amb a 1 protein solution in the presence of 100 mM DTT and 0.5 µl of a sinapinic acid matrix were dissolved in a saturated solution of 50% (v/v) acetonitrile and 0.1% (v/v) trifluoracetic acid (TFA), mixed, and applied to the target slide. Samples were analyzed with the Kompact MALDI-TOF IV mass spectrometer (Shimadzu) in the linear flight mode.

Example 3.3

Results

Taken together, the data (FIGS. 10-13; Table 4) allowed the exact mapping of the alpha and beta chains into the deduced amino acid sequence of Amb a 1 and indicated that several proteolytic steps are involved in their generation:

(i) N-terminal sequencing of the unprocessed Amb a 1 showed that 17-20 amino acids are removed from the N-terminus of the protein.

(ii) The beta chain is 138 amino acids-long and corresponds to the N-terminal part of Amb a 1 (amino acid position 18 to 155 of the mature protein, taking Amb a 1.1 isoform as template).

(iii) The alpha chain is 207 amino acids-long and corresponds to the C-terminal part of Amb a 1 (amino acid position 165 to 371 of the mature protein, taking Amb a 1.1 isoform as template).

(iv) Nine amino acids are removed between the C-terminus of the beta chain and the N-terminus of the alpha chain.

FIG. 14 shows the deduced amino acid sequences of Amb a 1 isoforms with the putative alpha and beta chains mapped onto their sequences.

TABLE 4

Mass spectrometry analysis of natural Amb a 1

| | Unprocessed Amb a 1 | | Amb a 1 alpha chain | | Amb a 1 beta chain | |
|---|---|---|---|---|---|---|
| | Calculated | Measured | Calculated | Measured | Calculated | Measured |
| nAmb a 1 | | 37,832.14 | | 21,808.54 | | 15,086.31 |
| | | | | 22,323.24 | | |
| Amb a 1.1 | 37,864.43 | | 21,999.50 | | 15,017.04 | |
| Amb a 1.2 | 38,625.71 | | 22,425.10 | | 15,268.56 | |
| Amb a 1.3 | 38,255.30 | | 22,036.77 | | 15,286.49 | |
| Amb a 1.4 | 38,008.93 | | 21,953.62 | | 15,130.29 | |
| Amb a 2 | 39,392.56 | | 22,921.76 | | 15,638.88 | |

Example 4

Recombinant Production of Amb a 1.3 Alpha and Beta Chains

Example 4.1

Construction of Expression Plasmids and Purification of Amb a 1.3 Alpha and Beta Chains Designed According to Naturally Processed Chains Plasmid construction and purification of chains were performed as described in example 4.2. The differences in the chains are depicted in FIG. 16. Table 5 summarizes the different constructs for the recombinant production of alpha and beta chains.

Example 4.2

Recombinant Production of Modified (Version 1) Alpha and Beta Chains of Amb a 1.3

The present experiments demonstrated that the separate production of the modified chains is much more effective than the production of the full-length Amb a 1.3 molecule. The production yield of the alpha chain was approximately 100 mg/1 L fermentation culture. In addition, no significant formation of aggregates for both alpha and beta chains were observed (FIG. 18).

Example 4.2.1

Plasmid Construction

From the original R2 clone a 100 µl Standard PCR with primers designed according to the modified chains was performed. PCR products were eluted from agarose gel with Wizard Gene clean up (Promega). Both primer sets (for beta and alpha) included a NcoI site at the 5' and a stop codon plus XhoI site at the 3' end. With these enzymes the PCR fragments and the vector pHisparallel-2 were digested overnight at 37° C. After elution from the agarose gel (Wizard Gene clean up, Promega), the PCR fragments were ligated into the vector using a standard ligation protocol with T4 DNA ligase (Invitrogen). The ligation reaction was used to transform the bacterial strain TG1 (K12, D(lac-pro), supE, thi, hsdD5/F' [traD36, proA+B+, lacIq, lacZDM15]) via electroporation. After plating 100 µl of the transformation, the LBamp agar plates were incubated overnight at 37° C. PCR colony screening was used to select positive clones. (Small amount of bacterial colony is used as template for standard PCR with cloning primer). Selected clones were used for 50 ml SB cultures and plasmids purification. Inserts were sequenced with ABI sequencing kit. Plasmids with correct sequence were used to transform bacterial strains BL21 and Rosetta-gami B (DE3) pLysS (Novagen). Preliminary experiments showed that higher expression levels were achieved with the Rosetta-gami B (DE3) pLysS E. coli strain (FIG. 17).

Example 4.2.2

Expression and Purification of Modified (Version 1) Amb a 1.3 Alpha and Beta Chains 10-20 clones from freshly transformed bacteria were grown in SB to $OD_{600}$ of 0.5-0.7 and then induced with 0.4 mM IPTG. The expression was performed for 4-5 h and then the culture was pelleted by centrifugation (5,000 g). Bacterial pellet was resuspended in start buffer (25 mM Na-phosphat pH 8.0; 1M NaCl). Cells were lysed by 3× freezing in liquid nitrogen and thawing at 25° C. The suspension was treated with lysozyme (5 mg/ml), Dnase (0.5 µg/ml) and sonicated for 5 minutes. After centrifugation (15,000 g) the pellets were resuspended in urea start buffer (start buffer+6M Urea+10 mM imidazole). After centrifugation (15,000 g), the supernatant was loaded onto a HisTrap $Ni^{2+}$ column (Amersham). Elution was performed by gradient with Elution buffer (Urea start buffer+400 mM imidazole). Fractions were pooled and dialysed 3 times against 500 mM L-Arg pH 8.5. Afterwards, proteins were dialysed against PBS. Purified Amb a 1.3 alpha and beta chains (FIG. 18) were used for IgE binding and T cell proliferation assays.

Example 4.2.3

T Cell Responses to Modified (Version 1) Alpha and Beta Chains of Amb a 1.3

When compared with the results of the T cell epitope recognition in Table 3, 45/46 patients (98%) would recognize one or more epitopes in the Amb a 1 alpha-chain. Thus, the T cell responses to modified (version 1) alpha and beta chains of Amb a 1.3 was tested in proliferation assays using available Amb a 1-reactive TCL (n=6) and TCC (n=2), described in example 2.

Example 4.3

Recombinant Production

The production of alpha and beta chains designed according to naturally processed Amb a 1 were not very encouraging, with very low yields. However, data obtained from T cell epitope mapping experiments indicated that one important epitope was not included in the alpha chain, which harbours most of the T cell reactive domains (FIG. 16; aa 178-189). Therefore, new chains were designed to include this T cell epitope (Table 5, FIG. 16).

Example 4.4

IgE Binding

As shown in example 3, the naturally processed alpha and beta chains of Amb a 1 have distinct immunological properties. The alpha chain shows low IgE reactivity whereas the beta chain contains most of the IgE epitopes of Amb a 1. Therefore, to test the IgE-binding activity of the purified alpha chain, ELISA with sera from ragweed allergic patients was performed. Results from 12 patients confirmed that the alpha chain shows low/no IgE-binding activity in vitro (FIG. 19). Experiments are being carried out for the purification and characterization of the beta chain.

Example 4.5

T Cell Reactivity

Of 6 TCL tested, 2 TCL with strong reactivity to Amb a 1 are shown in FIG. 20. The alpha chain was much more effective in stimulating proliferation than the beta-chain (82% and 84% vs. 38 and 19% of the response to Amb a 1). This finding can be explained by the epitope recognition pattern of these 2 TCL (see Table 2). Two other TCL (FIG. 21) also reacted with the alpha and/or the beta chain according to their epitope profile.

2 TCC specific for epitopes within Amb a 1-alpha reacted with the alpha but not with the beta chain, albeit not as strong as with Amb a 1.3.

TABLE 5

Amb a 1.3 chains

| Amb a 1.3 chains | | Amino acid position | Length |
|---|---|---|---|
| Naturally processed | alpha | 191-397 | 207 amino acids |
| | beta | 44-181 | 138 amino acids |
| Design according to naturally processed | alpha | 191-397 | 208 amino acids |
| | beta | 26-190 | 164 amino acids |
| Modified (version 1) | alpha | 174-397 | 224 amino acids |
| | beta | 26-173 | 148 amino acids |
| Modified (version 2) | alpha | 174-397 | 224 amino acids |
| | beta | 46-173 | 128 amino acids |

Summary:

In summary, 26 relevant T cell activating regions of Amb a 1 were identified taking a SI>5 as threshold for positivity (FIGS. 8 and 22).

In the analysis of T cell epitopes recognized by T cell lines from 48 different patients it was found that 17/26 epitopes are located in the C-terminal region of Amb a 1.3 (alpha chain) whereas the beta chain contains only a few T cell epitopes that are mostly recognized by only 10-30% of the patients (FIG. 8, Table 3).

However, one relevant/immunodominant T cell epitope sequence recognized by more than 50% of the patients is cleaved off in the naturally occurring chains (would only partly be represented in the alpha chain). In order to cover this important T cell activating region, the invention includes the modification of the alpha chain by adding 16 amino acid residues from the C-terminus of the beta chain to the N-terminus of the alpha chain (modified version 1; FIG. 16, Table 5). Thus, the modified (version 1) construct of the Amb a 1.3 alpha chain includes the 3 most frequently recognized T cell epitopes of Amb a 1 (FIG. 22).

The use of the entire alpha chain of Amb a 1.3 (modified version 1) as a vaccine for ragweed pollen-allergy would cover 100% of the patients tested (n=48).

The use of a combination of the three immunodominant T cell epitopes identified here for peptide immunotherapy of ragweed pollen-allergic patients would cover 93% of the patients:

```
                                   (Peptide 52; SEQ ID No. 52)
    GMIKSNDGPPIL (Peptide 60-61; SEQ ID No. 137)
    GSSQITWIDHCSLSKS (Peptide 107-111; SEQ ID No. 138)
    DKDLLENGAIFVTSGSDPVLTPVQ
```

The following mixture of 4 peptides would cover 95.8% of the patients:

```
                                   (Peptide 52; SEQ ID No. 52)
    GMIKSNDGPPIL (Peptide 60-61; SEQ ID No. 137)
    GSSQIWIDHCSLSKS (Peptide 107-111; SEQ ID No. 138)
    DKDLLENGAIFVTSGSDPVLTPVQ (Peptide 119-120; SEQ ID No. 139)
    AIKLTSSAGVLSCRP
```

The addition of the following frequently recognized peptides to this optimum peptide combination could also be considered:

```
                                (Peptide 46-48; SEQ ID No. 130)
    KNIIIHNTNIHDVKVLPG (Peptide 68; SEQ ID No. 68)
    GSTHVTISNCKF (Peptide 115; SEQ ID No. 115)
    SAGMIPAEPGEA
```

The invention claimed is:

1. A pharmaceutical composition, comprising a peptide consisting of the amino acid sequence of SEQ ID NO: 52.

2. The pharmaceutical composition of claim 1, further comprising at least one pharmaceutically acceptable adjuvant, excipient, or carrier.

3. A ragweed pollen allergen Amb a 1 peptide, consisting of the amino acid sequence of SEQ ID NO: 52.

4. A molecule, consisting of
a peptide consisting of the amino acid sequence of SEQ ID NO: 52; and
a peptide consisting of the amino acid sequence selected from the group consisting of SEQ ID No: 12, SEQ ID No: 20, SEQ ID No: 27, SEQ ID No: 28, SEQ ID No: 30, SEQ ID No: 31, SEQ ID No: 33, SEQ ID No: 36, SEQ ID No: 37, SEQ ID No: 38, SEQ ID No: 39, SEQ ID No: 41, SEQ ID No: 42, SEQ ID No: 44, SEQ ID No: 46, SEQ ID No: 47, SEQ ID No: 48, SEQ ID No: 50, SEQ ID No: 51, SEQ ID No: 53, SEQ ID No: 59, SEQ ID No: 60, SEQ ID No: 61, SEQ ID No: 67, SEQ ID No: 68, SEQ ID No: 69, SEQ ID No: 77, SEQ ID No: 78, SEQ ID No: 79, SEQ ID No: 80, SEQ ID No: 81, SEQ ID No: 83, SEQ ID No: 86, SEQ ID No: 87, SEQ ID No: 88, SEQ ID No: 89, SEQ ID No: 90, SEQ ID No: 91, SEQ ID No: 93, SEQ ID No: 94, SEQ ID No: 96, SEQ ID No: 97, SEQ ID No: 98, SEQ ID No: 99, SEQ ID No: 100, SEQ ID No: 101, SEQ ID No: 102, SEQ ID No: 107, SEQ ID No: 108, SEQ ID No: 109, SEQ ID No: 110, SEQ ID No: 111, SEQ ID No: 112, SEQ ID No: 114, SEQ ID No: 115, SEQ ID No: 118, SEQ ID No: 119, SEQ ID No: 120, SEQ ID No: 121, SEQ ID No: 122, SEQ ID No: 123, SEQ ID No: 124, SEQ ID No: 125, SEQ ID No: 126, SEQ ID No: 127, SEQ ID No: 128, SEQ ID No: 129, SEQ ID No: 130, SEQ ID No: 131, SEQ ID No: 132, SEQ ID No: 133, SEQ ID No: 134, SEQ ID No: 135, SEQ ID No: 136, SEQ ID No: 137, SEQ ID No: 138, and SEQ ID No: 139.

5. A pharmaceutical composition, comprising the molecule of claim 4.

6. The pharmaceutical composition of claim 5, further comprising at least one pharmaceutically acceptable adjuvant, excipient, or carrier.

7. The pharmaceutical composition of claim 1, further comprising at least one peptide consisting of the amino acid sequence selected from the group consisting of SEQ ID NO: 69, SEQ ID NO: 86, SEQ ID NO: 91, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, and SEQ ID NO: 139.

8. A molecule consisting of (i) SEQ ID NO:52 and SEQ ID NO: 137; (ii) SEQ ID NO: 52 and SEQ ID NO:138; (iii) SEQ ID NO: 52 and SEQ ID NO: 139; (iv) SEQ ID NO: 52, SEQ ID NO: 137 and SEQ ID NO: 138; (v) SEQ ID NO: 52, SEQ ID NO: 137 and SEQ ID NO: 139; (vi) SEQ ID NO: 52, SEQ ID NO: 138 and a SEQ ID NO: 139; or (vii) SEQ ID NO: 52, SEQ ID NO: 137, SEQ ID NO: 138 and SEQ ID NO: 139.

9. The pharmaceutical composition of claim 1, further comprising the peptide of SEQ ID NO:137.

10. The pharmaceutical composition of claim 1, wherein the peptide is present in an amount of 0.05 µg to 1000 µg.

11. The pharmaceutical composition of claim 1, which is in lyophilized.

12. The pharmaceutical composition of claim 5, wherein the molecule is present in an amount of 0.05 µg to 1000 µg.

13. The pharmaceutical composition of claim 5, which is lyophilized.

* * * * *

SEQUENCE LISTING

<160> NUMBER OF SEQ ID NOS: 145

<210> SEQ ID NO 1
<211> LENGTH: 12
<212> TYPE: PRT
<213> ORGANISM: Artificial

<220> FEATURE:
<223> OTHER INFORMATION: Amb a 1 fragment

<400> SEQUENCE: 1

```
Ser Ala Glu Gly Val Gly Glu Ile Leu Pro Ser Val
1               5                   10
```

<210> SEQ ID NO 2
<211> LENGTH: 12
<212> TYPE: PRT
<213> ORGANISM: Artificial
<220> FEATURE:
<223> OTHER INFORMATION: Amb a 1 fragment

<400> SEQUENCE: 2

```
Gly Val Gly Glu Ile Leu Pro Ser Val Asn Glu Thr
1               5                   10
```

<210> SEQ ID NO 3
<211> LENGTH: 12
<212> TYPE: PRT
<213> ORGANISM: Artificial
<220> FEATURE:
<223> OTHER INFORMATION: Amb a 1 fragment

<400> SEQUENCE: 3

```
Glu Ile Leu Pro Ser Val Asn Glu Thr Arg Ser Leu
1               5                   10
```

<210> SEQ ID NO 4
<211> LENGTH: 12
<212> TYPE: PRT
<213> ORGANISM: Artificial
<220> FEATURE:
<223> OTHER INFORMATION: Amb a 1 fragment

<400> SEQUENCE: 4

```
Pro Ser Val Asn Glu Thr Arg Ser Leu Gln Ala Cys
1               5                   10

```

<210> SEQ ID NO 5
<211> LENGTH: 12
<212> TYPE: PRT
<213> ORGANISM: Artificial
<220> FEATURE:
<223> OTHER INFORMATION: Amb a 1 fragment

<400> SEQUENCE: 5

```
Asn Glu Thr Arg Ser Leu Gln Ala Cys Glu Ala Tyr
1               5                   10
```

<210> SEQ ID NO 6
<211> LENGTH: 12
<212> TYPE: PRT
<213> ORGANISM: Artificial
<220> FEATURE:
<223> OTHER INFORMATION: Amb a 1 fragment

<400> SEQUENCE: 6

```
Arg Ser Leu Gln Ala Cys Glu Ala Tyr Asn Ile Ile
1               5                   10
```

<210> SEQ ID NO 7
<211> LENGTH: 12
<212> TYPE: PRT
<213> ORGANISM: Artificial

```
<220> FEATURE:
<223> OTHER INFORMATION: Amb a 1 fragment

<400> SEQUENCE: 7

Gln Ala Cys Glu Ala Tyr Asn Ile Ile Asp Lys Cys
1               5                   10

<210> SEQ ID NO 8
<211> LENGTH: 12
<212> TYPE: PRT
<213> ORGANISM: Artificial
<220> FEATURE:
<223> OTHER INFORMATION: Amb a 1 fragment

<400> SEQUENCE: 8

Glu Ala Tyr Asn Ile Ile Asp Lys Cys Trp Arg Gly
1               5                   10

<210> SEQ ID NO 9
<211> LENGTH: 12
<212> TYPE: PRT
<213> ORGANISM: Artificial
<220> FEATURE:
<223> OTHER INFORMATION: Amb a 1 fragment

<400> SEQUENCE: 9

Asn Ile Ile Asp Lys Cys Trp Arg Gly Lys Ala Asp
1               5                   10

<210> SEQ ID NO 10
<211> LENGTH: 12
<212> TYPE: PRT
<213> ORGANISM: Artificial
<220> FEATURE:
<223> OTHER INFORMATION: Amb a 1 fragment

<400> SEQUENCE: 10

Asp Lys Cys Trp Arg Gly Lys Ala Asp Trp Glu Asn
1               5                   10

<210> SEQ ID NO 11
<211> LENGTH: 12
<212> TYPE: PRT
<213> ORGANISM: Artificial
<220> FEATURE:
<223> OTHER INFORMATION: Amb a 1 fragment

<400> SEQUENCE: 11

Trp Arg Gly Lys Ala Asp Trp Glu Asn Asn Arg Gln
1               5                   10

<210> SEQ ID NO 12
<211> LENGTH: 12
<212> TYPE: PRT
<213> ORGANISM: Artificial
<220> FEATURE:
<223> OTHER INFORMATION: Amb a 1 fragment

<400> SEQUENCE: 12

Lys Ala Asp Trp Glu Asn Asn Arg Gln Ala Leu Ala
1               5                   10

<210> SEQ ID NO 13
<211> LENGTH: 12
<212> TYPE: PRT
<213> ORGANISM: Artificial
```

```
<220> FEATURE:
<223> OTHER INFORMATION: Amb a 1 fragment

<400> SEQUENCE: 13

Trp Glu Asn Asn Arg Gln Ala Leu Ala Asp Cys Ala
1               5                   10

<210> SEQ ID NO 14
<211> LENGTH: 12
<212> TYPE: PRT
<213> ORGANISM: Artificial
<220> FEATURE:
<223> OTHER INFORMATION: Amb a 1 fragment

<400> SEQUENCE: 14

Asn Arg Gln Ala Leu Ala Asp Cys Ala Gln Gly Phe
1               5                   10

<210> SEQ ID NO 15
<211> LENGTH: 12
<212> TYPE: PRT
<213> ORGANISM: Artificial
<220> FEATURE:
<223> OTHER INFORMATION: Amb a 1 fragment

<400> SEQUENCE: 15

Ala Leu Ala Asp Cys Ala Gln Gly Phe Ala Lys Gly
1               5                   10

<210> SEQ ID NO 16
<211> LENGTH: 12
<212> TYPE: PRT
<213> ORGANISM: Artificial
<220> FEATURE:
<223> OTHER INFORMATION: Amb a 1 fragment

<400> SEQUENCE: 16

Asp Cys Ala Gln Gly Phe Ala Lys Gly Thr Tyr Gly
1               5                   10

<210> SEQ ID NO 17
<211> LENGTH: 12
<212> TYPE: PRT
<213> ORGANISM: Artificial
<220> FEATURE:
<223> OTHER INFORMATION: Amb a 1 fragment

<400> SEQUENCE: 17

Gln Gly Phe Ala Lys Gly Thr Tyr Gly Gly Lys Trp
1               5                   10

<210> SEQ ID NO 18
<211> LENGTH: 12
<212> TYPE: PRT
<213> ORGANISM: Artificial
<220> FEATURE:
<223> OTHER INFORMATION: Amb a 1 fragment

<400> SEQUENCE: 18

Ala Lys Gly Thr Tyr Gly Gly Lys Trp Gly Asp Val
1               5                   10

<210> SEQ ID NO 19
<211> LENGTH: 12
<212> TYPE: PRT
<213> ORGANISM: Artificial
<220> FEATURE:
```

```
<223> OTHER INFORMATION: Amb a 1 fragment

<400> SEQUENCE: 19

Thr Tyr Gly Gly Lys Trp Gly Asp Val Tyr Thr Val
1               5                   10

<210> SEQ ID NO 20
<211> LENGTH: 12
<212> TYPE: PRT
<213> ORGANISM: Artificial
<220> FEATURE:
<223> OTHER INFORMATION: Amb a 1 fragment

<400> SEQUENCE: 20

Gly Lys Trp Gly Asp Val Tyr Thr Val Thr Ser Asn
1               5                   10

<210> SEQ ID NO 21
<211> LENGTH: 12
<212> TYPE: PRT
<213> ORGANISM: Artificial
<220> FEATURE:
<223> OTHER INFORMATION: Amb a 1 fragment

<400> SEQUENCE: 21

Gly Asp Val Tyr Thr Val Thr Ser Asn Leu Asp Asp
1               5                   10

<210> SEQ ID NO 22
<211> LENGTH: 12
<212> TYPE: PRT
<213> ORGANISM: Artificial
<220> FEATURE:
<223> OTHER INFORMATION: Amb a 1 fragment

<400> SEQUENCE: 22

Tyr Thr Val Thr Ser Asn Leu Asp Asp Val Ala
1               5                   10

<210> SEQ ID NO 23
<211> LENGTH: 12
<212> TYPE: PRT
<213> ORGANISM: Artificial
<220> FEATURE:
<223> OTHER INFORMATION: Amb a 1 fragment

<400> SEQUENCE: 23

Thr Ser Asn Leu Asp Asp Val Ala Asn Pro Lys
1               5                   10

<210> SEQ ID NO 24
<211> LENGTH: 12
<212> TYPE: PRT
<213> ORGANISM: Artificial
<220> FEATURE:
<223> OTHER INFORMATION: Amb a 1 fragment

<400> SEQUENCE: 24

Leu Asp Asp Val Ala Asn Pro Lys Glu Gly Thr
1               5                   10

<210> SEQ ID NO 25
<211> LENGTH: 12
<212> TYPE: PRT
<213> ORGANISM: Artificial
<220> FEATURE:
<223> OTHER INFORMATION: Amb a 1 fragment
```

```
<400> SEQUENCE: 25

Asp Val Ala Asn Pro Lys Glu Gly Thr Leu Arg Phe
1               5                   10

<210> SEQ ID NO 26
<211> LENGTH: 12
<212> TYPE: PRT
<213> ORGANISM: Artificial
<220> FEATURE:
<223> OTHER INFORMATION: Amb a 1 fragment

<400> SEQUENCE: 26

Asn Pro Lys Glu Gly Thr Leu Arg Phe Ala Ala Ala
1               5                   10

<210> SEQ ID NO 27
<211> LENGTH: 12
<212> TYPE: PRT
<213> ORGANISM: Artificial
<220> FEATURE:
<223> OTHER INFORMATION: Amb a 1 fragment

<400> SEQUENCE: 27

Glu Gly Thr Leu Arg Phe Ala Ala Ala Gln Asn Arg
1               5                   10

<210> SEQ ID NO 28
<211> LENGTH: 12
<212> TYPE: PRT
<213> ORGANISM: Artificial
<220> FEATURE:
<223> OTHER INFORMATION: Amb a 1 fragment

<400> SEQUENCE: 28

Leu Arg Phe Ala Ala Ala Gln Asn Arg Pro Leu Trp
1               5                   10

<210> SEQ ID NO 29
<211> LENGTH: 12
<212> TYPE: PRT
<213> ORGANISM: Artificial
<220> FEATURE:
<223> OTHER INFORMATION: Amb a 1 fragment

<400> SEQUENCE: 29

Ala Ala Ala Gln Asn Arg Pro Leu Trp Ile Ile Phe
1               5                   10

<210> SEQ ID NO 30
<211> LENGTH: 12
<212> TYPE: PRT
<213> ORGANISM: Artificial
<220> FEATURE:
<223> OTHER INFORMATION: Amb a 1 fragment

<400> SEQUENCE: 30

Gln Asn Arg Pro Leu Trp Ile Ile Phe Lys Asn Asp
1               5                   10

<210> SEQ ID NO 31
<211> LENGTH: 12
<212> TYPE: PRT
<213> ORGANISM: Artificial
<220> FEATURE:
<223> OTHER INFORMATION: Amb a 1 fragment
```

```
<400> SEQUENCE: 31

Pro Leu Trp Ile Ile Phe Lys Asn Asp Met Val Ile
1               5                   10

<210> SEQ ID NO 32
<211> LENGTH: 12
<212> TYPE: PRT
<213> ORGANISM: Artificial
<220> FEATURE:
<223> OTHER INFORMATION: Amb a 1 fragment

<400> SEQUENCE: 32

Ile Ile Phe Lys Asn Asp Met Val Ile Asn Leu Asn
1               5                   10

<210> SEQ ID NO 33
<211> LENGTH: 12
<212> TYPE: PRT
<213> ORGANISM: Artificial
<220> FEATURE:
<223> OTHER INFORMATION: Amb a 1 fragment

<400> SEQUENCE: 33

Lys Asn Asp Met Val Ile Asn Leu Asn Gln Glu Leu
1               5                   10

<210> SEQ ID NO 34
<211> LENGTH: 12
<212> TYPE: PRT
<213> ORGANISM: Artificial
<220> FEATURE:
<223> OTHER INFORMATION: Amb a 1 fragment

<400> SEQUENCE: 34

Met Val Ile Asn Leu Asn Gln Glu Leu Val Val Asn
1               5                   10

<210> SEQ ID NO 35
<211> LENGTH: 12
<212> TYPE: PRT
<213> ORGANISM: Artificial
<220> FEATURE:
<223> OTHER INFORMATION: Amb a 1 fragment

<400> SEQUENCE: 35

Asn Leu Asn Gln Glu Leu Val Val Asn Ser Asp Lys
1               5                   10

<210> SEQ ID NO 36
<211> LENGTH: 12
<212> TYPE: PRT
<213> ORGANISM: Artificial
<220> FEATURE:
<223> OTHER INFORMATION: Amb a 1 fragment

<400> SEQUENCE: 36

Gln Glu Leu Val Val Asn Ser Asp Lys Thr Ile Asp
1               5                   10

<210> SEQ ID NO 37
<211> LENGTH: 12
<212> TYPE: PRT
<213> ORGANISM: Artificial
<220> FEATURE:
<223> OTHER INFORMATION: Amb a 1 fragment

<400> SEQUENCE: 37
```

Val Val Asn Ser Asp Lys Thr Ile Asp Gly Arg Gly
1               5                   10

<210> SEQ ID NO 38
<211> LENGTH: 12
<212> TYPE: PRT
<213> ORGANISM: Artificial
<220> FEATURE:
<223> OTHER INFORMATION: Amb a 1 fragment

<400> SEQUENCE: 38

Ser Asp Lys Thr Ile Asp Gly Arg Gly Val Lys Val
1               5                   10

<210> SEQ ID NO 39
<211> LENGTH: 12
<212> TYPE: PRT
<213> ORGANISM: Artificial
<220> FEATURE:
<223> OTHER INFORMATION: Amb a 1 fragment

<400> SEQUENCE: 39

Thr Ile Asp Gly Arg Gly Val Lys Val Glu Ile Ile
1               5                   10

<210> SEQ ID NO 40
<211> LENGTH: 12
<212> TYPE: PRT
<213> ORGANISM: Artificial
<220> FEATURE:
<223> OTHER INFORMATION: Amb a 1 fragment

<400> SEQUENCE: 40

Gly Arg Gly Val Lys Val Glu Ile Ile Asn Gly Gly
1               5                   10

<210> SEQ ID NO 41
<211> LENGTH: 12
<212> TYPE: PRT
<213> ORGANISM: Artificial
<220> FEATURE:
<223> OTHER INFORMATION: Amb a 1 fragment

<400> SEQUENCE: 41

Val Lys Val Glu Ile Ile Asn Gly Gly Leu Thr Leu
1               5                   10

<210> SEQ ID NO 42
<211> LENGTH: 12
<212> TYPE: PRT
<213> ORGANISM: Artificial
<220> FEATURE:
<223> OTHER INFORMATION: Amb a 1 fragment

<400> SEQUENCE: 42

Glu Ile Ile Asn Gly Gly Leu Thr Leu Met Asn Val
1               5                   10

<210> SEQ ID NO 43
<211> LENGTH: 12
<212> TYPE: PRT
<213> ORGANISM: Artificial
<220> FEATURE:
<223> OTHER INFORMATION: Amb a 1 fragment

<400> SEQUENCE: 43

```
Asn Gly Gly Leu Thr Leu Met Asn Val Lys Asn Ile
1               5                   10
```

<210> SEQ ID NO 44
<211> LENGTH: 12
<212> TYPE: PRT
<213> ORGANISM: Artificial
<220> FEATURE:
<223> OTHER INFORMATION: Amb a 1 fragment

<400> SEQUENCE: 44

```
Leu Thr Leu Met Asn Val Lys Asn Ile Ile Ile His
1               5                   10
```

<210> SEQ ID NO 45
<211> LENGTH: 12
<212> TYPE: PRT
<213> ORGANISM: Artificial
<220> FEATURE:
<223> OTHER INFORMATION: Amb a 1 fragment

<400> SEQUENCE: 45

```
Met Asn Val Lys Asn Ile Ile Ile His Asn Ile Asn
1               5                   10
```

<210> SEQ ID NO 46
<211> LENGTH: 12
<212> TYPE: PRT
<213> ORGANISM: Artificial
<220> FEATURE:
<223> OTHER INFORMATION: Amb a 1 fragment

<400> SEQUENCE: 46

```
Lys Asn Ile Ile Ile His Asn Ile Asn Ile His Asp
1               5                   10
```

<210> SEQ ID NO 47
<211> LENGTH: 12
<212> TYPE: PRT
<213> ORGANISM: Artificial
<220> FEATURE:
<223> OTHER INFORMATION: Amb a 1 fragment

<400> SEQUENCE: 47

```
Ile Ile His Asn Ile Asn Ile His Asp Val Lys Val
1               5                   10
```

<210> SEQ ID NO 48
<211> LENGTH: 12
<212> TYPE: PRT
<213> ORGANISM: Artificial
<220> FEATURE:
<223> OTHER INFORMATION: Amb a 1 fragment

<400> SEQUENCE: 48

```
Asn Ile Asn Ile His Asp Val Lys Val Leu Pro Gly
1               5                   10
```

<210> SEQ ID NO 49
<211> LENGTH: 12
<212> TYPE: PRT
<213> ORGANISM: Artificial
<220> FEATURE:
<223> OTHER INFORMATION: Amb a 1 fragment

<400> SEQUENCE: 49

```
Ile His Asp Val Lys Val Leu Pro Gly Gly Met Ile
```

```
<210> SEQ ID NO 50
<211> LENGTH: 12
<212> TYPE: PRT
<213> ORGANISM: Artificial
<220> FEATURE:
<223> OTHER INFORMATION: Amb a 1 fragment

<400> SEQUENCE: 50

Val Lys Val Leu Pro Gly Gly Met Ile Lys Ser Asn
1               5                   10

<210> SEQ ID NO 51
<211> LENGTH: 12
<212> TYPE: PRT
<213> ORGANISM: Artificial
<220> FEATURE:
<223> OTHER INFORMATION: Amb a 1 fragment

<400> SEQUENCE: 51

Leu Pro Gly Gly Met Ile Lys Ser Asn Asp Gly Pro
1               5                   10

<210> SEQ ID NO 52
<211> LENGTH: 12
<212> TYPE: PRT
<213> ORGANISM: Artificial
<220> FEATURE:
<223> OTHER INFORMATION: Amb a 1 fragment

<400> SEQUENCE: 52

Gly Met Ile Lys Ser Asn Asp Gly Pro Pro Ile Leu
1               5                   10

<210> SEQ ID NO 53
<211> LENGTH: 12
<212> TYPE: PRT
<213> ORGANISM: Artificial
<220> FEATURE:
<223> OTHER INFORMATION: Amb a 1 fragment

<400> SEQUENCE: 53

Lys Ser Asn Asp Gly Pro Pro Ile Leu Arg Gln Ala
1               5                   10

<210> SEQ ID NO 54
<211> LENGTH: 12
<212> TYPE: PRT
<213> ORGANISM: Artificial
<220> FEATURE:
<223> OTHER INFORMATION: Amb a 1 fragment

<400> SEQUENCE: 54

Asp Gly Pro Pro Ile Leu Arg Gln Ala Ser Asp Gly
1               5                   10

<210> SEQ ID NO 55
<211> LENGTH: 12
<212> TYPE: PRT
<213> ORGANISM: Artificial
<220> FEATURE:
<223> OTHER INFORMATION: Amb a 1 fragment

<400> SEQUENCE: 55

Pro Ile Leu Arg Gln Ala Ser Asp Gly Asp Thr Ile
1               5                   10
```

<210> SEQ ID NO 56
<211> LENGTH: 12
<212> TYPE: PRT
<213> ORGANISM: Artificial
<220> FEATURE:
<223> OTHER INFORMATION: Amb a 1 fragment

<400> SEQUENCE: 56

Arg Gln Ala Ser Asp Gly Asp Thr Ile Asn Val Ala
1               5                   10

<210> SEQ ID NO 57
<211> LENGTH: 12
<212> TYPE: PRT
<213> ORGANISM: Artificial
<220> FEATURE:
<223> OTHER INFORMATION: Amb a 1 fragment

<400> SEQUENCE: 57

Ser Asp Gly Asp Thr Ile Asn Val Ala Gly Ser Ser
1               5                   10

<210> SEQ ID NO 58
<211> LENGTH: 12
<212> TYPE: PRT
<213> ORGANISM: Artificial
<220> FEATURE:
<223> OTHER INFORMATION: Amb a 1 fragment

<400> SEQUENCE: 58

Asp Thr Ile Asn Val Ala Gly Ser Ser Gln Ile Trp
1               5                   10

<210> SEQ ID NO 59
<211> LENGTH: 12
<212> TYPE: PRT
<213> ORGANISM: Artificial
<220> FEATURE:
<223> OTHER INFORMATION: Amb a 1 fragment

<400> SEQUENCE: 59

Asn Val Ala Gly Ser Ser Gln Ile Trp Ile Asp His
1               5                   10

<210> SEQ ID NO 60
<211> LENGTH: 12
<212> TYPE: PRT
<213> ORGANISM: Artificial
<220> FEATURE:
<223> OTHER INFORMATION: Amb a 1 fragment

<400> SEQUENCE: 60

Gly Ser Ser Gln Ile Trp Ile Asp His Cys Ser Leu
1               5                   10

<210> SEQ ID NO 61
<211> LENGTH: 12
<212> TYPE: PRT
<213> ORGANISM: Artificial
<220> FEATURE:
<223> OTHER INFORMATION: Amb a 1 fragment

<400> SEQUENCE: 61

Gln Ile Trp Ile Asp His Cys Ser Leu Ser Lys Ser
1               5                   10

<210> SEQ ID NO 62
<211> LENGTH: 12
<212> TYPE: PRT
<213> ORGANISM: Artificial
<220> FEATURE:
<223> OTHER INFORMATION: Amb a 1 fragment

<400> SEQUENCE: 62

Ile Asp His Cys Ser Leu Ser Lys Ser Phe Asp Gly
1               5                   10

<210> SEQ ID NO 63
<211> LENGTH: 12
<212> TYPE: PRT
<213> ORGANISM: Artificial
<220> FEATURE:
<223> OTHER INFORMATION: Amb a 1 fragment

<400> SEQUENCE: 63

Cys Ser Leu Ser Lys Ser Phe Asp Gly Leu Val Asp
1               5                   10

<210> SEQ ID NO 64
<211> LENGTH: 12
<212> TYPE: PRT
<213> ORGANISM: Artificial
<220> FEATURE:
<223> OTHER INFORMATION: Amb a 1 fragment

<400> SEQUENCE: 64

Ser Lys Ser Phe Asp Gly Leu Val Asp Val Thr Leu
1               5                   10

<210> SEQ ID NO 65
<211> LENGTH: 12
<212> TYPE: PRT
<213> ORGANISM: Artificial
<220> FEATURE:
<223> OTHER INFORMATION: Amb a 1 fragment

<400> SEQUENCE: 65

Phe Asp Gly Leu Val Asp Val Thr Leu Gly Ser Thr
1               5                   10

<210> SEQ ID NO 66
<211> LENGTH: 12
<212> TYPE: PRT
<213> ORGANISM: Artificial
<220> FEATURE:
<223> OTHER INFORMATION: Amb a 1 fragment

<400> SEQUENCE: 66

Leu Val Asp Val Thr Leu Gly Ser Thr His Val Thr
1               5                   10

<210> SEQ ID NO 67
<211> LENGTH: 12
<212> TYPE: PRT
<213> ORGANISM: Artificial
<220> FEATURE:
<223> OTHER INFORMATION: Amb a 1 fragment

<400> SEQUENCE: 67

Val Thr Leu Gly Ser Thr His Val Thr Ile Ser Asn
1               5                   10

```
<210> SEQ ID NO 68
<211> LENGTH: 12
<212> TYPE: PRT
<213> ORGANISM: Artificial
<220> FEATURE:
<223> OTHER INFORMATION: Amb a 1 fragment

<400> SEQUENCE: 68

Gly Ser Thr His Val Thr Ile Ser Asn Cys Lys Phe
1               5                   10

<210> SEQ ID NO 69
<211> LENGTH: 12
<212> TYPE: PRT
<213> ORGANISM: Artificial
<220> FEATURE:
<223> OTHER INFORMATION: Amb a 1 fragment

<400> SEQUENCE: 69

His Val Thr Ile Ser Asn Cys Lys Phe Thr Gln Gln
1               5                   10

<210> SEQ ID NO 70
<211> LENGTH: 12
<212> TYPE: PRT
<213> ORGANISM: Artificial
<220> FEATURE:
<223> OTHER INFORMATION: Amb a 1 fragment

<400> SEQUENCE: 70

Ile Ser Asn Cys Lys Phe Thr Gln Gln Ser Lys Ala
1               5                   10

<210> SEQ ID NO 71
<211> LENGTH: 12
<212> TYPE: PRT
<213> ORGANISM: Artificial
<220> FEATURE:
<223> OTHER INFORMATION: Amb a 1 fragment

<400> SEQUENCE: 71

Cys Lys Phe Thr Gln Gln Ser Lys Ala Ile Leu Leu
1               5                   10

<210> SEQ ID NO 72
<211> LENGTH: 12
<212> TYPE: PRT
<213> ORGANISM: Artificial
<220> FEATURE:
<223> OTHER INFORMATION: Amb a 1 fragment

<400> SEQUENCE: 72

Thr Gln Gln Ser Lys Ala Ile Leu Leu Gly Ala Asp
1               5                   10

<210> SEQ ID NO 73
<211> LENGTH: 12
<212> TYPE: PRT
<213> ORGANISM: Artificial
<220> FEATURE:
<223> OTHER INFORMATION: Amb a 1 fragment

<400> SEQUENCE: 73

Ser Lys Ala Ile Leu Leu Gly Ala Asp Asp Thr His
1               5                   10

<210> SEQ ID NO 74
```

```
<211> LENGTH: 12
<212> TYPE: PRT
<213> ORGANISM: Artificial
<220> FEATURE:
<223> OTHER INFORMATION: Amb a 1 fragment

<400> SEQUENCE: 74

Ile Leu Leu Gly Ala Asp Asp Thr His Val Gln Asp
1               5                   10

<210> SEQ ID NO 75
<211> LENGTH: 12
<212> TYPE: PRT
<213> ORGANISM: Artificial
<220> FEATURE:
<223> OTHER INFORMATION: Amb a 1 fragment

<400> SEQUENCE: 75

Gly Ala Asp Asp Thr His Val Gln Asp Lys Gly Met
1               5                   10

<210> SEQ ID NO 76
<211> LENGTH: 12
<212> TYPE: PRT
<213> ORGANISM: Artificial
<220> FEATURE:
<223> OTHER INFORMATION: Amb a 1 fragment

<400> SEQUENCE: 76

Asp Thr His Val Gln Asp Lys Gly Met Leu Ala Thr
1               5                   10

<210> SEQ ID NO 77
<211> LENGTH: 12
<212> TYPE: PRT
<213> ORGANISM: Artificial
<220> FEATURE:
<223> OTHER INFORMATION: Amb a 1 fragment

<400> SEQUENCE: 77

Val Gln Asp Lys Gly Met Leu Ala Thr Val Ala Phe
1               5                   10

<210> SEQ ID NO 78
<211> LENGTH: 12
<212> TYPE: PRT
<213> ORGANISM: Artificial
<220> FEATURE:
<223> OTHER INFORMATION: Amb a 1 fragment

<400> SEQUENCE: 78

Lys Gly Met Leu Ala Thr Val Ala Phe Asn Met Phe
1               5                   10

<210> SEQ ID NO 79
<211> LENGTH: 12
<212> TYPE: PRT
<213> ORGANISM: Artificial
<220> FEATURE:
<223> OTHER INFORMATION: Amb a 1 fragment

<400> SEQUENCE: 79

Leu Ala Thr Val Ala Phe Asn Met Phe Thr Asp Asn
1               5                   10

<210> SEQ ID NO 80
<211> LENGTH: 12
```

```
<212> TYPE: PRT
<213> ORGANISM: Artificial
<220> FEATURE:
<223> OTHER INFORMATION: Amb a 1 fragment

<400> SEQUENCE: 80

Val Ala Phe Asn Met Phe Thr Asp Asn Val Asp Gln
1               5                   10

<210> SEQ ID NO 81
<211> LENGTH: 12
<212> TYPE: PRT
<213> ORGANISM: Artificial
<220> FEATURE:
<223> OTHER INFORMATION: Amb a 1 fragment

<400> SEQUENCE: 81

Asn Met Phe Thr Asp Asn Val Asp Gln Arg Met Pro
1               5                   10

<210> SEQ ID NO 82
<211> LENGTH: 12
<212> TYPE: PRT
<213> ORGANISM: Artificial
<220> FEATURE:
<223> OTHER INFORMATION: Amb a 1 fragment

<400> SEQUENCE: 82

Thr Asp Asn Val Asp Gln Arg Met Pro Arg Cys Arg
1               5                   10

<210> SEQ ID NO 83
<211> LENGTH: 12
<212> TYPE: PRT
<213> ORGANISM: Artificial
<220> FEATURE:
<223> OTHER INFORMATION: Amb a 1 fragment

<400> SEQUENCE: 83

Val Asp Gln Arg Met Pro Arg Cys Arg Phe Gly Phe
1               5                   10

<210> SEQ ID NO 84
<211> LENGTH: 12
<212> TYPE: PRT
<213> ORGANISM: Artificial
<220> FEATURE:
<223> OTHER INFORMATION: Amb a 1 fragment

<400> SEQUENCE: 84

Arg Met Pro Arg Cys Arg Phe Gly Phe Phe Gln Val
1               5                   10

<210> SEQ ID NO 85
<211> LENGTH: 12
<212> TYPE: PRT
<213> ORGANISM: Artificial
<220> FEATURE:
<223> OTHER INFORMATION: Amb a 1 fragment

<400> SEQUENCE: 85

Arg Cys Arg Phe Gly Phe Phe Gln Val Val Asn Asn
1               5                   10

<210> SEQ ID NO 86
<211> LENGTH: 12
<212> TYPE: PRT
```

<213> ORGANISM: Artificial
<220> FEATURE:
<223> OTHER INFORMATION: Amb a 1 fragment

<400> SEQUENCE: 86

Phe Gly Phe Phe Gln Val Val Asn Asn Asn Tyr Asp
1               5                   10

<210> SEQ ID NO 87
<211> LENGTH: 12
<212> TYPE: PRT
<213> ORGANISM: Artificial
<220> FEATURE:
<223> OTHER INFORMATION: Amb a 1 fragment

<400> SEQUENCE: 87

Phe Gln Val Val Asn Asn Asn Tyr Asp Arg Trp Gly
1               5                   10

<210> SEQ ID NO 88
<211> LENGTH: 12
<212> TYPE: PRT
<213> ORGANISM: Artificial
<220> FEATURE:
<223> OTHER INFORMATION: Amb a 1 fragment

<400> SEQUENCE: 88

Val Asn Asn Asn Tyr Asp Arg Trp Gly Thr Tyr Ala
1               5                   10

<210> SEQ ID NO 89
<211> LENGTH: 12
<212> TYPE: PRT
<213> ORGANISM: Artificial
<220> FEATURE:
<223> OTHER INFORMATION: Amb a 1 fragment

<400> SEQUENCE: 89

Asn Tyr Asp Arg Trp Gly Thr Tyr Ala Ile Gly Gly
1               5                   10

<210> SEQ ID NO 90
<211> LENGTH: 12
<212> TYPE: PRT
<213> ORGANISM: Artificial
<220> FEATURE:
<223> OTHER INFORMATION: Amb a 1 fragment

<400> SEQUENCE: 90

Arg Trp Gly Thr Tyr Ala Ile Gly Gly Ser Ser Ala
1               5                   10

<210> SEQ ID NO 91
<211> LENGTH: 12
<212> TYPE: PRT
<213> ORGANISM: Artificial
<220> FEATURE:
<223> OTHER INFORMATION: Amb a 1 fragment

<400> SEQUENCE: 91

Thr Tyr Ala Ile Gly Gly Ser Ser Ala Pro Thr Ile
1               5                   10

<210> SEQ ID NO 92
<211> LENGTH: 12
<212> TYPE: PRT
<213> ORGANISM: Artificial

```
<220> FEATURE:
<223> OTHER INFORMATION: Amb a 1 fragment

<400> SEQUENCE: 92

Ile Gly Gly Ser Ser Ala Pro Thr Ile Leu Cys Gln
1               5                   10

<210> SEQ ID NO 93
<211> LENGTH: 12
<212> TYPE: PRT
<213> ORGANISM: Artificial
<220> FEATURE:
<223> OTHER INFORMATION: Amb a 1 fragment

<400> SEQUENCE: 93

Ser Ser Ala Pro Thr Ile Leu Cys Gln Gly Asn Arg
1               5                   10

<210> SEQ ID NO 94
<211> LENGTH: 12
<212> TYPE: PRT
<213> ORGANISM: Artificial
<220> FEATURE:
<223> OTHER INFORMATION: Amb a 1 fragment

<400> SEQUENCE: 94

Pro Thr Ile Leu Cys Gln Gly Asn Arg Phe Leu Ala
1               5                   10

<210> SEQ ID NO 95
<211> LENGTH: 12
<212> TYPE: PRT
<213> ORGANISM: Artificial
<220> FEATURE:
<223> OTHER INFORMATION: Amb a 1 fragment

<400> SEQUENCE: 95

Leu Cys Gln Gly Asn Arg Phe Leu Ala Pro Asp Asp
1               5                   10

<210> SEQ ID NO 96
<211> LENGTH: 12
<212> TYPE: PRT
<213> ORGANISM: Artificial
<220> FEATURE:
<223> OTHER INFORMATION: Amb a 1 fragment

<400> SEQUENCE: 96

Gly Asn Arg Phe Leu Ala Pro Asp Asp Gln Ile Lys
1               5                   10

<210> SEQ ID NO 97
<211> LENGTH: 12
<212> TYPE: PRT
<213> ORGANISM: Artificial
<220> FEATURE:
<223> OTHER INFORMATION: Amb a 1 fragment

<400> SEQUENCE: 97

Phe Leu Ala Pro Asp Asp Gln Ile Lys Lys Asn Val
1               5                   10

<210> SEQ ID NO 98
<211> LENGTH: 12
<212> TYPE: PRT
<213> ORGANISM: Artificial
<220> FEATURE:
```

<223> OTHER INFORMATION: Amb a 1 fragment

<400> SEQUENCE: 98

Pro Asp Asp Gln Ile Lys Lys Asn Val Leu Ala Arg
1               5                   10

<210> SEQ ID NO 99
<211> LENGTH: 12
<212> TYPE: PRT
<213> ORGANISM: Artificial
<220> FEATURE:
<223> OTHER INFORMATION: Amb a 1 fragment

<400> SEQUENCE: 99

Gln Ile Lys Lys Asn Val Leu Ala Arg Thr Gly Thr
1               5                   10

<210> SEQ ID NO 100
<211> LENGTH: 12
<212> TYPE: PRT
<213> ORGANISM: Artificial
<220> FEATURE:
<223> OTHER INFORMATION: Amb a 1 fragment

<400> SEQUENCE: 100

Lys Asn Val Leu Ala Arg Thr Gly Thr Gly Ala Ala
1               5                   10

<210> SEQ ID NO 101
<211> LENGTH: 12
<212> TYPE: PRT
<213> ORGANISM: Artificial
<220> FEATURE:
<223> OTHER INFORMATION: Amb a 1 fragment

<400> SEQUENCE: 101

Leu Ala Arg Thr Gly Thr Gly Ala Ala Glu Ser Met
1               5                   10

<210> SEQ ID NO 102
<211> LENGTH: 12
<212> TYPE: PRT
<213> ORGANISM: Artificial
<220> FEATURE:
<223> OTHER INFORMATION: Amb a 1 fragment

<400> SEQUENCE: 102

Thr Gly Thr Gly Ala Ala Glu Ser Met Ala Trp Asn
1               5                   10

<210> SEQ ID NO 103
<211> LENGTH: 12
<212> TYPE: PRT
<213> ORGANISM: Artificial
<220> FEATURE:
<223> OTHER INFORMATION: Amb a 1 fragment

<400> SEQUENCE: 103

Gly Ala Ala Glu Ser Met Ala Trp Asn Trp Arg Ser
1               5                   10

<210> SEQ ID NO 104
<211> LENGTH: 12
<212> TYPE: PRT
<213> ORGANISM: Artificial
<220> FEATURE:
<223> OTHER INFORMATION: Amb a 1 fragment

<400> SEQUENCE: 104

Glu Ser Met Ala Trp Asn Trp Arg Ser Asp Lys Asp
1               5                   10

<210> SEQ ID NO 105
<211> LENGTH: 12
<212> TYPE: PRT
<213> ORGANISM: Artificial
<220> FEATURE:
<223> OTHER INFORMATION: Amb a 1 fragment

<400> SEQUENCE: 105

Ala Trp Asn Trp Arg Ser Asp Lys Asp Leu Leu Glu
1               5                   10

<210> SEQ ID NO 106
<211> LENGTH: 12
<212> TYPE: PRT
<213> ORGANISM: Artificial
<220> FEATURE:
<223> OTHER INFORMATION: Amb a 1 fragment

<400> SEQUENCE: 106

Trp Arg Ser Asp Lys Asp Leu Leu Glu Asn Gly Ala
1               5                   10

<210> SEQ ID NO 107
<211> LENGTH: 12
<212> TYPE: PRT
<213> ORGANISM: Artificial
<220> FEATURE:
<223> OTHER INFORMATION: Amb a 1 fragment

<400> SEQUENCE: 107

Asp Lys Asp Leu Leu Glu Asn Gly Ala Ile Phe Val
1               5                   10

<210> SEQ ID NO 108
<211> LENGTH: 12
<212> TYPE: PRT
<213> ORGANISM: Artificial
<220> FEATURE:
<223> OTHER INFORMATION: Amb a 1 fragment

<400> SEQUENCE: 108

Leu Leu Glu Asn Gly Ala Ile Phe Val Thr Ser Gly
1               5                   10

<210> SEQ ID NO 109
<211> LENGTH: 12
<212> TYPE: PRT
<213> ORGANISM: Artificial
<220> FEATURE:
<223> OTHER INFORMATION: Amb a 1 fragment

<400> SEQUENCE: 109

Asn Gly Ala Ile Phe Val Thr Ser Gly Ser Asp Pro
1               5                   10

<210> SEQ ID NO 110
<211> LENGTH: 12
<212> TYPE: PRT
<213> ORGANISM: Artificial
<220> FEATURE:
<223> OTHER INFORMATION: Amb a 1 fragment

```
<400> SEQUENCE: 110

Ile Phe Val Thr Ser Gly Ser Asp Pro Val Leu Thr
1               5                   10

<210> SEQ ID NO 111
<211> LENGTH: 12
<212> TYPE: PRT
<213> ORGANISM: Artificial
<220> FEATURE:
<223> OTHER INFORMATION: Amb a 1 fragment

<400> SEQUENCE: 111

Thr Ser Gly Ser Asp Pro Val Leu Thr Pro Val Gln
1               5                   10

<210> SEQ ID NO 112
<211> LENGTH: 12
<212> TYPE: PRT
<213> ORGANISM: Artificial
<220> FEATURE:
<223> OTHER INFORMATION: Amb a 1 fragment

<400> SEQUENCE: 112

Ser Asp Pro Val Leu Thr Pro Val Gln Ser Ala Gly
1               5                   10

<210> SEQ ID NO 113
<211> LENGTH: 12
<212> TYPE: PRT
<213> ORGANISM: Artificial
<220> FEATURE:
<223> OTHER INFORMATION: Amb a 1 fragment

<400> SEQUENCE: 113

Val Leu Thr Pro Val Gln Ser Ala Gly Met Ile Pro
1               5                   10

<210> SEQ ID NO 114
<211> LENGTH: 12
<212> TYPE: PRT
<213> ORGANISM: Artificial
<220> FEATURE:
<223> OTHER INFORMATION: Amb a 1 fragment

<400> SEQUENCE: 114

Pro Val Gln Ser Ala Gly Met Ile Pro Ala Glu Pro
1               5                   10

<210> SEQ ID NO 115
<211> LENGTH: 12
<212> TYPE: PRT
<213> ORGANISM: Artificial
<220> FEATURE:
<223> OTHER INFORMATION: Amb a 1 fragment

<400> SEQUENCE: 115

Ser Ala Gly Met Ile Pro Ala Glu Pro Gly Glu Ala
1               5                   10

<210> SEQ ID NO 116
<211> LENGTH: 12
<212> TYPE: PRT
<213> ORGANISM: Artificial
<220> FEATURE:
<223> OTHER INFORMATION: Amb a 1 fragment

<400> SEQUENCE: 116
```

Met Ile Pro Ala Glu Pro Gly Glu Ala Ala Ile Lys
1               5                   10

<210> SEQ ID NO 117
<211> LENGTH: 12
<212> TYPE: PRT
<213> ORGANISM: Artificial
<220> FEATURE:
<223> OTHER INFORMATION: Amb a 1 fragment

<400> SEQUENCE: 117

Ala Glu Pro Gly Glu Ala Ala Ile Lys Leu Thr Ser
1               5                   10

<210> SEQ ID NO 118
<211> LENGTH: 12
<212> TYPE: PRT
<213> ORGANISM: Artificial
<220> FEATURE:
<223> OTHER INFORMATION: Amb a 1 fragment

<400> SEQUENCE: 118

Gly Glu Ala Ala Ile Lys Leu Thr Ser Ser Ala Gly
1               5                   10

<210> SEQ ID NO 119
<211> LENGTH: 12
<212> TYPE: PRT
<213> ORGANISM: Artificial
<220> FEATURE:
<223> OTHER INFORMATION: Amb a 1 fragment

<400> SEQUENCE: 119

Ala Ile Lys Leu Thr Ser Ser Ala Gly Val Leu Ser
1               5                   10

<210> SEQ ID NO 120
<211> LENGTH: 12
<212> TYPE: PRT
<213> ORGANISM: Artificial
<220> FEATURE:
<223> OTHER INFORMATION: Amb a 1 fragment

<400> SEQUENCE: 120

Leu Thr Ser Ser Ala Gly Val Leu Ser Cys Arg Pro
1               5                   10

<210> SEQ ID NO 121
<211> LENGTH: 13
<212> TYPE: PRT
<213> ORGANISM: Artificial
<220> FEATURE:
<223> OTHER INFORMATION: Amb a 1 fragment

<400> SEQUENCE: 121

Ser Ala Gly Val Leu Ser Cys Arg Pro Gly Ala Pro Cys
1               5                   10

<210> SEQ ID NO 122
<211> LENGTH: 15
<212> TYPE: PRT
<213> ORGANISM: Artificial
<220> FEATURE:
<223> OTHER INFORMATION: Amb a 1 fragment

<400> SEQUENCE: 122

```
Val Ala Phe Asn Met Phe Thr Asp Asn Val Asp Gln Arg Met Pro
1               5                   10                  15
```

<210> SEQ ID NO 123
<211> LENGTH: 15
<212> TYPE: PRT
<213> ORGANISM: Artificial
<220> FEATURE:
<223> OTHER INFORMATION: Amb a 1 fragment

<400> SEQUENCE: 123

```
Val Asn Asn Asn Tyr Asp Arg Trp Gly Thr Tyr Ala Ile Gly Gly
1               5                   10                  15
```

<210> SEQ ID NO 124
<211> LENGTH: 15
<212> TYPE: PRT
<213> ORGANISM: Artificial
<220> FEATURE:
<223> OTHER INFORMATION: Amb a 1 fragment

<400> SEQUENCE: 124

```
Pro Asp Asp Gln Ile Lys Lys Asn Val Leu Ala Arg Thr Gly Thr
1               5                   10                  15
```

<210> SEQ ID NO 125
<211> LENGTH: 15
<212> TYPE: PRT
<213> ORGANISM: Artificial
<220> FEATURE:
<223> OTHER INFORMATION: Amb a 1 fragment

<400> SEQUENCE: 125

```
Leu Ala Arg Thr Gly Thr Gly Ala Ala Glu Ser Met Ala Trp Asn
1               5                   10                  15
```

<210> SEQ ID NO 126
<211> LENGTH: 15
<212> TYPE: PRT
<213> ORGANISM: Artificial
<220> FEATURE:
<223> OTHER INFORMATION: Amb a 1 fragment

<400> SEQUENCE: 126

```
Glu Gly Thr Leu Arg Phe Ala Ala Ala Gln Asn Arg Pro Leu Trp
1               5                   10                  15
```

<210> SEQ ID NO 127
<211> LENGTH: 15
<212> TYPE: PRT
<213> ORGANISM: Artificial
<220> FEATURE:
<223> OTHER INFORMATION: Amb a 1 fragment

<400> SEQUENCE: 127

```
Gln Asn Arg Pro Leu Trp Ile Ile Phe Lys Asn Asp Met Val Ile
1               5                   10                  15
```

<210> SEQ ID NO 128
<211> LENGTH: 15
<212> TYPE: PRT
<213> ORGANISM: Artificial
<220> FEATURE:
<223> OTHER INFORMATION: Amb a 1 fragment

<400> SEQUENCE: 128

```
Lys Asn Asp Met Val Ile Asn Leu Asn Gln Glu Leu Val Val Asn
1               5                   10                  15
```

-continued

```
<210> SEQ ID NO 129
<211> LENGTH: 15
<212> TYPE: PRT
<213> ORGANISM: Artificial
<220> FEATURE:
<223> OTHER INFORMATION: Amb a 1 fragment

<400> SEQUENCE: 129

Gln Glu Leu Val Val Asn Ser Asp Lys Thr Ile Asp Gly Arg Gly
1               5                   10                  15

<210> SEQ ID NO 130
<211> LENGTH: 18
<212> TYPE: PRT
<213> ORGANISM: Artificial
<220> FEATURE:
<223> OTHER INFORMATION: Amb a 1 fragment

<400> SEQUENCE: 130

Lys Asn Ile Ile Ile His Asn Ile Asn Ile His Asp Val Lys Val Leu
1               5                   10                  15

Pro Gly

<210> SEQ ID NO 131
<211> LENGTH: 18
<212> TYPE: PRT
<213> ORGANISM: Artificial
<220> FEATURE:
<223> OTHER INFORMATION: Amb a 1 fragment

<400> SEQUENCE: 131

Asn Gly Ala Ile Phe Val Thr Ser Gly Ser Asp Pro Val Leu Thr Pro
1               5                   10                  15

Val Gln

<210> SEQ ID NO 132
<211> LENGTH: 18
<212> TYPE: PRT
<213> ORGANISM: Artificial
<220> FEATURE:
<223> OTHER INFORMATION: Amb a 1 fragment

<400> SEQUENCE: 132

Gly Glu Ala Ala Ile Lys Leu Thr Ser Ser Ala Gly Val Leu Ser Cys
1               5                   10                  15

Arg Pro

<210> SEQ ID NO 133
<211> LENGTH: 18
<212> TYPE: PRT
<213> ORGANISM: Artificial
<220> FEATURE:
<223> OTHER INFORMATION: Amb a 1 fragment

<400> SEQUENCE: 133

Ser Asp Lys Thr Ile Asp Gly Arg Gly Val Lys Val Glu Ile Ile Asn
1               5                   10                  15

Gly Gly

<210> SEQ ID NO 134
<211> LENGTH: 15
<212> TYPE: PRT
```

<213> ORGANISM: Artificial
<220> FEATURE:
<223> OTHER INFORMATION: Amb a 1 fragment

<400> SEQUENCE: 134

Pro Val Gln Ser Ala Gly Met Ile Pro Ala Glu Pro Gly Glu Ala
1               5                   10                  15

<210> SEQ ID NO 135
<211> LENGTH: 18
<212> TYPE: PRT
<213> ORGANISM: Artificial
<220> FEATURE:
<223> OTHER INFORMATION: Amb a 1 fragment

<400> SEQUENCE: 135

Asn Val Ala Gly Ser Ser Gln Ile Trp Ile Asp His Cys Ser Leu Ser
1               5                   10                  15

Lys Ser

<210> SEQ ID NO 136
<211> LENGTH: 15
<212> TYPE: PRT
<213> ORGANISM: Artificial
<220> FEATURE:
<223> OTHER INFORMATION: Amb a 1 fragment

<400> SEQUENCE: 136

Asp Lys Asp Leu Leu Glu Asn Gly Ala Ile Phe Val Thr Ser Gly
1               5                   10                  15

<210> SEQ ID NO 137
<211> LENGTH: 15
<212> TYPE: PRT
<213> ORGANISM: Artificial
<220> FEATURE:
<223> OTHER INFORMATION: Amb a 1 fragment

<400> SEQUENCE: 137

Gly Ser Ser Gln Ile Trp Ile Asp His Cys Ser Leu Ser Lys Ser
1               5                   10                  15

<210> SEQ ID NO 138
<211> LENGTH: 24
<212> TYPE: PRT
<213> ORGANISM: Artificial
<220> FEATURE:
<223> OTHER INFORMATION: Amb a 1 fragment

<400> SEQUENCE: 138

Asp Lys Asp Leu Leu Glu Asn Gly Ala Ile Phe Val Thr Ser Gly Ser
1               5                   10                  15

Asp Pro Val Leu Thr Pro Val Gln
            20

<210> SEQ ID NO 139
<211> LENGTH: 15
<212> TYPE: PRT
<213> ORGANISM: Artificial
<220> FEATURE:
<223> OTHER INFORMATION: Amb a 1 fragment

<400> SEQUENCE: 139

Ala Ile Lys Leu Thr Ser Ser Ala Gly Val Leu Ser Cys Arg Pro
1               5                   10                  15

<210> SEQ ID NO 140
<211> LENGTH: 44
<212> TYPE: DNA
<213> ORGANISM: Artificial
<220> FEATURE:
<223> OTHER INFORMATION: Primer

<400> SEQUENCE: 140
gagagagacc atggccgaag ggtcggaga aatcttacct tcag          44

<210> SEQ ID NO 141
<211> LENGTH: 42
<212> TYPE: DNA
<213> ORGANISM: Artificial
<220> FEATURE:
<223> OTHER INFORMATION: Primer

<400> SEQUENCE: 141
gagagagact cgagttagca aggtgctcca ggacggcatg ag            42

<210> SEQ ID NO 142
<211> LENGTH: 211
<212> TYPE: PRT
<213> ORGANISM: Artificial
<220> FEATURE:
<223> OTHER INFORMATION: Amb a 1 alpha chain

<400> SEQUENCE: 142

Pro Ile Leu Arg Gln Ala Ser Asp Gly Asp Thr Ile Asn Val Ala Gly
1               5                   10                  15

Ser Ser Gln Ile Trp Ile Asp His Cys Ser Leu Ser Lys Ser Phe Asp
            20                  25                  30

Gly Leu Val Asp Val Thr Leu Gly Ser Thr His Val Thr Ile Ser Asn
        35                  40                  45

Cys Lys Phe Thr Gln Gln Ser Lys Ala Ile Leu Leu Gly Ala Asp Asp
    50                  55                  60

Thr His Val Gln Asp Lys Gly Met Leu Ala Thr Val Ala Phe Asn Met
65                  70                  75                  80

Phe Thr Asp Asn Val Asp Gln Arg Met Pro Arg Cys Arg Phe Gly Phe
                85                  90                  95

Phe Gln Val Val Asn Asn Asn Tyr Asp Arg Trp Gly Thr Tyr Ala Ile
            100                 105                 110

Gly Gly Ser Ser Ala Pro Thr Ile Leu Cys Gln Gly Asn Arg Phe Leu
        115                 120                 125

Ala Pro Asp Asp Gln Ile Lys Lys Asn Val Leu Ala Arg Thr Gly Thr
    130                 135                 140

Gly Ala Ala Glu Ser Met Ala Trp Asn Trp Arg Ser Asp Lys Asp Leu
145                 150                 155                 160

Leu Glu Asn Gly Ala Ile Phe Val Thr Ser Gly Ser Asp Pro Val Leu
                165                 170                 175

Thr Pro Val Gln Ser Ala Gly Met Ile Pro Ala Glu Pro Gly Glu Ala
            180                 185                 190

Ala Ile Lys Leu Thr Ser Ser Ala Gly Val Leu Ser Cys Arg Pro Gly
        195                 200                 205

Ala Pro Cys
    210

<210> SEQ ID NO 143
<211> LENGTH: 224

```
<212> TYPE: PRT
<213> ORGANISM: Artificial
<220> FEATURE:
<223> OTHER INFORMATION: Amb a 1 alpha chain

<400> SEQUENCE: 143

Val Leu Pro Gly Gly Met Ile Lys Ser Asn Asp Gly Pro Pro Ile Leu
1               5                   10                  15

Arg Gln Ala Ser Asp Gly Asp Thr Ile Asn Val Ala Gly Ser Ser Gln
            20                  25                  30

Ile Trp Ile Asp His Cys Ser Leu Ser Lys Ser Phe Asp Gly Leu Val
        35                  40                  45

Asp Val Thr Leu Gly Ser Thr His Val Thr Ile Ser Asn Cys Lys Phe
    50                  55                  60

Thr Gln Gln Ser Lys Ala Ile Leu Leu Gly Ala Asp Asp Thr His Val
65                  70                  75                  80

Gln Asp Lys Gly Met Leu Ala Thr Val Ala Phe Asn Met Phe Thr Asp
                85                  90                  95

Asn Val Asp Gln Arg Met Pro Arg Cys Arg Phe Gly Phe Phe Gln Val
            100                 105                 110

Val Asn Asn Asn Tyr Asp Arg Trp Gly Thr Tyr Ala Ile Gly Gly Ser
        115                 120                 125

Ser Ala Pro Thr Ile Leu Cys Gln Gly Asn Arg Phe Leu Ala Pro Asp
    130                 135                 140

Asp Gln Ile Lys Lys Asn Val Leu Ala Arg Thr Gly Thr Gly Ala Ala
145                 150                 155                 160

Glu Ser Met Ala Trp Asn Trp Arg Ser Asp Lys Asp Leu Leu Glu Asn
                165                 170                 175

Gly Ala Ile Phe Val Thr Ser Gly Ser Asp Pro Val Leu Thr Pro Val
            180                 185                 190

Gln Ser Ala Gly Met Ile Pro Ala Glu Pro Gly Glu Ala Ala Ile Lys
        195                 200                 205

Leu Thr Ser Ser Ala Gly Val Leu Ser Cys Arg Pro Gly Ala Pro Cys
    210                 215                 220

<210> SEQ ID NO 144
<211> LENGTH: 161
<212> TYPE: PRT
<213> ORGANISM: Artificial
<220> FEATURE:
<223> OTHER INFORMATION: Amb a 1 beta chain

<400> SEQUENCE: 144

Ala Glu Gly Val Gly Glu Ile Leu Pro Ser Val Asn Glu Thr Arg Ser
1               5                   10                  15

Leu Gln Ala Cys Glu Ala Tyr Asn Ile Ile Asp Lys Cys Trp Arg Gly
            20                  25                  30

Lys Ala Asp Trp Glu Asn Asn Arg Gln Ala Leu Ala Asp Cys Ala Gln
        35                  40                  45

Gly Phe Ala Lys Gly Thr Tyr Gly Gly Lys Trp Gly Asp Val Tyr Thr
    50                  55                  60

Val Thr Ser Asn Leu Asp Asp Val Ala Asn Pro Lys Glu Gly Thr
65                  70                  75                  80

Leu Arg Phe Ala Ala Ala Gln Asn Arg Pro Leu Trp Ile Ile Phe Lys
                85                  90                  95

Asn Asp Met Val Ile Asn Leu Asn Gln Glu Leu Val Val Asn Ser Asp
            100                 105                 110
```

```
Lys Thr Ile Asp Gly Arg Gly Val Lys Val Glu Ile Ile Asn Gly Gly
        115                 120                 125

Leu Thr Leu Met Asn Val Lys Asn Ile Ile Ile His Asn Ile Asn Ile
        130                 135                 140

His Asp Val Lys Val Leu Pro Gly Gly Met Ile Lys Ser Asn Asp Gly
145                 150                 155                 160

Pro

<210> SEQ ID NO 145
<211> LENGTH: 148
<212> TYPE: PRT
<213> ORGANISM: Artificial
<220> FEATURE:
<223> OTHER INFORMATION: Amb a 1 beta chain

<400> SEQUENCE: 145

Ala Glu Gly Val Gly Glu Ile Leu Pro Ser Val Asn Glu Thr Arg Ser
1               5                   10                  15

Leu Gln Ala Cys Glu Ala Tyr Asn Ile Ile Asp Lys Cys Trp Arg Gly
            20                  25                  30

Lys Ala Asp Trp Glu Asn Asn Arg Gln Ala Leu Ala Asp Cys Ala Gln
        35                  40                  45

Gly Phe Ala Lys Gly Thr Tyr Gly Gly Lys Trp Gly Asp Val Tyr Thr
    50                  55                  60

Val Thr Ser Asn Leu Asp Asp Val Ala Asn Pro Lys Glu Gly Thr
65                  70                  75                  80

Leu Arg Phe Ala Ala Ala Gln Asn Arg Pro Leu Trp Ile Ile Phe Lys
            85                  90                  95

Asn Asp Met Val Ile Asn Leu Asn Gln Glu Leu Val Val Asn Ser Asp
                100                 105                 110

Lys Thr Ile Asp Gly Arg Gly Val Lys Val Glu Ile Ile Asn Gly Gly
        115                 120                 125

Leu Thr Leu Met Asn Val Lys Asn Ile Ile Ile His Asn Ile Asn Ile
        130                 135                 140

His Asp Val Lys
145
```